(12) United States Patent
Takakura et al.

(10) Patent No.: US 11,659,807 B2
(45) Date of Patent: May 30, 2023

(54) VIRUS-RESISTANT TOBACCO AND BREEDING METHOD THEREFOR

(71) Applicant: JAPAN TOBACCO INC., Tokyo (JP)

(72) Inventors: Yoshimitsu Takakura, Tokyo (JP); Akira Shinjo, Tokyo (JP); Hisashi Udagawa, Tokyo (JP); Kazuharu Koga, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/284,600

(22) Filed: Feb. 25, 2019

(65) Prior Publication Data

US 2019/0174706 A1 Jun. 13, 2019

Related U.S. Application Data

(63) Continuation of application No. PCT/JP2017/030492, filed on Aug. 25, 2017.

(30) Foreign Application Priority Data

Aug. 26, 2016 (JP) .............................. JP2016-166176

(51) Int. Cl.
| | |
|---|---|
| *A01H 5/12* | (2018.01) |
| *A01H 6/82* | (2018.01) |
| *A24B 1/00* | (2006.01) |
| *C12N 15/09* | (2006.01) |
| *A01H 1/00* | (2006.01) |
| *A01H 1/06* | (2006.01) |
| *C12Q 1/6895* | (2018.01) |
| *C12Q 1/6897* | (2018.01) |

(52) U.S. Cl.
CPC .............. *A01H 6/823* (2018.05); *A01H 1/00* (2013.01); *A01H 1/06* (2013.01); *A01H 5/12* (2013.01); *A24B 1/00* (2013.01); *C12N 15/09* (2013.01); *C12Q 1/6895* (2013.01); *C12Q 1/6897* (2013.01)

(58) Field of Classification Search
None
See application file for complete search history.

(56) References Cited

U.S. PATENT DOCUMENTS

| | | | |
|---|---|---|---|
| 7,772,462 | B2 | 8/2010 | Jahn et al. |
| 8,298,819 | B2 | 10/2012 | Takakura et al. |
| 2006/0294618 | A1 | 12/2006 | Jahn et al. |
| 2013/0056014 | A1 | 3/2013 | Noguchi et al. |
| 2013/0117879 | A1 | 5/2013 | Walsh et al. |
| 2017/0107533 | A1 | 4/2017 | Takakura et al. |

FOREIGN PATENT DOCUMENTS

| | | | |
|---|---|---|---|
| CN | 101397569 A | | 4/2009 |
| EP | 2 208 788 A1 | | 7/2010 |
| NZ | 551521 A | | 9/2009 |
| WO | WO 2004/057941 A2 | | 7/2004 |
| WO | WO 2005/118850 A1 | | 12/2005 |
| WO | WO 2011/102394 A1 | | 8/2011 |
| WO | WO 2015/199242 A1 | | 12/2015 |

OTHER PUBLICATIONS

Chung et al., "Resistance to multiple viruses in transgenic tobacco expressing fused, tandem repeat, virus-derived double-stranded RNAs," Virus Genes, vol. 43, 2011 (published online Aug. 19, 2011), pp. 454-464.
European Office Action for European Application No. 17843725.7, dated Sep. 21, 2020.
Brazilian Office Action and Search Report, dated Dec. 17, 2019, for Brazilian Application No. BR112016030279-6, along with an English translation.
Shain et al. "The Spectrum of SWI/SNF Mutations, Ubiquitous in Human Cancers," PLOS ONE, Jan. 2013, vol. 8, Issue 1, pp. 1-11.
Agarwal et al., "Advances in molecular marker techniques and their applications in plant sciences," Plant Cell Rep., vol. 27, No. 4, 2008 (published online Feb. 2, 2008), pp. 617-631.
Ala-Poikela et al., "Helper Component Proteinase of the Genus Potyvirus is an Interaction Partner of Translation Initiation Factors eIF(iso)4E and eIF4E and Contains a 4E Binding Motif," J Virol., vol. 85, No. 13, Jul. 2011 (published ahead of print on Apr. 27, 2011), pp. 6784-6794.
Albar et al., "Mutations in the eIF(iso)4G translation initiation factor confer high resistance of rice to Rice yellow mottle virus," Plant J., vol. 47, No. 3, 2006, pp. 417-426.
Altschul et al., "Basic local alignment search tool," J. Mol. Biol., vol. 215, No. 3, 1990, pp. 403-410.
Baker et al., "Nonsense-mediated mRNA decay: terminating erroneous gene expression," Current Opinion in Cell Biology, vol. 16, No. 3, 2004, pp. 293-299.
Belhaj et al., "Plant genome editing made easy: targeted mutagenesis in model and crop plants using the CRISPR/Cas system," Plant Methods, vol. 9, No. 39, Oct. 11, 2013, pp. 1-10.
Boiteux et al., "Breeding for Resistance to Viral Diseases," Plant Breeding for Biotic Stress Resistance, Springer-Verlag Berlin Heidelberg, 2012, pp. 57-79.
Brogna et al., "Nonsense-mediated mRNAdecay (NMD) mechanisms," Nat. Structural Mol. Biol., vol. 16, No. 2, Feb. 2009 (published online Feb. 4, 2009), pp. 107-113.

(Continued)

*Primary Examiner* — Elizabeth F McElwain
(74) *Attorney, Agent, or Firm* — Birch, Stewart, Kolasch & Birch, LLP

(57) ABSTRACT

In order to provide tobacco resistant to a virus, tobacco in accordance with the present invention is arranged such that: (i) a translation initiation factor eIF(iso)4E protein which is non-functional with respect to a virus is produced or (ii) expression of a translation initiation factor eIF(iso)4E gene is suppressed; and (a) a translation initiation factor eIF4E2 protein, which is non-functional with respect to a virus, is produced or (b) expression of a translation initiation factor eIF4E2 gene is suppressed.

15 Claims, 1 Drawing Sheet

Specification includes a Sequence Listing.

(56) References Cited

OTHER PUBLICATIONS

Cavatorta et al., "Engineering virus resistance using a modified potato gene," Plant Biotechnology Journal, vol. 9, No. 9, 2011, pp. 1014-1021.
Chinese Office Action and Search Report dated Apr. 23, 2018, in Chinese Patent Application No. 201580035068.6, with English translation.
Combe et al., "Translation initiation factors eIF4E and eIFiso4E are required for polysome formation and regulate plant growth in tobacco," Plant Molecular Biology, vol. 57, No. 5, 2005, pp. 749-760.
De Bruin, "Sources of resistance in the genus Nicotiana to the virus causing bushy top disease in tobacco," Phytophylactica, vol. 22, No. 2, 1990, pp. 263-264.
Decroocq et al., "Multiple Resistance Traits Control Plum pox virus Infection in *Arabidopsis thaliana*," Molecular Plant-Microbe Interactions, vol. 19, No. 5, 2006, pp. 541-549.
Dunoyer et al., "A cysteine-rich plant protein potentiates Potyvirus movement through an interaction with the virus genome-linked protein VPg," Journal of Virology, vol. 78, No. 5, Mar. 2004, pp. 2301-2309 (10 pages).
Durai et al., "Zinc finger nucleases: custom-designed molecular scissors for genome engineering of plant and mammalian cells," Nucleic Acids Res., vol. 33, No. 18, 2005 (published online Oct. 26, 2005), pp. 5978-5990.
Extended European Search Report dated Nov. 21, 2017, in European Patent Application No. 15811561.8.
Freire, M. A., "Potyviral VPg and HC-Pro Proteins and the Cellular Translation Initiation Factor eIF(iso)4E Interact with Exoribonuclease Rrp6 and a Small α-Heat Shock Protein," Plant Mol. Biol. Rep., vol. 32, 2014 (published online Oct. 15, 2013), pp. 596-604.
Gong, "Important Tobacco Genes: 1. Tobacco Disease Restistance Related Genes," Chinese Tobacco Science (2014), vol. 35, No. 1, pp. 133-135 (9 pages), with English translation.
Hellens et al., "pGreen: a versatile and flexible binary Ti vector for Agrobacterium-mediated plant transformation," Plant Mol. Biol., vol. 42, No. 6, 2000, pp. 819-832.
Henderson et al., "A Severe Virus Disease of Tobacco in Montgomery County, Virginia," Plant Disease Reporter, vol. 47, No. 3, Mar. 15, 1963, pp. 187-189.
Hipper et al., "Viral and cellular factors involved in Phloem transport of plant viruses," Frontiers in Plant Science, vol. 4, Article 154, May 24, 2013, pp. 1-24.
Huang et al., "A host RNA helicase-like protein, AtRH8, interacts with the potyviral genome-linked protein, VPg, associates with the virus accumulation complex, and is essential for infection," Plant Physiol., vol. 152, No. 1, Jan. 2010, pp. 255-266.
Hwang et al., "Translation elongation factor 1B (eEF1B) is an essential host factor for Tobacco mosaic virus infection in plants," Virology, vol. 439, No. 2, May 2013, pp. 1-10.
International Preliminary Report on Patentability and Written Opinion of the International Searching Authority for International Application No. PCT/JP2017/030492, dated Mar. 7, 2019.
International Search Report, dated Nov. 28, 2017, for International Application No. PCT/JP2017/030492.
International Search Report, dated Oct. 6, 2015, for International Application No. PCT/JP2015/068713.
Julio et al., "A Eukaryotic Translation Initiation Factor 4E (eIF4E) is Responsible for the "va" Tobacco Recessive Resistance to Potyviruses," Plant Mol Biol Rep, vol. 33, 2015 (published online Aug. 12, 2014), pp. 609-623.
Julio et al., "Characterization of PVY (Potato Virus Y) resistance in tobacco: potential role of an eIF4E gene identified by high throughput sequencing technologies," AP 2013, Brufa di Torgiano, 15 pages.
Julio et al., "Nicotiana tabacum eukaryotic translation initiation factor 4E (eIF4E) mRNA, complete cds," GenBank, Accession No. KF155696.1, Sep. 15, 2015, 1 page.
Julio et al., "Nicotiana tabacum isolate T021658 eukaryotic initiation factor 4E mRNA, complete cds," GenBank, Accession No. KM202068.1, Sep. 15, 2015, 1 page.
Julio et al., "Characterization of PVY (Potato Virus Y) Resistance in Tobacco: Potential Role of an eIF4E Gene Identified by High Throughput Sequencing Technologies," 2013 CORESTA Joint Study Groups Meeting—Agro-Phyto Abstracts, AP 29, 2013, p. 30.
Jung et al., "Exploring natural variations in eIF4E and screening for potyviral resistance in diverse Nicotiana species," Hort. Environ. Biotechnol., vol. 54, No. 5, 2013, pp. 430-440.
Komari et al., "Binary vectors and super-binary vectors," Methods in Mol. Biol., vol. 343, 2006, pp. 15-41.
Lellis et al., "Loss-of-susceptibility mutants of *Arabidopsis thaliana* reveal an essential role for eIF(iso)4E during potyvirus infection," Current Biology, vol. 12, No. 12, Jun. 25, 2002, pp. 1046-1051.
Lusser et al., "Deployment of new biotechnologies in plant breeding," Nature Biotechnology, vol. 30, No. 3, Mar. 2012, pp. 231-239.
Masuta et al., "A Single Amino Acid Change in Viral Genome-Associated Protein of Potato Virus Y Correlates with Resistance Breaking in 'Virgin A Mutant' Tobacco," Phytopathology, vol. 89, No. 2, 1999, pp. 118-123.
Mazier et al., "Knock-Down of Both eIF4E1 and eIF4E2 Genes Confers Broad-Spectrum Resistance against Potyviruses in Tomato," PLoS ONE, vol. 6, Issue 12, e29595, Dec. 29, 2011, pp. 1-10.
Mo et al., "Complete nucleotide sequence and genome organization of a Chinese isolate of tobacco bushy top virus," Archives of Virology, vol. 148, No. 2, 2003 (published online Nov. 18, 2002), pp. 389-397.
Neff et al., "dCAPS, a simple technique for the genetic analysis of single nucleotide polymorphisms: experimental applications in *Arabidopsis thaliana* genetics," Plant J., vol. 14, No. 3, 1998, pp. 387-392.
Neff et al., "Web-based primer design for single nucleotide polymorphism analysis," TRENDS in Genetics, vol. 18, No. 12, Dec. 2002 (published online Nov. 1, 2002), pp. 613-615.
Nieto et al., "An eIF4E allele confers resistance to an uncapped and non-polyadenylated RNA virus in melon," The Plant Journal, vol. 48, No. 3, 2006, pp. 452-462.
Oh et al., "Oligonucleotide-directed plant gene targeting," Current Opinion in Biotechnology, vol. 12, No. 2, 2001, pp. 169-172.
Pi et al., "Cloning of PVY Associated Gene eIF4E and Construction of Its Corresponding RNAi Vectors," Chinese Agricultural Science Bulletin (2012), vol. 28, No. 18, pp. 189-193 (17 pages), with English translation.
Piron at al., "An Induced Mutation in Tomato eIF4E Leads to Immunity to Two Potyviruses," PLoS ONE, vol. 5, Issue 6, e11313, Jun. 25, 2010, pp. 1-10.
Pulcinelli et al., "Reporting a source of PVY$^{ntn}$ resistance in Nicotiana tabacum L.," Souza Cruz, CORESTA, 2009 Joint Study Groups Meeting, Rovinj, Croatia, 2009, 32 pages.
Robaglia et al., "Translation initiation factors: a weak link in plant RNA virus infection," Trends in Plant Science, vol. 11, No. 1, Jan. 2006 (available online Dec. 15, 2005), pp. 40-45.
Ruffel et al., "A natural recessive resistance gene against potato virus Y in pepper corresponds to the eukaryotic initiation factor 4E (eIF4E)," Plant J., vol. 32, No. 6, 2002, pp. 1067-1075.
Ruffel et al., "Simultaneous mutations in translation initiation factors eIF4E and eIF(isb)4E are required to prevent pepper veinal mottle virus infection of pepper," J Gen Virol., vol. 87, 2006, pp. 2089-2098.
Sato et al., "Host factors and its relevance to virus infection in plants," Virus, vol. 56, No. 2, Dec. 2006, pp. 155-164, with an English abstract.
Sato et al., "Selective involvement of members of the eukaryotic initiation factor 4E family in the infection of *Arabidopsis thaliana* by potyviruses," FEBS Letters, vol. 579, No. 5, 2005 (available online Jan. 19, 2005), pp. 1167-1171.
Tajima et al., "Construction of Mutant Panel in Nicotiana tabacum L.," Japanese Journal of Phytopathology, vol. 77, No. 3, Aug. 2011, p. 258 (2 pages), with a partial English translation.
Truniger et al., "Recessive resistance to plant viruses," Adv Virus Res., vol. 75, 2009, pp. 119-159 (42 pages).

(56) References Cited

OTHER PUBLICATIONS

Vincentz et al., "Constitutive expression of nitrate reductase allows normal growth and development of Nicotiana plumbaginifolia plants," EMBO J., vol. 10, No. 5, 1991, pp. 1027-1035.
Wang et al., "Silencing of the Host Factor eIF(iso)4E Gene Confers Plum Pox Virus Resistance in Plum," PLoS ONE, vol. 8, Issue 1, e50627, Jan. 28, 2013, pp. 1-12.
Wesley et al., "Construct design for efficient, effective and high-throughput gene silencing in plants," Plant J., vol. 27, No. 6, 2001, pp. 581-590.
Yamamoto, "Studies on Breeding of Tobacco Varieties Resistant to Veinal Necrosis Disease by Potato Virus Y Strain T," Bulletin of the Leaf Tobacco Research Laboratory, No. 2, Mar. 1992, pp. 78-79.
Yoshii et al., "The Arabidopsis Cucumovirus Multiplication 1 and 2 Loci Encode Translation Initiation Factors 4E and 4G," J Virol., vol. 78, No. 12, Jun. 2004, pp. 6102-6111 (11 pages).
Zhang et al., "Transcription activator-like effector nucleases enable efficient plant genome engineering," Plant Physiology, vol. 161, No. 1, Jan. 2013, pp. 20-27.
Zhu et al., "Targeted manipulation of maize genes in vivo using chimeric RNA/DNA oligonucleotides," Proc. Natl. Acad. Sci. USA, vol. 96, No. 15, Jul. 1999, pp. 8768-8773.
Indonesian Office Action dated Feb. 22, 2021 for ID Application No. PID201902366 (with English Translation).
Indonesian Office Action dated Feb. 22, 2021 for ID Application No. PID201902366.
European Office Action dated Nov. 18, 2022 for European Patent Application No. 15811561.8.
Lacroix et al.; "Effect of passage of a Potato virus Y isolate on a line of tobacco containing the recessive resistance aene va 2 on the development of isolates capable of overcoming alleles 0 and 2". Euro Journal of Plant Pathology, vol. 130, pp. 259-269,(Feb. 24, 2011),DOI:10.1007/s10658-011-9751-0.

SEQUENCE LISTING

<160> NUMBER OF SEQ ID NOS: 40

<210> SEQ ID NO 1
<211> LENGTH: 1020
<212> TYPE: DNA
<213> ORGANISM: Nicotiana tabacum

<400> SEQUENCE: 1

```
ttttaagtta cagtccaaac tgaggaaaag gaaagtcttg aaccaaagaa aaactacaag      60
taccctttc ctactaaaat ctataactga gtacatagaa aacacacgaa aatggcagag     120
gaagctgaga aattgcgggt agatgaagta gaagtagccg acgatggacc tgaagaagga     180
gaaattgtgg atgaatctga tgatacggcg tcgtatttgg gcaaagaaat caaacctaag     240
catccattag agaattcttg gacttttggg tttgataatc ctatggctaa atctagacaa     300
gctgcttggg gcagttccct tcgcgaactt tacactttt ccactgtcga agatttttgg      360
ggtgtttaca ataatatcaa ccacccaagc aagttagttg tgggagcaga cttttcattgt    420
tttaagcata aaattgagcc aaagtgggaa gatcctgtat gtgcgaatgg agggaattgg     480
acaatgagct ttagtaaggg taaatctgat accagctggc tatacacgct gctggcaatg     540
attggacatc aattcgatca tggagaggaa atttgtggag cagtagttag cgtccgaaat     600
aaggggata aaatagcttt atggaccaag aatgctgcaa atgaaacagc tcaggttagc     660
attggtaagc aatggaagga gtttctggat tacagcaact cgattggctt catatttcat     720
gacgactcaa tgaggctcgg cagaggtgcc aagaatcgtt atacagtata gttttcttgc     780
tacaatgggg gaatgcaaga aacagaatct ggactggaaa gtttatagac attagctctg    840
tttgtacaat catctatcat atgaaaggct gccacttgac agtttaagta cctttgtttt    900
agtgtttgta cttttaatcg aagaaactcg tttggttttg aattaatgcc ttaacaataa    960
actttagtcc tgtctctttt tctaacaact tgtttgaaca attgttatgt atcgtttcat   1020
```

<210> SEQ ID NO 2
<211> LENGTH: 219
<212> TYPE: PRT
<213> ORGANISM: Nicotiana tabacum

<400> SEQUENCE: 2

```
Met Ala Glu Glu Ala Glu Lys Leu Arg Val Asp Glu Val Glu Val Ala
1               5                   10                  15

Asp Asp Gly Pro Glu Glu Gly Glu Ile Val Asp Glu Ser Asp Asp Thr
            20                  25                  30

Ala Ser Tyr Leu Gly Lys Glu Ile Lys Pro Lys His Pro Leu Glu Asn
        35                  40                  45

Ser Trp Thr Phe Trp Phe Asp Asn Pro Met Ala Lys Ser Arg Gln Ala
    50                  55                  60

Ala Trp Gly Ser Ser Leu Arg Glu Leu Tyr Thr Phe Ser Thr Val Glu
65                  70                  75                  80

Asp Phe Trp Gly Val Tyr Asn Asn Ile Asn His Pro Ser Lys Leu Val
                85                  90                  95

Val Gly Ala Asp Phe His Cys Phe Lys His Lys Ile Glu Pro Lys Trp
            100                 105                 110
```

```
Glu Asp Pro Val Cys Ala Asn Gly Gly Asn Trp Thr Met Ser Phe Ser
            115                 120                 125

Lys Gly Lys Ser Asp Thr Ser Trp Leu Tyr Thr Leu Leu Ala Met Ile
130                 135                 140

Gly His Gln Phe Asp His Gly Glu Glu Ile Cys Gly Ala Val Val Ser
145                 150                 155                 160

Val Arg Asn Lys Gly Asp Lys Ile Ala Leu Trp Thr Lys Asn Ala Ala
                165                 170                 175

Asn Glu Thr Ala Gln Val Ser Ile Gly Lys Gln Trp Lys Glu Phe Leu
            180                 185                 190

Asp Tyr Ser Asn Ser Ile Gly Phe Ile Phe His Asp Asp Ser Met Arg
        195                 200                 205

Leu Gly Arg Gly Ala Lys Asn Arg Tyr Thr Val
    210                 215

<210> SEQ ID NO 3
<211> LENGTH: 6000
<212> TYPE: DNA
<213> ORGANISM: Nicotiana tabacum

<400> SEQUENCE: 3
gccaaacagg ctattaaggg actactttaa cgattttgta atttatggct attttttaa       60 ttactagctc aaaaatggct atttttaaac tttagccact aatattccac cgtcctggat     120
aaagattatt tttaagttac agtccaaact gaggaaaagg aaagtcttga accaaagaaa     180
aactacaagt acccttttcc tactaaaatc tataactaag tacatagaaa acacacgaaa     240
atggcagagg aagctgagaa attgcgggta gatgaagtag aagtagtcga cgatggacct     300
gaagaaggag aaattgtgga tgaatctgat gatacggcgt cgtatttggg caaagaaatc     360
aaacctaagc atccattaga gaattcttgg acttttggt ttgataatcc tatggctaaa      420
tctagacaag ctgcttgggg cagttccctt cgcgaacttt acacttttc cactgtcgaa      480 gattttgggg ggtaagttat ttcatattcc ctcggttcca atttaggtta cagtctttcc     540
tttttagtca acttttagtc tccttaaatg atatatttct atatttagta ataatttaat     600
atttatagtg acacaaatgt atcactcatt ttagatgaat ttttttttc ttaaactccg      660 taccaaatca aacactacta atgtaaattg ggacgaagcg agtattatat ttcgtgttaa     720
gctgttgtgt tctttggttg taaataaatc atggggtttt attttactgt tcaagaattt    780
tgtgggtgct gtaggatttt gttgaattat ggttttgaat agctcctgaa tatcttgcct    840
tcatataggg aaaattgggt aaaatcttca attttatgtg acactaattc tgttaaaaaa   900 aacacccttta tatttcgaa ataatttaa ctttaaactt ctcattttac tgctaatgtg     960
atgatttgta gtcacacaaa tgtctatctt gttttaaaaa ttttatttt ccttattaaa    1020 ctccatgctc agtcaaataa tgggtctatt ggaaacagtc tctctatcct cacaaggtag   1080
gagtaaggtc tgcttacaca ctaccctcct cagaccccac ggtatgggat aatactggtt   1140
atcttgttgt tgttgctaag tcaaacaaca ttacataaat tgggacggag ggactatctt   1200
gtttgatttt cagcttaagg aactttttgtt tcacaattat cagatttttc ctgtccttgc   1260
attttaagtt aaagcagcaa cgaggggcaa tcttactttg gagtgcccga attggtttga   1320
gcttaaattt atgcaagttg tattagtacc tacattgctt tgttgatgct gttgtaatgt   1380
gtaactgact tttccagttt gttacttaaa aaaggaatt ttttctctca gttacttacc   1440 aatttttagtt ttggttcatg gatcgaacta attacattta actttcaatg aatagatata 1500
```

```
tcctctttgg tggttggaag acagatagag aattatctgg tgtaaagtag gaaagtgcaa    1560
atatgaacag agattgagac attttggatg gggtaaagaa ttaccttaga agttctagga    1620
aagtaaaagt taaccttgtt aaaagtccgt tctcttcggt tatattgtcg ggtagttctt    1680
ttgcttcaaa tataagaaca tctgacctgt tagtcaaatg tccatattag caactaaaga    1740
tatgttgcaa acactatttt gagctaataa ggtagtggat aatgctttgg tcttagtttt    1800
ctctcctaag caggatatta tagttactat tttccaagta tcaattacac ttttcttaaa    1860
tgcacatata agagcatggt catgtgtatt tcatataggg ctgtcaaatt tggcccaagc    1920
cccaatgacc tgcccaacac gcccaaggtt gggctgtttg ttgacccgcc catttattga    1980
actcaaccca acttgaccca acccattaaa agttgggctg attttagcc caaattgatc     2040
catgagtaac tttgccagaa taacttagaa ataattcttt tctgtttgat atgttatata    2100
tggccataag aaagaaaaa gtcttattta gtattataca attcataaga aaacaacaca     2160
tattaattaa agtttggtaa gagttggacg ggttaggcta tgacccaaat tttagcccat    2220
cttgacccaa ccaatctcag cccaagtaat ttttgggcgg atcagtgacc cgcccatttg    2280
acaccataag ttcatacgtg tgacgtctct acgtgcattt gtcttcatat accaagctga    2340
ttattcattt aaaaagataa agatatctgc ttttctattc cttaattagg ctaagattac    2400
actaatctcc cctctagatt gatgagacta aacgtagctg cagaccagta tttcaatgtc    2460
attcttggat ctttatttaa gtcgtccgtt ttgagttagg tggtgatgat ttgaaatttg    2520
tgtctgcctt agatgcatgt tgtgttgctc ggatgggggc gcgggtatcc cataatggtg    2580
cagatctaaa ggtcggattt gtcatcacat aaatttagg attcgaggat atgaattcaa     2640
ctacggttac gggtgctggg atacaaccaa taatgtatg ttactacata tataagtata     2700
tatttcgatt aattaaagtt atcaaactaa atctaataat tttttcttat aaaatataaa    2760
cacgtaatcc ggtgtggatt ccacacccat gtcgtgttga tacgggtgcg caaagatt     2820
tgaagagtcc gcgcaactta ggatgcatgc accttgtttg gtgagttctt tatcagtcta    2880
atttctcaag gcacttgagt tattgtgcaa cttggactat gtcatgccta ttttgatatt    2940
ctgcatcttg gattagatgt tttcaaatgc tattatcctg ttagctttg atgaaatcct     3000
tgaaccatgt tgcttaaatt ctgcaaacag tgtttacaat aatatcaacc acccaagcaa    3060
gttagttgtg ggagcagact ttcattgttt taagcataaa attgagccaa agtgggaaga    3120
tcctgtatgt gcgaatggag ggaattggac aatgagcttt agtaagggta aatctgatac    3180
cagctggcta tacacggtat gctgaggata ttttaatcca gttcttaatg ttagggcgca    3240
gtctcgtaaa gttatttcc cctttgatat tatttcaact cttattttct catttgggat     3300
tattgtagct gctggcaatg attggacatc aattcgatca tggagaggaa atttgtggag    3360
cagtagttag cgtccgaaat aagggggata aaatagcttt atggaccaag aatgctgcaa    3420
atgaaacagc tcaggtaatt tactttttac caatgaaata gcctatttat attactccct    3480
ttgttccaat ttatgtgatg catttttcttt ttttgtccgt ccccaaaaga atgatatctt    3540
tctatattta ggaacaattt aactttgaac tttcgatttt accttaatg agacaattta    3600
cagccacaca tctatagctt gttttaccac aagtatcaaa agtcattctt tctttcttaa    3660
actccgtgcc cagtcaaaga gaaaaaatag atcgagggag tgcttttat ttttgacgtc     3720
aatgactagg tttgtcattt tcgtggacca agtgggcaga caattttgtt gtgtgcatat    3780
gtggtgctga tgtttattca agaaatacat catctaaacc atcttgtgat gccatttaac    3840
aataatgcgc aagataacaa gggtgtggcc tagtgatcaa tgaagtgggt tgagaaccat    3900
```

-continued

```
gaggtctcaa gttcaaatcc caatggaggc aaaaacacta gatgatttct tcctgtttgt    3960
ccaagcttgg tggacagaat tactcggtgc ctctgctggt gggaggtagt aagtaacccg    4020
tggaatagtc gaggtgcgcg caagttggca tggacactag ggttataaaa agaataataa    4080
taataatgat aatgattatg tcagctacta ttagttttga tgtgtgcgtg cgtgtgtgta    4140
tatattagtt tcattcctga cataacttct tttgacaact agaaactgat gtatagtacc    4200
gtatgatgta acattgggga tattagaagt tagaggggac gccatcagat atatataggc    4260
atatagtaca gttgtcaaac ttttttagctt ttgatagtga gttactttca tgaaaagctg    4320
gaagccaaaa agaaatatgc taatttgtct gcgataaatt attgtttcat ggcaattga    4380
gttatgtgaa gcttggacaa agagaactta tagagtaaaa gatattgttg aggactggtc    4440
caggtgtagg atgttatttc tgtgaagcag tgatttcgtt gtcaaatagt ctgttgcatt    4500
cctgcttgat atgtcgttac taattattta gtgttaggag attctggcat cattcagccg    4560
gttcgaaaag tctttgcaat tctttatccc aaaggttaag taattttttt tgtgtaccat    4620
ctggtatctg gtactcactg gccccagtaa tcggaattcg tgccacgtta gggcccctta    4680
aaaggggaag cgctccctat catatatttc tccattcata gggctcgaac ccgagacctt    4740
tggttaaggg catagggaat cccttggtgg ttccaagggt taagtattat tatatacttg    4800
ataaaatacc tttttctgtc aaccccttc ccgtagtttt tttcctccaa tatatagagg    4860
tcgaccgtcg acgttccccg attccccctt ttttgatggc ctcattcatt tgaagtacca    4920
ggccgtttta gtctaatttc gcaagtggat ccccttttgc gcgtcattga aaatattgaa    4980
tcctttcagc tgtttaacgg ttcatcaatt tttgctttaa tgcttattgt tagcctttgt    5040
ttctatatcg ttgtaactac acttaacatc atgcttgtcc catctcctga aacttctctc    5100
tgcaggttag cattggtaag caatggaagg agtttctgga ttacagcaac tcgattggct    5160
tcatatttca tgtatgacat cttatttatg gtatgccttg aaatcagttt ctcataattt    5220
gctactcata aagaatcatc ttcttttgca aattgcagga cgactcaatg aggctcggca    5280
gaggtgccaa gaatcgttat acagtatagt tttcttgcta caatggggga atgcaagaaa    5340
cagaatctgg actggaaagt ttatagacat tagctctgtt tgtacaatca tctatcatat    5400
gaaaggctgc cacttgacag tttaagtacc tttgttttag tgtttgtact tttaatcgaa    5460
gaaactcgtt tggttttgaa ttaatgcctt aacaataaac tttagtgctg tctctttttc    5520
taacaacttg ttttaacaat atcgtttcat gatgtattat atagtataat attgtattgt    5580
gctgtgtcgt tttgatgtat acaacgtttg gatagattgt attgtttttt gtcatttcat    5640
gatgtcatgc accaataata tgaagaacaa acttgcaata ttataaagaa aaagtaaggt    5700
gcgcggtaga attattatat gaaaggtat ggtaaataat aaaatagcat tatttaatta    5760
tatcgaagcg caagatgaga aaaaaataag ggaatgaagc gatcacacca aatcagtcgt    5820
tccataaagt agaattttc gatatgatat agcaataaaa tttaagtagc aaccaaaaca    5880
aacatcagat ttaaagtaac aatacaatac aataggtaac aaccatccaa acaagctgta    5940
aaagaataaa atctaagttt ggcatttttc gttgttattt tttctccaca acttatatac    6000
```

<210> SEQ ID NO 4
<211> LENGTH: 1016
<212> TYPE: DNA
<213> ORGANISM: Nicotiana tabacum

<400> SEQUENCE: 4

```
cccttttcct actaaaatct ataggtaaaa gcaagcaaag tacatagaaa acacacgaaa       60
atggcagagg aatctgagaa attgcgggta gatgaagtag aagtagccga cgatggacct      120
gaagaaggag aaatcgtggg ggaatcagat gatacggcgt cgtatttgag caaagaaatc      180
aaagctaagc acctgttgga gaattcttgg acttttggt atgataaaaa tacgaaatct       240
agacaagctg cttggggtag cttccttcgc gaagtttaca cttttccac tatcgaagat       300 ttttggggtg cttacaataa tatcaaccac ccaagcaagt tagttacggg agcagacttt      360
cattgtttta agcataaaat tgagccaaag tgggaggatc ctgtatgtgc gaatggaggg      420
aagtggacaa tgagctttag taagggtaaa tctgatacca gctggctata cacgctgctt      480
gcaatgattg gacatcaatt cgatcatgga gatgaaattt gtggagcagt agttaatgtc      540
cgaggtaagg aggataaaat agctttatgg accaagaatg ctgcaaatga acagctcag       600 gttagcattg gtaagcaatg gaaggagttt ctggattaca gcgactcgat tgacttcata      660
tttcatgaag acgcagagaa gcacggcaga ggtgccaaga atcgttatac agtatagttt      720
tcttgctaca atgggggaat gcaagaaaca gaatctggac tggaaagttt atagacatta      780
gctctgtttg tacaatcatc tatcatatga taagctgcca cttgacagtt ttagtcctgc      840
ctcttttcct aacaacttgt ttgaatagtt gttatgtatc gttttcataa tgtatcatat      900
cgtattgtat tgtattgttt tgatgtatca aaacaaatat tgcatttaaa gtaacaatac      960
gatatcatac aataggtaac aaccatccaa acaagatgta aagaataaaa atctaa         1016
```

<210> SEQ ID NO 5
<211> LENGTH: 218
<212> TYPE: PRT
<213> ORGANISM: Nicotiana tabacum

<400> SEQUENCE: 5

```
Met Ala Glu Glu Ser Glu Lys Leu Arg Val Asp Val Glu Val Ala
1               5                   10                  15

Asp Asp Gly Pro Glu Gly Glu Ile Val Gly Glu Ser Asp Asp Thr
                20                  25                  30

Ala Ser Tyr Leu Ser Lys Glu Ile Lys Ala Lys His Leu Leu Glu Asn
            35                  40                  45

Ser Trp Thr Phe Trp Tyr Asp Lys Asn Thr Lys Ser Arg Gln Ala Ala
        50                  55                  60

Trp Gly Ser Phe Leu Arg Glu Val Tyr Thr Phe Ser Thr Ile Glu Asp
65                  70                  75                  80

Phe Trp Gly Ala Tyr Asn Asn Ile Asn His Pro Ser Lys Leu Val Thr
                85                  90                  95

Gly Ala Asp Phe His Cys Phe Lys His Lys Ile Glu Pro Lys Trp Glu
            100                 105                 110

Asp Pro Val Cys Ala Asn Gly Gly Lys Trp Thr Met Ser Phe Ser Lys
        115                 120                 125

Gly Lys Ser Asp Thr Ser Trp Leu Tyr Thr Leu Leu Ala Met Ile Gly
    130                 135                 140

His Gln Phe Asp His Gly Asp Glu Ile Cys Gly Ala Val Val Asn Val
145                 150                 155                 160

Arg Gly Lys Glu Asp Lys Ile Ala Leu Trp Thr Lys Asn Ala Ala Asn
                165                 170                 175

Glu Thr Ala Gln Val Ser Ile Gly Lys Gln Trp Lys Glu Phe Leu Asp
            180                 185                 190

Tyr Ser Asp Ser Ile Asp Phe Ile Phe His Glu Asp Ala Glu Lys His
```

```
               195                 200                 205
Gly Arg Gly Ala Lys Asn Arg Tyr Thr Val
    210                 215

<210> SEQ ID NO 6
<211> LENGTH: 8039
<212> TYPE: DNA
<213> ORGANISM: Nicotiana tabacum

<400> SEQUENCE: 6
cggttaatta ctcttaacgg tttggcttaa cggttatcga tttttaaatg tattaatccg     60
ctagccaccc gataagatat cgggtggatt ggtatcggtt tagctcttat cgggcggttt    120
atcggcctaa tgcaatctat attgcgtgca ttaactattt gctgaccgcc tagcatacaa    180
attcagaata gaaaattaca cattgagtcc agacatacat atctgttaac gcctacataa    240
gaatgatgta gtgtgtcatg tgttgtaatt gtaggctaca ttacatctca aagcagacta    300
catatgagtc cagacataca tgtctgttaa cgcctaccat aaatcccaa agcagactat    360 attacatgag tccagacata catatgtttg ttaacgccta tcatattaat tcagaatagg    420
aaattccagt ctatattcaa agtgagtcca gaatacatat ttcaaaatga ttaatccata    480
agtaagcagt ctacacagaa atgtttggcc tgcagctaac acctaacaat gcttgagttt    540
ctgcaacttc aaagttcaaa caacagcttc aaatttctaa cttaaactct caaccaggca    600
tttcacgcta tcattaac catacaaaca acaccgagca aaagacagtt atgtatagaa    660
atagggatga ttataagcag taaataattt acaggaaacg caaatgcgct ctttccccag    720
aacataattc aagacagtac tatcgtcaat attgtgggat aaaagttgtg gcacaacact    780
attgttcttc tattaaacat aaacaacatg cattagttta aaaaaacaaa agcagaggtg    840
aaccatagat agcagcttaa acaatcttgt tgtagggtgg gagaataagc ttagctaata    900
gctggaagaa gtggaagaag tggaagggtt tttgatattt aatatatata ttcttaacgg    960
gttaacggat tatccgttaa gaaaattgaa taatccgccc ccaaaccgat aagccgttaa   1020
taaaaaaatt ttaatctgtt ccccgtccgt taaaccgtta acccgatacc aataagccat   1080
taagcttcga tttcggttcg gttttcggtt tcggttcggt tttgaatacc cctagttaca   1140
agtccataaa atagatacat ttggaaactt tagccactaa tattccaccg ccttggataa   1200
agattatttt acagtccaaa cttaagggac tattttcaa tgactttga gtctgtgact   1260 atttttctat tacaagtcca aaaaaatcga tattttgaa atttaggcac taatattcca   1320
ctgtctcaga taaaaattgt tttaagttac ggtccaaact taagggacta ttttttactt   1380
ttgaatttga aactatttt taattactag ttcaaaaata gctattttt ttttttaact   1440 ttaaccacta atattaaatg atactagata gccactctaa agactgctat caatgaatta   1500
gccagtgtat tcgaattttt aatttttcag gtcaaatttt tagaaaaaaa atgttgagaa   1560
ttatccttac ttttagttt aaaatttcag tataaaataa ataatgacta atttctaaat   1620
atcatcaaaa ataatcttg gataaataag ttacactcca attgaggaac aggaaagtct   1680
tgaaccaaag aagaactaca agtaccctt tcctactaaa atctatagct aaaagcaagc   1740
aaagtacatc gaaaacacac gaaatggca gaggaatctg agaaattgcg ggtagatgaa   1800
gtagaagtag ccgacgatgg acctgaagaa ggagaaatcg tgggggaatc agatgatacg   1860
gcgtcgtatt tgagcaaaga aatcaaagct aagcacctgt tggagaattc ttggactttt   1920
tggtatgata aaaatacgaa atctagacaa gctgcttggg gtagcttcct tcgcgaagtt   1980
```

```
tacactttttt ccactatcga agattttttgg gggtaagcct tttcatattc cctctgttcc    2040
aatttagata acagtctttc cttttttagta tccttaaaat tatatctttc tatatttagt    2100
aataatttag ttttaaaata ttattttacc cttaatgtga tttatagcca cacaaatgta    2160
tcactcattt tagatgaaaa aaaatccttt ttccccccctt aaaactccgt gccgaatcaa    2220
acactagtca tgttaattgg gacggagcga gtattatatt tcgtgttagg ttgttgtgtt    2280
ctttggttgt aagtaaatca tggggttttta ctgttcaaga attttgtggg tgctatagga    2340
ttttgttgaa ttatggtttt gaatagctcc tgaatatctg ccttcatata ggggaaattg    2400
gctgaaatct tcaattttat gtgacactaa atctgttaaa aaaaaagaca cctttatata    2460
tttcgaaata ataagtttaa acttctcatt gtactgttca tgagatgatt tgtagccaca    2520
caaatgtcta tcttgtttta aagttttttat ttttccttat taaacttcat gctcagtcaa    2580
acaatgggtc tattggaaat aatttctcta tcctcacaag gtagaggtaa ggtctgcgta    2640
cacactactc tccgtatacc ccacggtgtg ggataatact gggtatgttg ttgttgttgt    2700
tgttgctcag tcaaacaaca ttacataaat tgggacggag ggactatctt gtttgatttt    2760
cagcttaagg aacttttgtt tcacaattat cagattttttc ctgtccttgc atttttttgtt    2820 accttccttg gtgttcagtt aatgcagcaa cgaggggcaa tcttactttg gagtgcctga    2880
attggtttga gcttaaattt atgcaagttg tattagtacc tacattgctt tgttgatgct    2940
gttgtaatgt gtaactgact tttccagtta gttactttaa aaaatggaat ttttttctctc    3000 agttacttac caattttagt tttggttaat ggatcgaact cattacattt aactttcaat    3060
gaatagatat atcctctttg gtggttggaa gacagagaat tatctggtgt aaagtaggga    3120
aagtgcaaat atgaaaagag attgagacat tttggatggg gtaaagaatg accctagaag    3180
ttctaggaaa gtaaaagtta cttgttaaaa gttcattctc ttcggttcac caccttgtct    3240
aggaatcact tcaattcggt tatattgtcg ggtagttctt ttgcttccaa tataagaaca    3300
tctgacctgt tagtcaaata tccatattag caactaagga tatgttgcag gcactatttt    3360
gagctaataa ggtagtggat aatgctttgg ttttagtttt ctctcctaag caggatatta    3420
tagttactat tttccaagta ccaattatta cttttcttaa atgcacatat aaagggctgt    3480
caaatttagc ccaagcccca atgacccgcc caacacgctc aaggttgggc tgtttattga    3540
cccgcccatt tgttgaactc aacccaaccc atctcaaccc ttttaaagtt gtactgatat    3600
ttagcccaaa ttgatccatg agtaactttg ccagaatatc ttaaaaataa ttcttttttg    3660
tttgatatgt tatatatggc cataagaaaa gaaaaagtct tatttagtat tatacaattc    3720
ataagaaaac aacacatatt aattaaagtt tggtaagagt tgggcgggtt gggctatgac    3780 ccaaattttta gcccatcttg gcccaaccaa tctcagccca agtaattttt gggcggatca    3840
atgacccgct catttattaa ctcagcccat tttgacccgc ccatttgaca ccctaagttc    3900
ttacctgtga cgtctctatg tgcatttgtc ttcatatacc aagctgatta ttcatttaaa    3960
aagataaaga tatctgcttt tctattcctt aattaggcta aaattacact gatctcccct    4020
ctagattgat gagactaaac gtagctgcag accagtattt caatgtcatt cttggttatt    4080
taagttgtct ggtttgagtt aggtggtgat gatttgaaat tggtgtctgc cttagatgca    4140
tgttgtgttg ctcggatgcg ggcgcgggta taccatagtg gtgcagatct aaaggccgga    4200
tctgtcatca cataaatttt aggattcggg gatatgaatt caagtacggg tacaggtgtt    4260
gggatacaac caataaatgt atattactac atatataagt atatatttcg attaattaaa    4320
gttattaaac taaatctaat aattcttttta ataaactata aacacctaat ccggtgtgga    4380
```

| | |
|---|---|
| ttccacaccc acacccatgt cgtgttgata cgggtgcggc aaagattttg aagagtccgc | 4440 |
| gcaacatagg atgcgtgcac cttgtttggt gagttcttta tcagtctaat ttctcaaggc | 4500 |
| acttgagtta ttgtacaact tggactatgt catgcctatt ttgatattct gcatcttgga | 4560 |
| ttagatgttt tcaaatgcta ttatcctgtt agctcttgat gaaatccttg aaccatctcg | 4620 |
| cttaaattct gcaaacagtg tttacaataa tatcaaccac ccaagcaagt tagttacggg | 4680 |
| agcagacttt cattgtttta agcataaaat tgagccaaag tgggaagatc ctgtatgtgc | 4740 |
| gaatggaggg aagtggacaa tgagctttag taagggtaaa tctgatacca gctggctata | 4800 |
| cacggtatgc tgaggatatt ttaatccact tcttaatgtt agggcgcact ctcgtaaagt | 4860 |
| ttttccccett cgatattatt tcaactctta ttttctcatt tgggattatt gtagctgctg | 4920 |
| gcaatgattg gacatcaatt cgatcatgga gatgaaattt gtggagcagt agttaatgtc | 4980 |
| cgaggtaagg aggataaaat agctttatgg accaagaatg ctgcaaatga aacagctcag | 5040 |
| gtaatttgct tgttaccaat gaaatagcct atttatatta ctccctttgt tccaatttat | 5100 |
| gtgatgcact ttcttttttt gtccgtcctc aaaagaatga tatttttcta tatttaggaa | 5160 |
| caatttaact ttgaactttc tattttacct ttaatgagat gatttacagc cacacatatc | 5220 |
| tatagcttgt tttaccacaa gtatcaaaag ttattatttc tttcttaaac tccgtgccca | 5280 |
| gtcaatgaga aaaaatggg acggagggag tacttttat tttgacgtc aatgaccagg | 5340 |
| tttgtcattt tcgtggacca agcgggcaga caattttgtt gtgtgcatat gtggtgctga | 5400 |
| tgtttattca agaaatacat catctaaacc atcttgtgat gccatttaac aataatgcat | 5460 |
| aagataacga ggttgtggcc tagtgatcaa tgaagtggat tgagaaccat gaggtctcaa | 5520 |
| gttcaaatcc caatggaggc aaaagcacta gatgatttct ttctgtttat ccaagccttg | 5580 |
| gtgggtagaa ttacccagta cctgtgctgg tgagaggtag taggtatccc gtggaatagt | 5640 |
| cgaggtacgc tacgcacaag ctggagttga caccccggtt ataaaatat taataatagt | 5700 |
| aataatgatt atgtcggcta ctattagttt tgatgtgtgt atgttttttt cttttgtgt | 5760 |
| gtgtgtatta gtttcattcc tgacataact tcttttgaca actagaaact gatgtatagt | 5820 |
| accctatgac atacatgtaa cattggggat attagaagtt agagggggaag tcatcagata | 5880 |
| tataggcata tagcacagtt gtcaaacttt ttagcttttg atagtgaatt actttcatga | 5940 |
| aaagctggaa gcaaaagaaa tatgcttatg gatgaagcaa agtgccaatt tgtctgcgat | 6000 |
| aaattattgc ttcattggca attgagttat gtgaagcttg gatgaagaga acttacagag | 6060 |
| gaaaaaataa tgatgcggac tggtccaggt gtaggatgtt atttctgtga agcagtgata | 6120 |
| ttgttgtcaa atagtctgtt gcattcctgc ttgatatgtc gttactaagt atttagtgtt | 6180 |
| attaggagat tttggcatca ttccaagatc tgcagccggt tcgaaaagtc tttgcaattc | 6240 |
| ttttatccca aaggttaagt atttcttttt ttggtgtacc atctggtacc aggtactcac | 6300 |
| tggcccgact aatcggaatt cgtgccgcat agggacttct taaagggaa acgctccta | 6360 |
| ttatatattt ctccattcat agggctcgaa cccgagacct ctggttaagg cataggaa | 6420 |
| tcccttggtg gtcccaaggg ttaagtttta ttttatgttt gataaaatac ctttttctgt | 6480 |
| caccccttc ccttattctg ctagaatata tagtggtcga cgttccccga ttccccettt | 6540 |
| tttgatggcc tcatccattt gaaataccag gccgttttag tctaatttcg caagtggatc | 6600 |
| ccctttttgtg catcattgac aatattgaat cctttcaact attaccagtt tgttaatttt | 6660 |
| tatgttaata gtacttgaca tcatgttttg ggtttaataa ataaccatag ttgaaaacac | 6720 |

```
cgaaaatcct ttcaccagag aaagtctttc agatttttaa catggaaatc aagtttctga      6780
agttcattgt tagattaaaa atcaatagaa ttgaatacaa gaagtggaaa aaaacagaga      6840
acaagacaac aagtcgtgga actgcatttt cgcgggaaat aaactaacca attctcacca      6900
ggttctcttg aaacttctct ctgcaggtta gcattggtaa gcaatggaag gagtttctgg      6960
attacagcga ctcgattgac ttcatatttc atgtatggca tcttatttat ggtatgcctt      7020
gaaatcagtt tctcataatt tgctaaactc atgtcttttg caggaagacg cagagaggca      7080
cggcagaggt gccaagaatc gttatacagt gtagttttct tgctacaatg ggggaatgca      7140
agaaacagaa tctggactgg aaagtttata gacattagct ctgtttgtac aatcatctat      7200
catatgataa gctgccactt gacagtttta gtcctgcctc tttttctaac aacttgtttg      7260
aatagttgtt atgtatcgtt ttcataatgt atcatatcgt attgtattgt atcgttttga      7320
tgtatcaaaa caaatattgt atttaaagta acaatacgat accatacaat aggtaacaac      7380
catccaaaca agatgtaaaa gaataaaatc taagttggca ttttttcgttt ttatttttttc      7440 tccacaactt atatacgagc ttcaactcac caaaaaaatc gcttcaatttt ttatcacaat      7500 tgaaaaatgg catcctcaac aaaccatatt catcaatttg tcataacttt taacatatta      7560
tttttttcac tttaattcac ccaacaacgt ttaaatatgt attgataaat atgaatgtca      7620
ctctcaaatc agttcttaac acaaatcttt ttaataccct gctaataggt gaaaagatgt      7680
ttcaaatttg acacacaata gactaaagta gataagcaaa aaagtatagg ctaatttttat      7740 aattatggta taaacaactt tgggattact aattcaggaa ttacaaattc tatcaaaacg      7800
tgtgataaac taatcctata ttttattgtg gtattataat tcccatctcg gatgaagact      7860
gatttaagtt atagtccaaa cttaagggcc aaaaaaaga agaagaaac ttaagggact      7920 aatttggttg tctaaagttg gaaaaaaagt cttagaacga aaaactatt taaatcccca      7980 tttcccacca aagccaagta cataacacca aaatggcagg ggaagcaaaa acgtcggag      8039

<210> SEQ ID NO 7
<211> LENGTH: 867
<212> TYPE: DNA
<213> ORGANISM: Nicotiana tabacum

<400> SEQUENCE: 7
tccattacgc ctctccgttc gctaaaaatc gacacaaagg gaggagagga ttttttgagg        60
caaaaatcaa tggccactga agcaccgata gaggcgacgg aggttccgcc ggcgtcagcg       120
acggagacgg tggcgaagca gccacataag ctagagagga gatggacatt ctggttcgat       180
aatcaatcta agccgaaaca aggagccgct tggggaagtt ctcttcgaaa agcttatact       240
ttcgaaactg ttgaggaatt ctggagttta tatgatcaga tattcaagcc cagcaagttg       300
actgctaatg cggactttca tttgttcaaa gctgggattg agcccaaatg gaagatcct       360 gagtgtgcta gtggtggcaa gtggactgtt acgagcagca gaaaggctaa tcttgagact       420
atgtggcttg aaactctgat ggcattggtc ggtgagcagt ttgatgagtc agaggagata       480
tgtggagtgg ttgccagtgt acgtcggagt caggataaac tttccttatg gactaagact       540
gcctccaatg aagcaattca gatgagcatt ggtaggaagt ggaaggagat cattgatgct       600
gaaaaaatat cctatagttt ccatgatgac tctaaaaggg aaaggtcagc taagagtcga       660
tatactgtgt gaattccttt attgtgtggg attgacactg gtccctagat tttccaatac       720
tgaaaattgt acgattagca cagttttgcg cttgtctgct gcaaaatttt gattttcttt       780
ttaaatttat tcgcacttga tatggatctt tggatgtatt gtgttaaaga ttttgtttgg       840
```
ttctgtgtta aaaaaaaaaa aaaaaaa          867

<210> SEQ ID NO 8
<211> LENGTH: 200
<212> TYPE: PRT
<213> ORGANISM: Nicotiana tabacum

<400> SEQUENCE: 8

Met Ala Thr Glu Ala Pro Ile Glu Ala Thr Glu Val Pro Pro Ala Ser
1               5                   10                  15

Ala Thr Glu Thr Val Ala Lys Gln Pro His Lys Leu Glu Arg Arg Trp
            20                  25                  30

Thr Phe Trp Phe Asp Asn Gln Ser Lys Pro Lys Gln Gly Ala Ala Trp
        35                  40                  45

Gly Ser Ser Leu Arg Lys Ala Tyr Thr Phe Glu Thr Val Glu Glu Phe
    50                  55                  60

Trp Ser Leu Tyr Asp Gln Ile Phe Lys Pro Ser Lys Leu Thr Ala Asn
65                  70                  75                  80

Ala Asp Phe His Leu Phe Lys Ala Gly Ile Glu Pro Lys Trp Glu Asp
                85                  90                  95

Pro Glu Cys Ala Ser Gly Gly Lys Trp Thr Val Thr Ser Arg Lys
            100                 105                 110

Ala Asn Leu Glu Thr Met Trp Leu Glu Thr Leu Met Ala Leu Val Gly
        115                 120                 125

Glu Gln Phe Asp Glu Ser Glu Glu Ile Cys Gly Val Val Ala Ser Val
    130                 135                 140

Arg Arg Ser Gln Asp Lys Leu Ser Leu Trp Thr Lys Thr Ala Ser Asn
145                 150                 155                 160

Glu Ala Ile Gln Met Ser Ile Gly Arg Lys Trp Lys Glu Ile Ile Asp
                165                 170                 175

Ala Glu Lys Ile Ser Tyr Ser Phe His Asp Asp Ser Lys Arg Glu Arg
            180                 185                 190

Ser Ala Lys Ser Arg Tyr Thr Val
        195                 200

<210> SEQ ID NO 9
<211> LENGTH: 5140
<212> TYPE: DNA
<213> ORGANISM: Nicotiana tabacum
<220> FEATURE:
<221> NAME/KEY: misc_feature
<222> LOCATION: (4151)..(4151)
<223> OTHER INFORMATION: n is a, c, g, or t

<400> SEQUENCE: 9
cacccgcggt tggaataccg gcccagtcta tcaatatggg cctaaacgtt gtaagacaag      60
tcccactaat atcaatcaac tgggctacca taaataattc cagctccata ccctgattct     120
cttccaacaa ttccattacg cctctccgtt cgctaaaaat cgacacaaag ggaggagagg     180
attttttgag gcaaaaatca atggccactg aagcaccgat agaggcgacg gaggttccgc     240
cggcgtcagc gacggagacg gtgggcgaagc agccacataa gctagagagg agatggacat     300
tctggttcga taatcaatct aagccgaaac aaggagccgc ttggggaagt tctcttcgaa     360
aagcttatac tttcgaaact gttgaggaat tctggaggta tacaaaaaat acaaaacacg     420
agatctcttt tagattcttc tggttatatt tttttgccc taatttagat tttttaatga     480
aattttatca attgtttttat gaattgggta atagcacttt tgattcataa gttattgaga     540

```
aattctgatt tgttccctg tagcatttaa ctaagcatat ttaaccttt attcattaaa      600 atgtgtgttt tttggtccca ttacatagga aatatgttt acatttagat tagtttaga       660 actatattac ccttaaatat gaagtagtag tacaaattta acataacata tgggtactta     720
aatgatttaa aagttaatag ttcgttaaag tgggtagatt cacaaataga aggatgaaaa    780
gtgcacattt taattaattc aagtttaagt atgcataaac agatagcaca aggactataa    840
ctagaatatt tcaacattta agggtcaaaa agaacactct tccgtcctta attaattaag    900
atgctttcat gttgcaatgt tatgttgatg taagagtata tgaatatgtt accttcacaa   960
agagagagca catgtcttgg acctactttg tgctggaaac atattaaaaa ttatactttc    1020
tactacctgc tcgctcatat gaaactctgt tttgggagtt cgaaaaaata ttcaccatta    1080
cgttaattat ggagtattat ttatggaaaa gttccattaa gaatattgtc ctatgcatct    1140
tttgcaattt tcaagaatct aagtgcacct aaggggtgg gctagtggtc aatgaagtac     1200
gagaagaacc ttgagatctc aggttcaagt tccagcggag cgaaaaata gtaggtgatt     1260 tcttccaatt tgcctaagcc ttggtaggca gaatacccga taccaggtag caggtacacg   1320
gcagaagccg gacatcacgt cataaaaaaa tcaagaattt gaattattta acaatccaaa   1380
gcttgtgata tgttctctgt cacctaagt ttttaggtat caatttagta ttttctttaa    1440
ccaccactaa tataattact atacagtcaa gcattgtgct ataaaaccaa acagtgccat    1500
ttttatctta aatttcataa ttttccatgt aatgaattta ctgctgcaat ttatccatag   1560
tttggatgtt gtgtggcttt atttttaattc attaatgaga tattactgtt tagaaagtgt  1620
aatagttcca ctatgtggga ttatactggg tttgttgttg taaagtataa tagttggata   1680
gaagctgctt ttaaatgtca attgaagtgt tagatctttc tcttttcagt ttatatgatc   1740
agatattcaa gcccagcaag ttgactgcta atgcggactt tcatttgttc aaagctggga   1800
ttgagcccaa atgggaagat cctgagtgtg ctagtggtgg caagtggact gttacgagca   1860
gcagaaaggc taatcttgag actatgtggc ttgaaactgt aataaaatct tctctttact   1920
tttcttggtt tctgttcagt aggcaggatg tcatgaaagc attatgttga ttagttttcta  1980 gttaaagatg ctcacatgtt gtttgctcga tggaattctt ttgaatagct gatggcattg   2040
gtcggtgagc agtttgatga gtcagaggag atatgtggag tggttgccag tgtacgtcgg   2100
agtcaggata aacttttcctt atggactaag actgcctcca atgaagcaat tcaggttatt   2160
ggaattctca tgatgtagaa tagttactga actgaaaact gtgttatgtt ttaccctata   2220
tcataaatct gatatgaaat attatttaaa aagaatata ccagaatatg atcttttct    2280 taatgatgat gatatggccc atcttccctt ctaaaaaagg agctatctcc aattcttttt  2340
taaatgctga aaaggagag cgtatttatt tgagcactga attttgagaa caagggaagc   2400
atgcccttcc ccgttgtgac ccatggatgg aacactagat ctagttatta aatatcggtt   2460
aaaaccatca catgccttag ctaatcagtg gctgaaacta gtatttcttg gtagggaagt  2520
ccttgatatt tcctttaact tgtctctaac cggagttggc agatatgatg ttgtttttgt   2580
aatggtatga cctctaccat gtatttgttt tgaattttt ctttttgataa agtaaataat   2640 tttcttagtg atggggtgac cccgtataca agcctatacc aaaagtggaa gaacctacaa   2700
caaaatatgg ttgtcagtga aagaaaccaa tcatttatac acataaagac ctcatgggta   2760
caccaaaaag ctagaaacga gaggtcgttt tgcaatttt cgaaagcatt atcaacctct    2820
tcaaatactc tcatgttcct ctctttccat agaacccaca taatggctga tggggaaaca   2880
```

```
tcccatgccc tcggtcttct cttcctcctg aaggcccaag tatgcaacgc ctctttcatt    2940
gtgcacgcat cacgcattat attcgaaacc aatttaggac caccgaccgc aactgtccag    3000
ccacatgaca acgcaacaag agatggtttt acacctttgc ccgcacaact gtacaagatg    3060
caacaactaa ccatttgttc ttattatggg ccttttgttg ccgttttgca ttaggccttc    3120
gctaaaaaca ctttgaccct ggctcatatc ccttgaactg atctatggac atataggcat    3180
ctgaatgtgc ttcattttca tcttctaaag taccctcgtg cttgaaatcg aaatttgctg    3240
tgtggtgatg ttctatagat catagatggt aagaaattcc aaaagggtgt gaagtttgca    3300
aaggtgttcc ctagaagtct gtactcatca gcttctcatc taaacacagg aatgtggtta    3360
ttttgaaggg ttttacttgt cacgaagtgg atgcaggacc ccctcccccc caacacacac    3420
acacaacaca cccacccacc caatatgtct tgtctccaa tttaattact taatgattat    3480
ggatttggga aaatggaaat atgctatctg gactttaagg ttgtactttg caatctttta    3540
acctttccga cttgaactgt ataatgaatt gataatgtta caacgacctt ttaacatttg    3600
tttagaaaaa agggcaactc ggtgcatgat gcatcccgcg tttacacaag atccggtgaa    3660
gagccgcaac actagtgcgt gtgatggaaa caactttact gttgctccaa gactccattt    3720 cacctttta acattttagt ttttttattt aagtttgggg gtgggaagag ggatttcaaa    3780
tggagacgtg tacactagaa agaactaact gaaaaaggac aaaggacaga taacctaata    3840
ctgtacctgg gacataaacc atttctctta tctttgcctt catgatttag tgatttttct    3900
cttttttctt ttccttgcga agttttcaca ttgcctctta aaatgtttaa aaactcgtca    3960
gggtggtaaa gtgcaatagg ccttttatac gaatgaaaag acaaagaaac agctaaactg    4020
aaatagtatt tcttcaatct cacctaacag tttcattcat ttacagtgta cctaattctg    4080
gttggtcttg tttaatacac cttctcctgt gtgtaccact aatgcacttg ctaaggatga    4140
tttaattccc nacacacaca cccacccacc cacacaaaag atgctggaaa atgtatcttt    4200
ctccctctga atatgcagct tggagtttta gacacaagtt cttgtatttc attcgttaag    4260
cactattcca tattatacta aaagcttata ttagacatgt tcatcttaca gtattgcaag    4320
acacaaggtt caatttaaat tccattacat tgctccacta ggtttccttt tttgtttatt    4380
gttgtgtgac tgcatgtgtt ttcctgcttt taacacatgt aacatgtctg gatatcaaca    4440
atcttcattc ctaacctttg ttttttggca tgatgctaca cttgatgcat tgttttcctg    4500
cttttaacac atgtaacatg tctggatatc aacaatcttc attcctaacc tttgtttttt    4560
ggcatgatgc tacacttgat gcattgtttt cctgctttta acacatgtaa cacgtctgga    4620
tatcaacaat cttcattcct aacctttgtt ttttggcatg atgctacact tgatgcattg    4680
tggtttcgca attatatata accggttggt tttatgctgc agatgagcat tggtaggaag    4740
tggaaggaga tcattgatgc tgaaaaaata tcctatagtt tccatgtaac ttcccttgcc    4800
gcttgccatt attgcaaagt caagtgtctt ttatctttcc tcctgttaat ttcttttcct    4860
ctcgtaatca accaatcttt tggtcgttgc aggatgactc taaaagggaa aggtcagcta    4920
agagtcgata tactgtgtga attcctttat tgtgtgggat tgacactggt ccctagattt    4980
tccaatactg aaaattgtac gattagcaca gttttgcgct tgtctgctgc aaaatttgaa    5040
ttttcttttt aaatttattc gcacttgata tggatctttg gatgtattgt gttaaagatt    5100
ttgtttggtt ctgtgttact tatctggagc ctgccccatg                         5140

<210> SEQ ID NO 10
<211> LENGTH: 805
```

```
<212> TYPE: DNA
<213> ORGANISM: Nicotiana tabacum

<400> SEQUENCE: 10
gacacaaaag ggagaggatt ttttgaggca aaatcaatgg ccactgaagc accgatagag      60
gcgacggagg ttctgccggc gccggatacg gtggagaagc agccgcataa gctagagagg     120
agatggacat tctggttcga taagccgaag caaggcgctg tttgggcaag tgctcttcga     180
aaagcctata ctttcgaaac tgttgaggaa ttctggagtt tatatgatca gatattcaag     240
cccagcaagt tgactgctaa tgcggacttt catttgttca agctgggat tgagcccaaa      300
tgggaagatc ctgagtgtgc caatggtggc aagtggactg tcacgagcag cagaaaggct     360
aatcttgaga ctatgtggct gaaactctg atggcattgg tgggtgagca atttgatgaa      420
tcagaagaga tatgtggagt ggttgccagt gttcgtcgga gtcaggataa actttccttg     480
tggactagga ctgcctccaa tgaagcagct cagatgagca ttggtaggaa gtggaaggag     540
atcatcgatg ctgaaaaaat atcctatagt ttccatgatg actctaaaaa ggaaaggtca     600
gttaagagtc gatatactgt gtgaattccc ttattgtgtg ggattgacac cggtccctaa     660
gtttactgaa aattgtacga ttagcattag tttgcgcttg tctgctgcaa attttgattt     720
tcttgaaatt tattcgtact tgatatgtat ctttggatgt attgtgttaa agattttgtt     780
tgcttctttg ttacttgaaa aaaaa                                           805

<210> SEQ ID NO 11
<211> LENGTH: 195
<212> TYPE: PRT
<213> ORGANISM: Nicotiana tabacum

<400> SEQUENCE: 11

Met Ala Thr Glu Ala Pro Ile Glu Ala Thr Glu Val Leu Pro Ala Pro
1               5                   10                  15

Asp Thr Val Glu Lys Gln Pro His Lys Leu Glu Arg Arg Trp Thr Phe
                20                  25                  30

Trp Phe Asp Lys Pro Lys Gln Gly Ala Val Trp Ala Ser Ala Leu Arg
            35                  40                  45

Lys Ala Tyr Thr Phe Glu Thr Val Glu Glu Phe Trp Ser Leu Tyr Asp
        50                  55                  60

Gln Ile Phe Lys Pro Ser Lys Leu Thr Ala Asn Ala Asp Phe His Leu
65                  70                  75                  80

Phe Lys Ala Gly Ile Glu Pro Lys Trp Glu Asp Pro Glu Cys Ala Asn
                85                  90                  95

Gly Gly Lys Trp Thr Val Thr Ser Ser Arg Lys Ala Asn Leu Glu Thr
            100                 105                 110

Met Trp Leu Glu Thr Leu Met Ala Leu Val Gly Glu Gln Phe Asp Glu
        115                 120                 125

Ser Glu Glu Ile Cys Gly Val Val Ala Ser Val Arg Arg Ser Gln Asp
    130                 135                 140

Lys Leu Ser Leu Trp Thr Arg Thr Ala Ser Asn Glu Ala Ala Gln Met
145                 150                 155                 160

Ser Ile Gly Arg Lys Trp Lys Glu Ile Ile Asp Ala Glu Lys Ile Ser
                165                 170                 175

Tyr Ser Phe His Asp Asp Ser Lys Lys Glu Arg Ser Val Lys Ser Arg
            180                 185                 190

Tyr Thr Val
        195
```

<210> SEQ ID NO 12
<211> LENGTH: 3620
<212> TYPE: DNA
<213> ORGANISM: Nicotiana tabacum

<400> SEQUENCE: 12

| | | | | | |
|---|---|---|---|---|---|
| acaacaaata | cccgaggtag | gattaccggc | ccagtctgtc | atcatatatg | gacctgaaca | 60 |
| ttgcaagatg | aggcccaata | atagcaatca | actgggccag | tataaataaa | attccagctc | 120 |
| cataacctga | ttttcttccc | aacaattcca | ttacgcctca | atcgacacaa | aagggagagg | 180 |
| atttttgag | gcaaaaatca | atggccactg | aagcaccgat | agaggcgacg | gaggttctgc | 240 |
| cggcgccgga | tacggtggag | aagcagccgc | ataagctaga | gaggagatgg | acattctggt | 300 |
| tcgataagcc | gaagcaaggc | gctgtttggg | caagtgctct | tcgaaaagcc | tatactttcg | 360 |
| aaactgttga | ggaattctgg | aggtatacaa | aaaatacaaa | acacgagatc | acttctagat | 420 |
| tcttctggtt | atatttattt | gccctaattt | agatctttaa | tgaaattttg | tcaattgttt | 480 |
| tattaattgg | gataatagca | cttttgatca | tcagttattg | ataaattcgg | attttgttcc | 540 |
| ttgtagcatt | caagtaagcc | tatttaacct | tgaattcatt | aaaatgtgtg | tttttggtcc | 600 |
| ctttacatag | gaaatatgtt | acatttagat | tagttttaga | actatattac | cctaaaataa | 660 |
| gaagtgctag | tacaaattta | acataacata | ggggtactta | aatgatattg | aaagttaaca | 720 |
| attcattaaa | gttgtgtaga | ttcacaaata | gaaggatcaa | aagtgcacat | tttaattaat | 780 |
| tcaaggttaa | gtatgcataa | gcagatagca | caaggactat | aactagaata | tgtcaatgtt | 840 |
| taagggacaa | aaagcacaat | cttccattct | taattagtta | agatgctttc | atgctgcaag | 900 |
| gttctatgtt | gatgtaagag | tatatgaata | tgttaccttc | acaaaagag | aacatatatc | 960 |
| ttggaccttc | tttgtgctgg | aaaacatatt | gaaaattata | ctttctactt | cctgcttata | 1020 |
| tgactctctg | ttttgggact | tcaggaattt | ttcaccatta | cactaattat | tgagtattat | 1080 |
| tatggaaaag | tttctttaag | aatattgttc | tatgcatctt | ttgcaatttt | caagaatcta | 1140 |
| actgcaacca | atgggtgtag | ctagtggtga | atgaagtggg | agaagaacct | tgaggtctcg | 1200 |
| ggttcaaatt | acagcggcag | tgaaaagaat | actagttccc | atttgcaggt | acccggcgga | 1260 |
| agctggatac | cgcatcattt | aaaaaaaacc | aagaatttga | attatttaac | aatccaaagc | 1320 |
| ttgtgatatg | ttctctataa | aactaacttt | ttagatatca | atttagtgtt | ttcttcaacc | 1380 |
| tccactaata | taattactgt | ccagtcaagc | agtgtgctat | aaaaccaaac | cgtgcatttt | 1440 |
| tatcttaaat | ttcataattt | ccccagtaat | ggattctacc | gctgcaattt | atccatactt | 1500 |
| gggatgttgt | gtggctttat | tttaattcat | tgacgagata | ttattattta | gaaagtgtaa | 1560 |
| tagttggata | gaagctgctt | ttaaatgcca | attgaagtgt | tagatctttc | tctttgcagt | 1620 |
| ttatatgatc | agatattcaa | gcccagcaag | ttgactgcta | atgcggactt | tcatttgttc | 1680 |
| aaagctggga | ttgagcccaa | atgggaagat | cctgagtgtg | ccaatggtgg | caagtggact | 1740 |
| gtcacgagca | gcagaaaggc | taatcttgag | actatgtggc | ttgaaactgt | aataaagtct | 1800 |
| tcccttttgct | tctgttggtt | tctgttcagt | aggcaggatg | tcatgaaagc | attatgttga | 1860 |
| ttaatttctt | gctaaagatg | ctcacatatt | gtttgctgga | tggatttctt | ttgggcagct | 1920 |
| gatggcattg | gtgggtgagc | aatttgatga | atcagaagag | atatgtggag | tggttgccag | 1980 |
| tgttcgtcgg | agtcaggata | aactttcctt | gtggactagg | actgcctcca | atgaagcagc | 2040 |
| tcaggttagt | ttggaattct | cgtggtgtca | aatagtatct | gaaattctga | actaaaaact | 2100 |

```
gtgttatttt ttccccatata tcctaaatct gatatgaaat attattaaaa aaaggatata    2160
ccagaatatt atcttttct taatgatgat ctgtcccatc tccaattttt ttgtaaacgc      2220
tgaaaaagga gagcagcttt atttgagcac cgaattttga gaacaagaaa agaatgccct    2280
tccccattgt gacccatgga tggagcacta gatctgttat tcaatatata atttaaatat    2340
caattaaaac catcacatac cctagctaat cagtggctga aattattatt tttcttggca    2400
gggaatcctt gatatttcct ttcacttatt ctctaaccat aattggcagc tatgacgttt    2460
ttatttattg taatggtata gcttttctct ggcatttgtt cagttttctt gataaagtaa    2520
ataattttat tagtgatggg gagaccccgt atacaagcct ataccaaaaa gtggagaacc    2580
tacaacagaa tacggttctc catgaaagaa atacacatag gtacctcatg ggtacatcaa    2640
aaagaaacta gacaagagat tgttttgcaa ttttactaaa tcattatcaa ccccttcaaa    2700
tgctctcatg ttcctttctt tccatataac ccacataatg gctgatgggg cgacatcaca    2760
tgccctcaat cttctgttcc tcctcctgaa ggcccaacta tgcaacacct ccttcattgt    2820
gcccgcatca cccattgtat tccaaaaaaa aagatgctgg aaaatgtatc ttttcccctc    2880
tgaacatgca gcttggagtt tgacataagt ttttgtattt cattctgtaa gcactgttcc    2940
agattatact aaaagcttat attagacatg ttcatcttac agtattgcaa tacacaaggt    3000
ttcaatttaa attcgattac atttctccac taggttccct ttttttgttta ttgttgtctg    3060 actgcgtata tttcctgctt ttgaccatgt aacctgtctg gatatcaaca atcttcactc    3120 ttaactttg ttttctggca tgttgctaca cttgatgctc catggttttg caatgatata    3180
tgactggttg gttttatgct gcagatgagc attggtagga agtggaagga gatcatcgat    3240
gctgaaaaaa tatcctatag tttccatgta acttctgttg ccccttacca ttattgcaaa    3300
atcaagtgtc ttttatcttt cctcctgtta attttttct ttcttaatca accttttctt    3360
tggttgttgc aggatgactc taaaaaggaa aggtcagtta agagtcgata tactgtgtga    3420
attcccttat tgtgtgggat tgacaccggt ccctaagttt actgaaaatt gtacgattag    3480
cattagtttg cgcttgtctg ctgcaaattt tgattttctt gaaatttatt cgtacttgat    3540
atgtatcttt ggatgtattg tgttaaagat tttgtttgct tctttgttac ttgtctaaag    3600
tgtgcctcat gtcttaattt                                                3620

<210> SEQ ID NO 13
<211> LENGTH: 339
<212> TYPE: DNA
<213> ORGANISM: Nicotiana tabacum

<400> SEQUENCE: 13
gcgggtagat gaagtagaag tagtcgacga tggacctgaa gaaggagaaa ttgtggatga      60
atctgatgat acggcgtcgt atttgggcaa agaaatcaaa cctaagcatc cattagagaa    120
ttcttggact ttttggtttg ataatccat ggctaaatct agacaagctg cttggggcag     180
ttcccttcgc gaactttaca ctttttccac tgtcgaagat ttttggggtg tttacaataa    240
tatcaaccac ccaagcaagt tagttgtggg agcagacttt cattgttttta agcataaaat    300 tgagccaaag tgggaagatc ctgtatgtgc gaatggagg                            339

<210> SEQ ID NO 14
<211> LENGTH: 313
<212> TYPE: DNA
<213> ORGANISM: Nicotiana tabacum

<400> SEQUENCE: 14
```

```
agaggcgacg gaggttccgc cggcgtcagc gacggagacg gtggcgaagc agccacataa    60
gctagagagg agatggacat tctggttcga taatcaatct aagccgaaac aaggagccgc   120
ttggggaagt tctcttcgaa aagcttatac tttcgaaact gttgaggaat tctggagttt   180
atatgatcag atattcaagc ccagcaagtt gactgctaat gcggactttc atttgttcaa   240
agctgggatt gagcccaaat gggaagatcc tgagtgtgct agtggtggca agtggactgt   300
tacgagcagc aga                                                      313
```

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15

```
caccgcgggt agatgaagta gaag                                           24
```

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16

```
cctccattcg cacatacagg                                                20
```

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17

```
caccagaggc gacggaggtt cc                                             22
```

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18

```
tctgctgctc gtaacagtcc                                                20
```

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19

```
gccactgaag caccgataga g                                              21
```

<210> SEQ ID NO 20
<211> LENGTH: 24
<212> TYPE: DNA
<213> ORGANISM: Artificial Sequence
<220> FEATURE:

<223> OTHER INFORMATION: primer

<400> SEQUENCE: 20
ttatcgaacc agaatgtcca tctc    24

<210> SEQ ID NO 21
<211> LENGTH: 30
<212> TYPE: DNA
<213> ORGANISM: Artificial Sequence
<220> FEATURE:
<223> OTHER INFORMATION: probe

<400> SEQUENCE: 21
tttctggatt acagcaactc gattggcttc    30

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gccactgaag caccgataga g    21

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
ttatcgaacc agaatgtcca tctc    24

<210> SEQ ID NO 24
<211> LENGTH: 18
<212> TYPE: DNA
<213> ORGANISM: Artificial Sequence
<220> FEATURE:
<223> OTHER INFORMATION: probe

<400> SEQUENCE: 24
tccgccggcg tcagcgac    18

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
gccggatacg gtggagaag    19

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26
ccaaacagcg ccttgctt    18

```
<210> SEQ ID NO 27
<211> LENGTH: 19
<212> TYPE: DNA
<213> ORGANISM: Artificial Sequence
<220> FEATURE:
<223> OTHER INFORMATION: probe

<400> SEQUENCE: 27
atggacattc tggttcgat                                                 19

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ctaagggtgc tgccagcttt                                                20

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
gtcaagcact ggagcatatc ca                                             22

<210> SEQ ID NO 30
<211> LENGTH: 26
<212> TYPE: DNA
<213> ORGANISM: Artificial Sequence
<220> FEATURE:
<223> OTHER INFORMATION: probe

<400> SEQUENCE: 30
atcatgaacc atccaggaca gattgg                                         26

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
gaattggaca atgagcttta gt                                             22

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tagatgtgtg gctgtaaatt g                                              21

<210> SEQ ID NO 33
<211> LENGTH: 21
<212> TYPE: DNA
<213> ORGANISM: Artificial Sequence
<220> FEATURE:
<223> OTHER INFORMATION: primer
```

```
<400> SEQUENCE: 33
ggcctaaacg ttgtaagaca a                                              21

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
tgcttagtta aatgctacag gg                                             22

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
aaatcgacac aaagggagga g                                              21

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
aacttcccca agcggctcca t                                              21

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gacctgaaca ttgcaagatg a                                              21

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ggcttacttg aatgctacaa gg                                             22

<210> SEQ ID NO 39
<211> LENGTH: 25
<212> TYPE: DNA
<213> ORGANISM: Artificial Sequence
<220> FEATURE:
<223> OTHER INFORMATION: primer

<400> SEQUENCE: 39
gcctcaatcg acacaaaagg gagag                                          25

<210> SEQ ID NO 40
<211> LENGTH: 24
```

```
<212> TYPE: DNA
<213> ORGANISM: Artificial Sequence
<220> FEATURE:
<223> OTHER INFORMATION: primer

<400> SEQUENCE: 40
agcgccttgc ttcggcttat cgat                                              24
```

VIRUS-RESISTANT TOBACCO AND BREEDING METHOD THEREFOR

CROSS REFERENCE TO RELATED APPLICATIONS

This application is a Continuation of PCT International Application No. PCT/JP2017/030492, filed on Aug. 25, 2017, which claims priority under 35 U.S.C. 119(a) to Patent Application No. 2016-166176, filed in Japan on Aug. 26, 2016, all of which are hereby expressly incorporated by reference into the present application.

TECHNICAL FIELD

The present invention relates to a virus-resistant tobacco and a method for producing the virus-resistant tobacco.

BACKGROUND ART

The genus *Potyvirus* is the largest group of plant viruses, and various plants play host to the genus *Potyvirus*. Potato virus Y (hereinafter referred to as PVY), which is a virus belonging to the genus *Potyvirus*, is non-persistently transmitted through aphids and infects various solanaceous plant species. As for tobacco (*Nicotiana tabacum*), PVY causes symptoms such as leaf mottling, vein and stem necroses, leaf yellowing, and growth inhibition, depending on a strain of PVY and a variety of tobacco which is infected by PVY. This results in a lower quality and a lower yield of leaf tobacco and consequently causes great damage to worldwide leaf tobacco production. In particular, appearance of symptoms of vein and stem necroses which appearance is followed by yellowing and browning of leaves frequently leads to wilting to death of a plant body itself and thus greatly affects quality and yield of leaf tobacco (Non-Patent Literature 1). Note that tobacco products to be produced from leaf tobacco which has been infected with PVY and thus has a lower quality greatly deteriorate in quality accordingly.

Meanwhile, Tobacco bushy top virus (hereinafter referred to as TBTV), which is a virus belonging to the genus *Umbravirus*, is known as a virus responsible for tobacco bushy top disease occurring in Africa and Asia. The TBTV is persistently transmitted by aphids in the natural environment and causes stunting and a leaf mottling symptom to tobacco. This results in a lower quality and a lower yield. The tobacco bushy top disease has been important disease damage particularly in African countries.

In tobacco, Virgin A mutant (hereinafter referred to as VAM), which is an existing genetic resource that is resistant to PVY, is known. The VAM has been positively used in a tobacco breeding program. However, a VAM-Breaking strain (PVY-Breaking strain, or may also be expressed as PVY-B), which is a new strain of PVY that breaks resistance of VAM, has recently been reported worldwide. This has caused a current strong demand for tobacco that is resistant to the VAM-Breaking strain. Tobacco that has acquired resistance to the VAM-Breaking strain by being exposed to radiation has been previously reported (Non-Patent Literature 2), but a gene responsible for the resistance to the VAM-Breaking strain has not yet been identified. Furthermore, some of tobacco wild species such as *Nicotiana africana* are known to be resistant to the PVY-Breaking strain and are being applied to tobacco (*Nicotiana tabacum*) breeding, but have not yet been practically used.

Meanwhile, exploration for sources of resistance to tobacco bushy top disease was carried out with use of 43 tobacco varieties and wild species belonging to the genus *Nicotiana*. As a result, it was reported that none of the tobacco varieties had been resistant to tobacco bushy top disease, whereas several species of the wild species had not shown any symptoms (Non-Patent Literature 3). However, a genetic mechanism of resistance of such wild species has not been made clear, and introduction of the resistance from the wild species into *N. tabacum*, which is a cultivated species, is expected to be accompanied by introduction of a trait that adversely affects quality and yield. Therefore, the introduction of the resistance of the wild species into *N. tabacum* still has a long way to go.

About half of approximately 200 genes of known plant virus-resistant genes are recessively inherited (Non-Patent Literature 4). These genes are considered to be host factors necessary for, for example, replication and cell-to-cell movement of viruses. Research carried out over the past decade has revealed some of these factors. For example, eukaryotic translation initiation factors such as eIF4E and eIF4G, DEAD-box RNA helicase-like protein (Non-Patent Literature 5), a cysteine-rich VPg-interacting protein (Non-Patent Literature 6), Translation elongation factor (Non-Patent Literature 7), and other factors have been identified as genetic elements of recessive virus resistance. It is a matter of course that the factors are not all of such host factors as described above, and a number of other host factors are considered to be candidates for virus-resistant genes (Non-Patent Literature 4). Examples of such candidates include various plant factors associated with phloem transport of plant viruses (Non-Patent Literature 8).

Viruses use translation initiation mechanisms of hosts to synthesize proteins from genomes of the viruses themselves. In 2002, it was shown that a genetic element of recessive resistance to Turnip mosaic virus (TuMV) in *Arabidopsis thaliana* is a mutation of a eukaryotic translation initiation factor eIF(iso)4E (Non-Patent Literature 9). Since then, involvement of an eIF4E gene family in recessive resistance to known viruses belonging to the genus *Potyvirus* has been studied in some plants. It is actually revealed that recessive virus resistance has been acquired by a mutation of eIF4E or eIF(iso)4E.

For example, Patent Literature 1 describes a method for imparting virus resistance to plants by silencing eIF4E. Patent Literature 2 describes a method for imparting virus resistance by suppression of the function of pepper eIF4E. Specifically, Patent Literature 2 describes a method for imparting virus resistance by overexpression of genes encoding eIF4E (excluding eIF(iso)4E) in which a mutation has occurred in a specific amino acid. Patent Literature 3 describes a mutant which has eIF4E or eIF(iso)4E, on which virus can not act, by splicing mutation of an eIF4E gene or an eIF(iso)4E gene. The mutation is occurrence of insertion, deletion, or substitution in at least one base in (i) a non-coding region of eIF4E or eIF(iso)4E or (ii) a splicing element (a region of ±10 bases at a boundary site between an exon and an intron) of eIF4E or eIF(iso)4E, and the mutation is intended to occur desirably in an intron, and more desirably in a first intron. Patent Literature 4 describes a method for selecting a plant resistant to pepper veinal mottle disease (Pepper veinal mottle virus (PVMV)) by combination of both a mutation in eIF4E and a mutation in eIF(iso)4E. Specifically, Patent Literature 4 describes a method for selecting a plant in which neither eIF4E nor eIF(iso)4E is expressed and mutated eIF4E is expressed.

Furthermore, for example, it is shown that a gene responsible for recessive resistance of pepper to PVY is eIF4E (Non-Patent Literature 10). Moreover, it is shown that Clover yellow vein virus multiplies in eIF(iso)4E-deficient *Arabidopsis thaliana* but does not multiply in eIF4E-deficient *Arabidopsis thaliana*, and, on the contrary, TuMV multiplies in the eIF4E-deficient *Arabidopsis thaliana* but does not multiply in the eIF(iso)4E-deficient *Arabidopsis thaliana* (Non-Patent Literature 11). Further, in order to acquire resistance to PVMV, both eIF4E and eIF(iso)4E need to lose their functions simultaneously (Non-Patent Literature 12). For example, Non-Patent Literature 13 and Non-Patent Literature 14 review recent eukaryotic translation initiation factors and plant virus resistance.

Association between (a) viruses different from the viruses belonging to the genus *Potyvirus* and (b) eukaryotic translation initiation factors has also been pointed out to a limited extent. For example, Cucumber mosaic virus (CMV) is a virus belonging to the genus *Cucumovirus*, and production of 3a protein involved in cell-to-cell movement of CMV is inhibited in *Arabidopsis thaliana* in which eIF4E or eIF4G has been disrupted (Non-Patent Literature 15). In addition, Rice yellow mottle virus (RYMV) is a virus belonging to the genus *Sobemovirus*, and rice in which eIF(iso)4G has a mutation is resistant to RYMV (Non-Patent Literature 16).

As for tomato, which is a solanaceous plant as with tobacco, a study of a relationship between *Potyvirus* resistance and a translation initiation factor eIF4E has been made based on a comprehensive analysis of a tomato mutant panel. The study has revealed that suppression of the function of eIF4E1, which is a member of the eIF4E gene family, imparts resistance to PVY and Pepper mottle virus (PepMoV) but does not impart resistance to Tobacco etch virus (TEV) (Non-Patent Literature 17). The study has also revealed that suppression of the functions of eIF4E2, eIF(iso)4E, eIF4G, and eIF(iso)4G does not impart resistance to these viruses belonging to the genus *Potyvirus*. Furthermore, it is shown that simultaneous suppression of the functions of eIF4E1 and eIF4E2 with use of RNAi (RNA interference) imparts resistance to seven species of viruses belonging to the genus *Potyvirus*, including PVY, PepMoV and TEV (Non-Patent Literature 18). However, interestingly, it is shown that RNAi targeting eIF(iso)4E does not impart resistance to any of these viruses (Non-Patent Literature 17). It is also shown that eIF(iso)4E of tomato is not associated with resistance to viruses different from the viruses belonging to the genus *Potyvirus* (Non-Patent Literature 18).

In plants, eIF(iso)4E, which is categorized as an eIF4E family, ordinarily has a DNA sequence identity of less than 60% with respect to eIF4E. In addition, eIF(iso)4E forms a translation complex different from a translation complex formed by eIF4E. Specifically, eIF(iso)4E, together with eIF(iso)4G, forms a translation complex eIF(iso)4F, and eIF4E, together with eIF4G, forms a translation complex eIF4F.

As for tobacco (*N. tabacum*), there is a report that an expression level of eIF4E1 or eIF(iso)4E was made lower (Non-Patent Literature 19). In this report, transcription of eIF4E1 or eIF(iso)4E of tobacco is suppressed by using antisense technology. Non-Patent Literature 19 describes achievement of production of (i) tobacco whose amount of transcripts of eIF4E1 is reduced to 30% to 40% of the amount of transcripts of eIF4E1 of a control and (ii) tobacco whose amount of transcripts of eIF(iso)4E is reduced to 60% of the amount of transcripts of eIF(iso)4E of a control. Furthermore, Non-Patent Literature 19 discloses that the amount of transcripts of eIF4E1 of a progeny made by crossbreeding the above tobaccos (i) and (ii) is reduced to 26% of the amount of transcripts of eIF4E1 of a control, and the amount of transcripts of eIF(iso)4E of the progeny is reduced to 31% of the amount of transcripts of eIF(iso)4E of a control. Note, however, that Non-Patent Literature 19 makes no mention of association between eIF4E1 or eIF(iso)4E and virus resistance. Note also that, though the possibility that HC-Pro protein of PVY interacts with eIF(iso)4E of tobacco is suggested by an assay system in which *Nicotiana benthamiana* is used (Non-Patent Literature 20), association between eIF(iso)4E and resistance is not pointed out.

As for tobacco, it was recently found, from a comprehensive analysis of transcripts of PVY-resistant VAM tobacco and transcripts of PVY-sensitive tobacco, that eIF4E is one of genes each of whose amount of transcription is specifically low in VAM tobacco, and it was shown that tobacco which has a mutation in this gene is resistant to PVY (Non-Patent Literature 21 and Non-Patent Literature 22). Tobacco (*N. tabacum*) is an amphidiploid which has a genome derived from *Nicotiana sylvestris* (S) and a genome derived from *Nicotiana tomentosiformis* (T). Thus, one set of genes derived from *N. sylvestris* (S) and one set of genes derived from *N. tomentosiformis* (T) are basically present in tobacco (*N. tabacum*). Non-Patent Literature 22 discloses that suppression of the function of S-derived eIF4E causes tobacco to be resistant to PVY.

Furthermore, as for tobacco, it was recently shown that suppression of the function of an eIF(iso)4E gene, which is a translation initiation factor, causes tobacco to be resistant to PVY-B and Tobacco bushy top virus (TBTV) (Patent Literature 5). More specifically, it was shown that suppression of the function of a T-derived eIF(iso)4E gene causes tobacco to be resistant to PVY-B and suppression of the function of an S-derived eIF(iso)4E gene causes tobacco to be resistant to TBTV (Patent Literature 5).

As described earlier, tobacco (*N. tabacum*), which is an amphidiploid, has twice as many genes as an ordinary diploid plant, and one set of genes derived from *N. sylvestris* and one set of genes derived from *N. tomentosiformis* are basically present in tobacco (*N. tabacum*). This makes tobacco (*N. tabacum*) more complicated in genetic mechanism than other diploid plants. In *Arabidopsis thaliana*, three eIF4Es and one type of eIF(iso)4E are supposed to be present (Non-Patent Literature 13). In tobacco, all translation initiation factors that are observed in *Arabidopsis thaliana* are considered to be present in pairs. It has been found that the eIF4E family of tobacco consists of at least 12 eukaryotic translation initiation factors in a case where a cap-binding protein that is functionally similar to eIF4E is also included in the eIF4E family (Non-Patent Literature 22). The tobacco eIF family consists of more translation initiation factors in a case where eIF4G and eIF(iso)4G are further included. Thus, much effort needs to be spent in finding out, among the above translation initiation factors, a factor involved in resistance to an intended virus through suppression of its function. Furthermore, more effort needs to be spent in (i) producing tobaccos in each of which the function of a eukaryotic translation initiation factor is suppressed, (ii) producing, by combining and crossbreeding the tobaccos produced in (i), tobaccos in which the functions of several different translation initiation factors are suppressed, (iii) examine the tobaccos produced in (ii) for virus resistance, and (iv) finding out a combination of factors involved in resistance to an intended virus.

CITATION LIST

Patent Literatures

[Patent Literature 1]
Specification of U.S. Patent Application Publication No. 2006/294618
[Patent Literature 2]
Specification of U.S. Pat. No. 7,772,462
[Patent Literature 3]
Specification of U.S. Patent Application Publication No. 2013/117879
[Patent Literature 4]
International Publication No. WO 2005/118850
[Patent Literature 5]
International Publication No. WO2015/199242

Non-Patent Literatures

[Non-Patent Literature 1]
Henderson R. G. and Troutman J. L. (1963) A severe virus disease of tobacco in Montgomery county, Virginia. Plant Disease Reporter 47-3: 187-189.
[Non-Patent Literature 2]
Pulcinelli et al. (2009) Reporting a source of PVYntn resistance in *Nicotiana tabacum* L. CORESTA Joint Study Groups Meeting, Rovinj, Croatia.
[Non-Patent Literature 3]
De Bruin. (1990) Sources of resistance in the genus *Nicotiana* to the virus causing bushy top disease in tobacco. Phytophylactica. 22: 263-264.
[Non-Patent Literature 4]
Truniger V, Aranda M A. (2009) Recessive resistance to plant viruses. Adv Virus Res. 75:119-159.
[Non-Patent Literature 5]
Huang et al. (2010) A host RNA helicase-like protein, AtRH8, interacts with the potyviral genome-linked protein, VPg, associates with the virus accumulation complex, and is essential for infection. Plant Physiol. 152: 255-266.
[Non-Patent Literature 6]
Dunoyer et al. (2004) A Cysteine-Rich Plant Protein Potentiates *Potyvirus* Movement through an Interaction with the Virus Genome-Linked Protein VPg. J. Virol. 78: 2301-2309.
[Non-Patent Literature 7]
Hwang et al. (2013) Translation elongation factor 1B (eEF1B) is an essential host factor for Tobacco mosaic virus infection in plants. Virology 439:105-114.
[Non-Patent Literature 8]
Hipper et al. (2013) Viral and cellular factors involved in Phloem transport of plant viruses. Front Plant Sci. 4: article 154.
[Non-Patent Literature 9]
Lellis et al. (2002) Loss-of-susceptibility mutants of *Arabidopsis thaliana* reveal an essential role for eIF(iso)4E during *Potyvirus* infection. Curr Biol. 12:1046-1051.
[Non-Patent Literature 10]
Ruffel et al. (2002) A natural recessive resistance gene against Potato virus Y in pepper corresponds to the eukaryotic initiation factor 4E (eIF4E). Plant J. 32, 1067-1075.
[Non-Patent Literature 11]
Sato et al. (2005) Selective involvement of members of the eukaryotic initiation factor 4E family in the infection of *Arabidopsis thalianaby Potyviruses*. FEBS Lett. 579: 1167-1171.
[Non-Patent Literature 12]
Ruffel et al. (2006) Simultaneous mutations in translation initiation factors eIF4E and eIF(iso)4E are required to prevent Pepper veinal mottle virus infection of pepper. J Gen Virol. 87, 2089-2098.
[Non-Patent Literature 13]
Robaglia and Caranta. (2006) Trends in Plant Science 11:40-45.
[Non-Patent Literature 14]
Leonardo et al. (2012) Breeding for resistance to viral diseases. in Fritsche-Neto and Borem (eds.), Plant breeding for biotic stress resistance. Springer-Verlag Berlin Heidelberg.
[Non-Patent Literature 15]
Yoshii et al. (2004) The *Arabidopsis Cucumovirus* Multiplication 1 and 2 Loci Encode Translation Initiation Factors 4E and 4G. J Virol. 78: 6102-6111.
[Non-Patent Literature 16]
Albar et al. (2006) Mutations in the eIF(iso)4G translation initiation factor confer high resistance of rice to Rice yellow mottle virus. Plant J. 47:417-426.
[Non-Patent Literature 17]
Piron et al. (2010) An induced mutation in tomato eIF4E leads to immunity to two *Potyviruses*. PLOS ONE 5: e11313.
[Non-Patent Literature 18]
Mazier et al. (2011) Knock-down of both eIF4E1 and eIF4E2 genes confers broad-spectrum resistance against *Potyviruses* in tomato. PLOS ONE 6: e29595.
[Non-Patent Literature 19]
Combe et al. (2005) Translation initiation factors eIF4E and eIFiso4E are required for polysome formation and regulate plant growth in tobacco. Plant Molecular Biology 57: 749-760.
[Non-Patent Literature 20]
Ala-Poikela et al. (2011) Helper Component Proteinase of the Genus *Potyvirus* Is an Interaction Partner of Translation Initiation Factors eIF(iso)4E and eIF4E and Contains a 4E Binding Motif. J Virol. 85: 6784-6794.
[Non-Patent Literature 21]
Julio et al. (2013) Characterisation of PVY (Potato virus Y) resistance in tobacco: potential role of an eIF4E gene identified by high throughput sequencing technologies. CORESTA Meeting Agro-Phyto Groups abstr. AP 29.
[Non-Patent Literature 22]
Julio et al. (2015) A Eukaryotic Translation Initiation Factor 4E (eIF4E) is Responsible for the "va" Tobacco Recessive Resistance to *Potyviruses*. Plant Mol Biol Rep. 33: 609-623.

SUMMARY OF INVENTION

Technical Problem

As described earlier, merely several examples of tobaccos having resistance to PVY-B are known, and persistence of the resistance of such tobaccos is still unclear. Therefore, in order to avoid potential genetic vulnerability of resistance of tobacco, it is necessary to develop another novel tobacco having resistance to viruses including the PVY-Breaking strain. Similarly, in order to avoid genetic vulnerability of resistance of tobacco, it is necessary to develop a novel tobacco having resistance to PVY.

The present invention thus has been made in view of the problems, and an object of the present invention is to provide a novel resistant tobacco having stronger resistance to PVY or PVY-B.

Solution to Problem

An aspect of a virus-resistant tobacco in accordance with the present invention is arranged such that: (i) a translation initiation factor eIF(iso)4E protein which is non-functional with respect to a virus is produced or (ii) expression of a translation initiation factor eIF(iso)4E gene is suppressed; and (a) a translation initiation factor eIF4E2 protein, which is non-functional with respect to a virus, is produced or (b) expression of a translation initiation factor eIF4E2 gene is suppressed, the translation initiation factor eIF(iso)4E being at least one of eIF(iso)4E-S and eIF(iso)4E-T, and the translation initiation factor eIF4E2 being at least one of eIF4E2-S and eIF4E2-T.

An aspect of a method in accordance with the present invention for producing a virus-resistant tobacco, includes the step of: producing tobacco resistant to a virus by (i) introducing a mutation into a translation initiation factor eIF(iso)4E gene, the mutation (a) causing production of a translation initiation factor eIF(iso)4E protein which is non-functional to a virus or (b) suppressing expression of the translation initiation factor eIF(iso)4E gene, and (ii) introducing a mutation into a translation initiation factor eIF4E2 gene, the mutation (c) causing production of a translation initiation factor eIF4E2 protein, which is non-functional with respect to a virus, or (d) suppressing expression of the translation initiation factor eIF4E2 gene, the translation initiation factor eIF(iso)4E being at least one of eIF(iso)4E-S and eIF(iso)4E-T, and the translation initiation factor eIF4E2 being at least one of eIF4E2-S and eIF4E2-T.

Another aspect of a method in accordance with the present invention for producing a virus-resistant tobacco, includes the step of: producing tobacco resistant to a virus by (i) introducing a factor that causes a translation initiation factor eIF(iso)4E gene to be expressed at a lower level than a wild type, and (ii) introducing a factor that causes a translation initiation factor eIF4E2 gene to be expressed at a lower level than a wild type, the translation initiation factor eIF(iso)4E being at least one of eIF(iso)4E-S and eIF(iso)4E-T, and the translation initiation factor eIF4E2 being at least one of eIF4E2-S and eIF4E2-T.

An aspect of a method in accordance with the present invention for producing a breeding progeny of a virus-resistant tobacco, includes self-pollinating or cross-pollinating (i) a virus-resistant tobacco produced by a method recited above or (ii) a progeny of the virus-resistant tobacco thus produced.

An aspect of a combination of detection polynucleotides in accordance with the present invention, the combination includes: a first detection polynucleotide which is a polynucleotide for detecting a mutation in a translation initiation factor eIF4E2 gene of tobacco, the mutation (i) causing production of an eIF4E2 protein which is non-functional with respect to a virus or (ii) suppressing expression of the eIF4E2 gene; and a second detection polynucleotide which is a polynucleotide for detecting a mutation in a translation initiation factor eIF(iso)4E gene of tobacco, the mutation (a) causing production of an eIF(iso)4E protein which is non-functional with respect to a virus or (b) suppressing expression of the eIF(iso)4E gene.

An aspect of a method in accordance with the present invention for selecting a virus-resistant tobacco includes: an examination step of examining tobacco for presence or absence of a mutation in genomic DNA by using a combination recited above; and a selection step of selecting, as the virus-resistant tobacco, tobacco in which the mutation has been detected in the examination step.

An aspect of a combination of DNA markers in accordance with the present invention for determining whether tobacco is resistant to a virus, the combination includes: a first determination DNA marker which contains a polynucleotide consisting of a continuous base sequence which contains a mutation in a translation initiation factor eIF4E2 gene or of a sequence complementary to the continuous base sequence, the mutation (i) causing production of an eIF4E2 protein which is non-functional with respect to a virus or (ii) suppressing expression of the eIF4E2 gene; and a second determination DNA marker which contains a polynucleotide consisting of a continuous base sequence which contains a mutation in a translation initiation factor eIF(iso)4E gene or of a sequence complementary to the continuous base sequence, the mutation (a) causing production of an eIF(iso)4E protein which is non-functional with respect to a virus or (b) suppressing expression of the eIF(iso)4E gene.

An aspect of leaf tobacco in accordance with the present invention is leaf tobacco of a virus-resistant tobacco recited above.

An aspect of a tobacco product in accordance with the present invention contains, as a material, leaf tobacco recited above.

Advantageous Effects of Invention

An embodiment of the present invention makes it possible to provide a novel virus-resistant tobacco having resistance to a virus.

BRIEF DESCRIPTION OF DRAWINGS

FIG. 1 shows expression levels of the eIF(iso)4E-S gene and the eIF(iso)4E-T gene which expression levels are measured relative to an average value, which is 1, of the amount of transcripts of a control.

FIG. 2 shows expression levels of the eIF4E2 gene and the eIF(iso)4E gene which expression levels are measured relative to an average value, which is 1, of the amount of transcripts of a control. Error bars each show a standard error.

DESCRIPTION OF EMBODIMENTS

Figure 1:
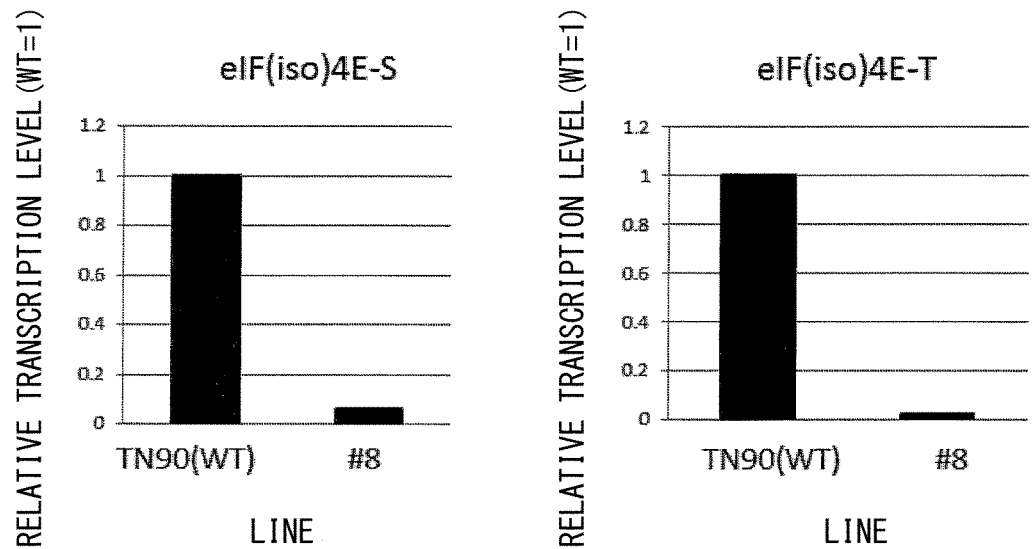
FIG. 1 shows results of quantitative PCR analysis of an eIF(iso)4E-S gene and an eIF(iso)4E-T gene expression in recombinant tobacco obtained by introducing an RNAi construct of an eIF(iso)4E gene into tobacco variety TN90.

The inventors of the present application found a method for conferring combined virus resistance to tobacco by suppressing the functions of two genes, which are a translation initiation factor eIF4E2 gene and a translation initiation factor eIF(iso)4E gene, of tobacco. Tobacco produced by the above method was resistant to Potato virus Y (PVY), which is a virus belonging to the genus *Potyvirus*, and PVY-B (a VAM-breaking strain of PVY), and was also resistant to Tobacco bushy top virus (TBTV), which is a virus belonging to the genus *Umbravirus*. Specifically, recombinant tobacco obtained by introducing, into tobacco variety TN90 in which eIF4E2-S had been deleted, an RNAi construct which suppresses transcription of both an eIF(iso)4E-T gene (described later) and an eIF(iso)4E-S gene (described later) was produced and subjected to a virus assay, and, as a result, the recombinant tobacco was resistant to all three viruses, which are PVY, PVY-B, and TBTV. Furthermore, the recombinant tobacco was more resistant to PVY than tobacco in which the function of eIF4E2-S was suppressed, and was also more resistant to PVY-B than tobacco in which the functions of both eIF(iso)4E-S and eIF(iso)4E-T were broken. Meanwhile, a tobacco mutant in which the functions of eIF4E2-S and eIF(iso)4E-T were broken was produced and subjected to a virus assay. As a result, the tobacco mutant was more resistant to PVY than tobacco in which the function of eIF4E2-S was suppressed, and was also more resistant to PVY-B than tobacco in which the function of eIF(iso)4E-T was broken and tobacco in which the functions of both eIF(iso)4E-S and eIF(iso)4E-T were broken. Moreover, a tobacco mutant in which the functions of the following three: eIF4E2-S; eIF(iso)4E-S; and eIF(iso)4E-T, were broken was produced and subjected to a virus assay. As a result, the tobacco mutant was more resistant to PVY than tobacco in which the function of eIF4E2-S was suppressed, and was also more resistant to PVY-B than tobacco in which the functions of both eIF(iso)4E-S and eIF(iso)4E-T were broken.

It has been shown that resistance of VAM to PVY is due to deletion of a translation initiation factor eIF4E2-S gene. Furthermore, it has been reported that resistance to PVY-B and TBTV is due to breakage of the function of the eIF(iso)4E gene. Note, however, that no tobacco that is resistant to all the three viruses, which are PVY, PVY-B, and TBTV, has been known.

Tobacco in which the functions of both eIF4E2 and eIF(iso)4E were suppressed was resistant to all of PVY, PVY-B, and TBTV, and consequently was made more practically usable. Note that it is beyond expectation that the tobacco in which the functions of both eIF4E2 and eIF(iso)4E were suppressed was made more resistant to each of PVY and PVY-B than existing resistant tobacco, i.e., tobacco in which the function of eIF4E2-S was suppressed and tobacco in which the function of eIF(iso)4E was suppressed. Such an effect was an unexpected synergistic effect.

The following description will discuss an embodiment of a virus-resistant tobacco in accordance with an embodiment of the present invention. Unless otherwise specified, any numerical range expressed as "A to B" herein means "not less than A and not more than B".

[1. Virus-Resistant Tobacco and Method for Producing the Virus-Resistant Tobacco]

A virus-resistant tobacco in accordance with the present embodiment is arranged such that: (i) a translation initiation factor eIF(iso)4E protein which is non-functional with respect to a virus is produced or (ii) expression of a translation initiation factor eIF(iso)4E gene is suppressed; and (a) a translation initiation factor eIF4E2 protein which is non-functional with respect to a virus is produced or (b) expression of a translation initiation factor eIF4E2 gene is suppressed.

"Virus resistance" herein refers to delay, alleviation, or nonoccurrence of a symptom, occurring in tobacco due to viral infection, as compared with a susceptible tobacco variety. Examples of the symptom occurring in tobacco include stunting, vein necrosis, stem necrosis, vein cleaning, and mottling. Alternatively, the "virus resistance" refers to suppression of multiplication of a virus or suppression of cell-to-cell movement of a virus, as compared with a susceptible tobacco variety.

Further, examples of the "tobacco" can include an entire tobacco plant, tobacco plant tissues (e.g., a leaf, a stem, a flower, a root, a reproductive organ, an embryo, and a part thereof), a tobacco seedling, a tobacco seed, a dried tobacco leaf, a dried tobacco stem, a dried tobacco flower, a dried tobacco root, and a dried tobacco seed.

Nicotiana tabacum, which is a plant belonging to the genus Nicotiana, is an amphidiploid and has both a Nicotiana sylvestris-derived genome (S-type genome) and a Nicotiana tomentosiformis-derived genome (T-type genome), each of which is an ancestral species thereof. Thus, N. tabacum has two pairs of eIF(iso)4E genes having different base sequences and two pairs of eIF4E2 genes having different base sequences. Thus, "a translation initiation factor eIF(iso)4E protein which is non-functional is produced" means that a translation initiation factor eIF(iso)4E-S protein which is non-functional is produced and/or that a translation initiation factor eIF(iso)4E-T protein which is non-functional is produced. Similarly, "expression of a translation initiation factor eIF(iso)4E gene is suppressed" means that expression of a translation initiation factor eIF(iso)4E-S gene is suppressed and/or that expression of a translation initiation factor eIF(iso)4E-T gene is suppressed. Furthermore, "a translation initiation factor eIF4E2 protein which is non-functional is produced" means that a translation initiation factor eIF4E2-S protein which is non-functional is produced and/or that a translation initiation factor eIF4E2-T protein which is non-functional is produced. Similarly, "expression of a translation initiation factor eIF4E2 gene is suppressed" means that expression of a translation initiation factor eIF4E2-S gene is suppressed and/or that expression of a translation initiation factor eIF4E2-T gene is suppressed. That is, unless otherwise noted, merely "eIF(iso)4E" is herein intended to refer to eIF(iso)4E-S and/or eIF(iso)4E-T. Similarly, unless otherwise noted, merely "eIF4E2" is intended to refer to eIF4E2-S and/or eIF4E2-T. Furthermore, of the genes, the eIF(iso)4E-S gene and the eIF4E2-S gene may each be merely referred to as an "S-type", and the eIF(iso)4E-T gene and the eIF4E2-T gene may each be merely referred to as a "T-type".

Thus, in a case where (i) each S-type gene in which a non-functional protein is produced or whose expression is suppressed is denoted as a lowercase letter "s" and each T-type gene in which a non-functional protein is produced or whose expression is suppressed is denoted as a lowercase letter "t", and (ii) each S-type gene which is normal, in which functional protein is produced, and whose expression is not suppressed is denoted as a capital letter "S" and each T-type gene which is normal, in which functional protein is produced, and whose expression is not suppressed is denoted as a capital letter "T", the virus-resistant tobacco in accordance with the present embodiment has the following nine combinations:

(1) eIF4E2-ssTT/eIF(iso)4E-ssTT
(2) eIF4E2-ssTT/eIF(iso)4E-SStt
(3) eIF4E2-ssTT/eIF(iso)4E-sstt
(4) eIF4E2-SStt/eIF(iso)4E-ssTT
(5) eIF4E2-SStt/eIF(iso)4E-SStt
(6) eIF4E2-SStt/eIF(iso)4E-sstt
(7) eIF4E2-sstt/eIF(iso)4E-ssTT
(8) eIF4E2-sstt/eIF(iso)4E-SStt
(9) eIF4E2-sstt/eIF(iso)4E-sstt Note, however, that each of the combinations is encompassed in the scope of the present invention.

The eIF(iso)4E and the eIF4E2 each of which is not only contained in N. tabacum but also encoded by an N. sylvestris-derived genome of a plant belonging to the genus Nicotiana and having the N. sylvestris-derived genome are herein referred to as the "eIF(iso)4E-S" and "eIF4E2-S", respectively. Similarly, the eIF(iso)4E and the eIF4E2 each of which is encoded by an *N. tomentosiformis*-derived genome of a plant belonging to the genus *Nicotiana* and having the *N. tomentosiformis*-derived genome are referred to as the "eIF(iso)4E-T" and "eIF4E2-T", respectively.

Thus, the "tobacco" herein encompasses not only *N. tabacum* but also another variety belonging to the genus *Nicotiana* and having at least one of the *N. sylvestris*-derived genome and the *N. tomentosiformis*-derived genome. Examples of the another variety belonging to the genus *Nicotiana* include *N. sylvestris* and plants belonging to the genus *Nicotiana* and included in the section Tomentosae, such as *N. tomentosa, N. tomentosiformis, N. kawakamii, N. otophora, N. setchellii,* and N. *Glutinosa*.

The "eIF(iso)4E protein which is non-functional with respect to a virus" refers to an eIF(iso)4E protein which cannot be used for self-multiplication or cell-to-cell movement of a virus (the use of that eIF(iso)4E protein is at least partially inhibited), and encompasses both an eIF(iso)4E protein which does not carry out the normal function (as a translation initiation factor) of an eIF(iso)4E protein in tobacco and an eIF(iso)4E protein which carries out the normal function of an eIF(iso)4E protein in tobacco but prevents a virus from using the eIF(iso)4E protein. Same applies to the "eIF4E2 protein which is non-functional with respect to a virus". The "eIF(iso)4E protein which is non-functional with respect to a virus" and the "eIF4E2 protein which is non-functional with respect to a virus" can each be produced, for example, within a cell.

It can be determined by a virus assay whether a protein is non-functional with respect to a virus. The virus assay can be carried out by disease symptom examination, or by detection, measurement, or the like of a viral protein or a viral genome. For example, the ELISA method and the Western blot method in each of which an antibody to a viral protein is used can be used to detect and measure a viral protein. The antibody can be a commercially-available antibody, and an ELISA kit can be a commercially available ELISA kit. For PVY and PVY-B, it is possible to use, for example, a PVY PathoScreen Kit (registered trademark) of Agdia (registered trademark), Inc. Furthermore, for example, a reverse transcription quantitative PCR method can be used to detect and measure a virus RNA genome. Specifically, PCR can be carried out by obtaining, for example, a genomic sequence of PVY from a public database, appropriately designing a primer sequence and a probe sequence for quantitative PCR, and using, as a template, a cDNA sample obtained by reverse-transcribing RNA which has been extracted from a plant sample. In a case where the disease symptom examination shows that target tobacco has a disease symptom that occurs late or is alleviated, or has no disease symptom, relative to tobacco in which a translation initiation factor has no mutation, the target tobacco is non-functional to a virus. Alternatively, in a case where detection, measurement, or the like of a viral protein or a viral genome shows that target tobacco contains the viral protein or the viral genome in an amount that is preferably not more than half, more preferably not more than 1/3, even more preferably not more than 1/4, and most preferably not more than 1/5 of an amount of the viral protein or the viral genome which is contained in tobacco in which a translation initiation factor has no mutation, the target tobacco is non-functional to a virus.

The "expression level of an eIF(iso)4E gene" can be the amount of transcription to mRNA of eIF(iso)4E (the transcriptional level or the amount of transcripts) and/or the amount of translation to an eIF(iso)4E protein (the translational level or the amount of translation products). Thus, the expression "eIF(iso)4E expression is suppressed" encompasses (1) a case where transcription from an eIF(iso)4E gene of a virus-resistant tobacco of an embodiment of the present invention is further suppressed as compared with transcription from an eIF(iso)4E gene of a wild-type tobacco and/or (2) a case where translation from a translation product of the eIF(iso)4E gene of the virus-resistant tobacco of an embodiment of the present invention to a protein is further suppressed as compared with translation from a translation product of the eIF(iso)4E gene of the wild-type tobacco to a protein. Note that the expression "transcription is suppressed" encompasses a case where transcripts are degraded. That is, the expression "eIF(iso)4E expression is suppressed" also encompasses a case where an eIF(iso)4E gene is expressed at a lower level than a wild type by, for example, degradation of a transcriptional product. Same applies to the "expression level of an eIF4E2 gene" and the expression "eIF4E2 expression is suppressed". The eIF(iso)4E gene and the eIF4E2 gene are intended for those expressed, for example, within a cell.

A virus to which a virus-resistant tobacco is resistant is not limited to any particular virus. Examples of the virus include viruses with which to infect tobaccos, such as viruses belonging to the genus *Alfamovirus* (e.g., Alfalfa mosaic virus), viruses belonging to the genus *Curtovirus* (e.g., Beet curly top virus), viruses belonging to the genus *Begomovirus* (e.g., Tobacco leaf curl virus), viruses belonging to the genus *Cucumovirus* (e.g., Cucumber mosaic virus and Peanut stunt virus), viruses belonging to the genus *Ilarvirus* (e.g., Tobacco streak virus), viruses belonging to the genus *Potyvirus* (e.g., Potato virus Y (PVY), Tobacco etch virus, Tobacco vein mottling virus, and Tobacco vein banding mosaic virus), viruses belonging to the genus *Tobamovirus* (e.g., Tobacco mosaic virus), viruses belonging to the genus *Tobravirus* (e.g., Tobacco rattle virus), viruses belonging to the genus *Necrovirus* (e.g., Tobacco necrosis virus), viruses belonging to the genus *Varicosavirus* (e.g., Tobacco stunt virus), viruses belonging to the genus *Nepovirus* (e.g., Tobacco ringspot virus), viruses belonging to the genus *Umbravirus* (e.g., Tobacco bushy top virus and Tobacco mottle virus), viruses belonging to the genus *Polerovirus* (e.g., Tobacco vein distorting virus), viruses belonging to the genus *Mastrevirus* (e.g., Tobacco yellow dwarf virus), and viruses belonging to the genus *Tospovirus* (e.g., Tomato spotted wilt virus). The virus-resistant tobacco in accordance with an embodiment of the present invention can be arranged to be resistant to one type of virus, or can be arranged to be resistant to a plurality of types of viruses. The virus-resistant tobacco in accordance with an embodiment of the present invention can be arranged to be remarkably resistant to the viruses belonging to the genus *Potyvirus*. The virus-resistant tobacco in accordance with an embodiment of the present invention can be resistant to the PVY-O strain, the PVY-C strain, the PVY-Z strain, and the PVY-N (including NTN and NW) strain of Potato virus Y (PVY), particularly to the PVY strain (the VAM-Breaking strain) which breaks virus resistance of Virgin A mutant of tobacco or virus resistance of a tobacco line in which eIF4E2-S is deleted or the function of eIF4E2-S is suppressed. Further, the virus-resistant tobacco in accordance with an embodiment of the present invention can be remarkably resistant to viruses belonging to the genus *Umbravirus*, and can be resistant particularly to Tobacco bushy top virus (TBTV).

(EIf4E2 Gene)

An example of a cDNA sequence of a wild-type eIF4E2-S gene is represented by SEQ ID NO: 1 (GenBank accession number: KF155696). In SEQ ID NO: 1, an open reading frame is the 112nd to 771st bases. Furthermore, an example of an amino acid sequence of a wild-type eIF4E2-S protein is represented by SEQ ID NO: 2, and an example of a base sequence of a genome of the wild-type eIF4E2-S protein is represented by SEQ ID NO: 3. In SEQ ID NO: 3, a translation initiation codon is the 241st to 243rd bases, and a translation termination codon is the 5307th to 5309th bases. In SEQ ID NO: 3, exons are the 131st to 491st bases (Exon 1), the 3031st to 3196th bases (Exon 2), the 3309th to 3434th bases (Exon 3), the 5106th to 5171st bases (Exon 4), and the 5259th to 5540th bases (Exon 5).

An example of a cDNA sequence of a wild-type eIF4E2-T gene is represented by SEQ ID NO: 4 (GenBank accession number: KM202068). In SEQ ID NO: 4, an open reading frame is the 61st to 717th bases. Furthermore, an example of an amino acid sequence of a wild-type eIF4E2-T protein is represented by SEQ ID NO: 5, and an example of a base sequence of a genome of the eIF4E2-T protein is represented by SEQ ID NO: 6. In SEQ ID NO: 6, a translation initiation codon is the 1765th to 1767th bases, and a translation termination codon is the 7112nd to 7114th bases. In SEQ ID NO: 6, exons are the 1705th to 2012nd bases (Exon 1), the 4639th to 4804th bases (Exon 2), the 4915th to 5040th bases (Exon 3), the 6927th to 6992nd bases (Exon 4), and the 7064th to 7114th bases (Exon 5).

Note that the eIF4E2-T gene of GenBank accession number KM202068 has a DNA sequence identity in a protein-coding region of 93.2% (612 bases out of 657 bases coincide) with respect to the eIF4E2-S gene of GenBank accession number KF155696. Note also that the protein encoded by the eIF4E2-T gene of GenBank accession number KM202068 and the protein encoded by the eIF4E2-S gene of GenBank accession number KF155696 have an amino acid sequence identity of 87.7% (192 amino acids of 219 amino acids coincide) and have an amino acid sequence similarity of 97%.

Genes of plants whose genes are identical in function can differ in base sequence in a protein-coding region by approximately 1% to several percent between cultivars, and by approximately several percent to 10% between a cultivar and a wild relative, depending on a gene. A wild-type eIF4E2 gene in which no mutation has occurred herein encompasses a gene which causes production of mRNA corresponding to cDNA and consisting of a base sequence represented by SEQ ID NO: 1 or SEQ ID NO: 4 and a gene which encodes an eIF4E2 protein consisting of an amino acid sequence represented by SEQ ID NO: 2 or SEQ ID NO: 5. Furthermore, the wild-type eIF4E2 gene in which no mutation has occurred herein encompasses a gene which (i) causes production of mRNA having a sequence identity of 94% or higher, preferably 95% or higher, more preferably 97% or higher, even more preferably 99% or higher, with respect to mRNA corresponding to cDNA and consisting of a base sequence represented by SEQ ID NO: 1 or SEQ ID NO: 4 and (ii) encodes a functional eIF4E2 protein. Moreover, the wild-type eIF4E2 gene herein encompasses a gene which encodes a functional eIF4E2 protein having a sequence identity of 88% or higher, preferably 90% or higher, more preferably 95% or higher, even more preferably 97% or higher, particularly preferably 99% or higher, with respect to the amino acid sequence represented by SEQ ID NO: 2 or SEQ ID NO: 5. Further, the wild-type eIF4E2 gene herein encompasses a gene which (i) causes production of mRNA corresponding to a base sequence in which 1 base to 50 bases, 1 base to 40 bases, 1 base to 30 bases, 1 base to 20 bases, 1 base to 15 bases, 1 base to 12 bases, 1 base to 10 bases, 1 base to 8 bases, 1 base to 5 bases, 1 base to 3 bases, 1 base to 2 bases, or one base is/are substituted, deleted, inserted, and/or added in the base sequence represented by SEQ ID NO: 1 or SEQ ID NO: 4 and (ii) encodes a functional eIF4E2 protein. Furthermore, the wild-type eIF4E2 gene herein encompasses a gene which encodes a functional eIF4E2 protein having an amino acid sequence in which 1 to 20 amino acids, 1 to 15 amino acids, 1 to 12 amino acids, 1 to 10 amino acids, 1 to 8 amino acids, 1 to 5 amino acids, 1 to 4 amino acids, 1 to 3 amino acids, 1 to 2 amino acids, or one amino acid is/are substituted, deleted, inserted, and/or added in the amino acid sequence represented by SEQ ID NO: 2 or SEQ ID NO: 5.

For example, a wild-type eIF4E2-T gene in which no mutation has occurred herein encompasses a gene whose mRNA sequence is identical to the sequence of GenBank accession number KM202068. This sequence is derived from an eIF4E2-T gene of tobacco line T021658, and a DNA sequence corresponding to a protein-coding region of KM202068 has a sequence identity of 99.2% (652 bases out of 657 bases coincide) with respect to an exon sequence of a genomic DNA sequence of an eIF4E2-T of tobacco variety K326. A difference of approximately 1% (5 bases out of the 657 bases differing) is considered to be due to a difference between tobacco lines/tobacco varieties.

Note that "base sequence identity" herein refers to the percentage of alignments of bases which match exactly between a plurality of base sequences. Similarly, "amino acid sequence identity" refers to the percentage of alignments of amino acids which match exactly between a plurality of amino acid sequences. Furthermore, "amino acid sequence similarity" herein refers to the percentage of alignments of amino acids which match exactly or have similar properties between a plurality of amino acid sequences. Examples of the amino acids similar in property include lysine, arginine, and histidine each having a residue having a positive electric charge; asparatic acid and glutamic acid each having a residue having a negative electric charge; alanine, valine, leucine, isoleucine, methionine, tryptophan, phenylalanine, and proline each having a nonpolar residue, i.e., a hydrophobic residue; and glycine, serine, threonine, cysteine, tyrosine, asparagine, and glutamine each being polar but having no electric charge.

The "base sequence identity", "amino acid sequence identity", or "amino acid sequence similarity" can be calculated by using, for example, BLAST (Literature: Altschul et al. (1990) Basic local alignment search tool. J Mol Biol. 215:403-410), which is a sequence analysis (homology search) program commonly used by a person skilled in the art, or by using commercially available nucleic acid and amino acid analysis software. BLAST search can be carried out on a website of, for example, GenBank(www.ncbi.nlm-.nih.gov/genbank/) or DNA Data Bank of Japan (www.ddbj.nig.ac.jp/index-j.html). During the BLAST search, various search parameters can be changed, but default values are ordinarily used The "mutation" herein refers to point mutation, deletion, insertion, duplication, translocation, and inversion in DNA. Unless otherwise specified, the "mutation" refers to a difference from a wild-type base sequence.

The base sequence of the above-described wild-species eIF4E2 gene can be obtained by using the base sequence represented by SEQ ID NO: 1 or SEQ ID NO: 4 to carry out homology search with respect to genomes (Whole genome shotgun contigs) of *N. sylvestris, N. tomentosiformis,* or *N. otophora,* which genomes are registered in GenBank, with use of, for example, a BLAST program. Alternatively, a base sequence of an eIF4E2 gene of a plant species derived from a plant belonging to the genus *Nicotiana* can, for example, be obtained by amplifying the eIF4E2 gene from genomic DNA of the plant species by a PCR method with use of a primer sequence designed based on an eIF4E2 gene sequence herein shown, and then determining a base sequence. The homology search can be carried out by using the BLAST program or by using commercially available nucleic acid and amino acid sequence analysis software.

Furthermore, a base sequence of an eIF4E2 gene of a tobacco wild species can be obtained, from a genomic library or a cDNA library of tobacco wild species, by carrying out a hybridization experiment under stringent conditions with use of the base sequence represented by SEQ ID NO: 1 or SEQ ID NO: 4 as a probe.

(eIF(iso)4E Gene)

An example of a cDNA sequence of a wild-type eIF(iso)4E-S gene is represented by SEQ ID NO: 7 (GenBank accession number: AY699609). In SEQ ID NO: 7, an open reading frame is the 70th to 672nd bases. Furthermore, an example of an amino acid sequence of a wild-type eIF(iso)4E-S protein is represented by SEQ ID NO: 8, and an example of a base sequence of a genome of the eIF(iso)4E-S is represented by SEQ ID NO: 9. In SEQ ID NO: 9, a translation initiation codon is the 201st to 203rd bases, and a translation termination codon is the 4938th to 4940th bases. In SEQ ID NO: 9, exons are the 132nd to 397th bases (Exon 1), the 1730th to 1898th bases (Exon 2), the 2029th to 2154th bases (Exon 3), the 4723th to 4785th bases (Exon 4), and the 4893rd to 5096th bases (Exon 5).

An example of a cDNA sequence of a wild-type eIF(iso)4E-T gene is represented by SEQ ID NO: 10 (GenBank accession number: EB683576). In SEQ ID NO: 10, an open reading frame is the 37th to 624th bases. Furthermore, an example of an amino acid sequence of a wild-type eIF(iso)4E-T protein is represented by SEQ ID NO: 11, and an example of a base sequence of a genome of the eIF(iso)4E-T is represented by SEQ ID NO: 12. In SEQ ID NO: 12, a translation initiation codon is the 201st to 203rd bases, and a translation termination codon is the 3418th to 3420th bases. In SEQ ID NO: 12, exons are the 164th to 382nd bases (Exon 1), the 1620th to 1788th bases (Exon 2), the 1919th to 2044th bases (Exon 3), the 3205th to 3267th bases (Exon 4), and the 3373rd to 3593rd bases (Exon 5).

Genes of plants whose genes are identical in function can differ in base sequence in a protein-coding region by approximately 1% to several percent between cultivars, and by approximately several percent to 10% between a cultivar and a wild relative, depending on a gene. A wild-type eIF(iso)4E gene in which no mutation has occurred herein encompasses a gene which causes production of mRNA corresponding to cDNA and consisting of a base sequence represented by SEQ ID NO: 7 or SEQ ID NO: 10 and a gene which encodes an eIF(iso)4E protein consisting of an amino acid sequence represented by SEQ ID NO: 8 or SEQ ID NO: 11. Furthermore, the wild-type eIF(iso)4E gene in which no mutation has occurred herein encompasses a gene which (i) causes production of mRNA having a sequence identity of 92% or higher, preferably 95% or higher, more preferably 97% or higher, even more preferably 99% or higher, with respect to mRNA corresponding to cDNA and consisting of a base sequence represented by SEQ ID NO: 7 or SEQ ID NO: 10 and (ii) encodes a functional eIF(iso)4E protein. Moreover, the wild-type eIF(iso)4E gene herein encompasses a gene which encodes a functional eIF(iso)4E protein having a sequence identity of 92% or higher, preferably 95% or higher, more preferably 97% or higher, even more preferably 99% or higher, with respect to the amino acid sequence represented by SEQ ID NO: 8 or SEQ ID NO: 11. Further, the wild-type eIF(iso)4E gene herein encompasses a gene which (i) causes production of mRNA corresponding to a base sequence in which 1 base to 50 bases, 1 base to 40 bases, 1 base to 30 bases, 1 base to 20 bases, 1 base to 15 bases, 1 base to 12 bases, 1 base to 10 bases, 1 base to 8 bases, 1 base to 5 bases, 1 base to 3 bases, 1 base to 2 bases, or one base is/are substituted, deleted, inserted, and/or added in the base sequence represented by SEQ ID NO: 7 or SEQ ID NO: 10 and (ii) encodes a functional eIF(iso)4E protein. Furthermore, the wild-type eIF(iso)4E gene herein encompasses a gene which encodes a functional eIF(iso)4E protein having an amino acid sequence in which 1 to 20 amino acids, 1 to 15 amino acids, 1 to 12 amino acids, 1 to 10 amino acids, 1 to 8 amino acids, 1 to 5 amino acids, 1 to 4 amino acids, 1 to 3 amino acids, 1 to 2 amino acids, or one amino acid is/are substituted, deleted, inserted, and/or added in the amino acid sequence represented by SEQ ID NO: 8 or SEQ ID NO: 11.

For example, a wild-type eIF(iso)4E-T gene in which no mutation has occurred herein encompasses a gene whose cDNA sequence is identical to the sequence of GenBank accession number FN666434. This sequence, which is derived from an eIF(iso)4E-T gene derived from tobacco variety Samsun NN, has a sequence identity of 97% with respect to a cDNA sequence EB683576 of eIF(iso)4E-T derived from tobacco variety K326. Proteins encoded by these two genes have an amino acid sequence identity of 97% and an amino acid sequence similarity of 99%.

It is considered that a cDNA sequence of an eIF(iso)4E gene of a plant belonging to the genus *Nicotiana* (described earlier) has a sequence identity of 90% or higher with respect to the base sequence represented by SEQ ID NO: 7 or SEQ ID NO: 10. In fact, the base sequence represented by SEQ ID NO: 7 has a sequence identity of 100% with respect to a cDNA sequence (excluding introns) of an eIF(iso)4E gene of *N. sylvestris*. The base sequence represented by SEQ ID NO: 10 has a sequence identity of 99% with respect to a cDNA sequence (excluding introns) of eIF(iso)4E of *N. tomentosiformis*. The base sequence represented by SEQ ID NO: 7 and the base sequence represented by SEQ ID NO: 10 have respective sequence identities of 98% and 99% with a genomic sequence (excluding introns) of eIF(iso)4E of *N. otophora*.

The base sequence of the above-described wild-species eIF(iso)4E gene can be obtained by using the base sequence represented by SEQ ID NO: 7 or SEQ ID NO: 10 to carry out homology search with respect to genomes (Whole genome shotgun contigs) of *N. sylvestris, N. tomentosiformis*, or *N. otophora*, which genomes are registered in GenBank, with use of, for example, a BLAST program. Alternatively, a base sequence of an eIF(iso)4E gene of a plant species derived from a plant belonging to the genus *Nicotiana* can, for example, be obtained by amplifying the eIF(iso)4E gene from genomic DNA of the plant species by a PCR method with use of a primer sequence designed based on an eIF(iso)4E gene base sequence herein shown, and then determining a base sequence. The homology search can be carried out by using the BLAST program or by using commercially available nucleic acid and amino acid sequence analysis software.

Furthermore, a base sequence of an eIF(iso)4E gene of a tobacco wild species can be obtained, from a genomic library or a cDNA library of tobacco wild species, by carrying out a hybridization experiment under stringent conditions with use of the base sequence represented by SEQ ID NO: 7 or SEQ ID NO: 10 as a probe.

(Aspect 1 of Virus-Resistant Tobacco)

In an aspect, a virus-resistant tobacco has a mutation in a translation initiation factor eIF(iso)4E gene, and the mutation (i) causes production of a translation initiation factor eIF(iso)4E protein which is non-functional with respect to a virus or (ii) suppresses expression of the translation initiation factor eIF(iso)4E gene.

Alternatively, the virus-resistant tobacco has a mutation in a translation initiation factor eIF4E2 gene, and the mutation (i) causes production of a translation initiation factor eIF4E2 protein which is non-functional with respect to a virus or (ii) suppresses expression of the translation initiation factor eIF4E2 gene.

Alternatively, the virus-resistant tobacco has a mutation in the translation initiation factor eIF(iso)4E gene and a mutation in the translation initiation factor eIF4E2 gene.

In a case where the virus-resistant tobacco in accordance with an embodiment of the present invention has a mutation in a coding region of the eIF(iso)4E gene, the mutation can cause a mutation in the amino acid sequence of an eIF(iso)4E protein. Similarly, in a case where the virus-resistant tobacco in accordance with an embodiment of the present invention has a mutation in a coding region of the eIF4E2 gene, the mutation can cause a mutation in the amino acid sequence of an eIF4E2 protein. Examples of the mutation of the amino acid sequence include substitution, deletion, and insertion. In a case where the mutation is substitution of an amino acid, an amino acid to be substituted and a substituted amino acid are not limited to specific ones, provided that the protein encoded by the target gene is rendered non-functional with respect to a virus. For example, such substitution is preferably non-conservative substitution. The non-conservative substitution is exemplified by substitution of an amino acid by another amino acid having a different charge or a different hydrophobicity (e.g., substitution of a basic amino acid by an acidic amino acid or substitution of a polar amino acid by a non-polar amino acid) and substitution of a certain amino acid by another amino acid having a different size of a side chain. Out of these, mutations which render the protein encoded by the target gene non-functional with respect to a virus are encompassed in the intended scope of the present invention. Whether or not a protein has been rendered non-functional with respect to a virus can be determined by a virus assay. Further, in a case where the mutation occurs in the coding region, the mutation may be a frame-shift mutation or a nonsense mutation (a mutation that causes a change to a stop codon). In a case where the mutation is a nonsense mutation, nonsense-mediated mRNA decay (Literature: Brogna and Wen 2009, Nat. Structural Mol. Biol. 16: 107-113) may occur, and degradation of a transcript may thus occur. In view of this, the position of the nonsense mutation is preferably in Exon 1, Exon 2, and/or Exon 3, more preferably in Exon 1 and/or Exon 2. In a case where the mutation is the frame-shift mutation or the nonsense mutation, it is preferable that the mutation is located between a position about half the length of a gene and a 5' end of the gene. Specifically, it is preferable that the mutation occurs in Exon 1, Exon 2, and/or Exon 3. The closer to the 5' end the mutation is located, the shorter a normal part of a resulting protein is. Thus, the protein is more likely to become non-functional with respect to a virus.

In a case where the virus-resistant tobacco in accordance with an embodiment of the present invention has a mutation in a non-coding region, such a mutation does not affect an amino acid sequence of the encoded eIF(iso)4E protein or of the encoded eIF4E2 protein, but can alter a secondary structure of DNA or mRNA, alter a binding site for transcriptional or translational mechanism, or decrease a tRNA binding efficiency. Thus, a decrease in transcriptional level and a decrease in translational level can occur.

Alternatively, in a case where a G to A mutation occurs in a translation initiation codon ATG of the target gene, normal initiation of translation does not take place, and thus translation into a normal target protein does not occur. Further, in a case where the virus-resistant tobacco in accordance with an embodiment of the present invention has a mutation in a non-coding region at a 5' end, such a mutation can lead to the appearance of ATG (initiation codon) in a frame that is not a correct frame. This may cause a translation to be initiated from such an incorrect frame. In such a case, a normal target protein is not produced. For example, in a case where a mutagen is ethyl methane sulfonate (EMS) (described later), a G to A mutation in GTG or a C to T mutation in ACG occurs. This causes another ATG to appear. In a case where a frameshift occurs in such a situation, translation into a normal target protein does not occur.

In a case where a G to A mutation occurs in GT at a 5' end of an intron of each gene, or a G to A mutation occurs in AG at a 3' end of the intron of each gene, removal of the intron at a normal position does not occur, and thus translation into a normal protein does not occur.

In a case where transcription of an eIF(iso)4E gene or an eIF4E2 gene is suppressed, the amount of transcripts of the eIF(iso)4E gene or the eIF4E2 gene is preferably not more than 20%, more preferably not more than 10%, and even more preferably not more than 5% of that in a wild type. Further, in a case where translation of an eIF(iso)4E gene or an eIF4E2 gene is suppressed, the amount of translation products of the eIF(iso)4E gene or the eIF4E2 gene is preferably not more than 20%, more preferably not more than 10%, and even more preferably not more than 5% of that in a wild type.

Further, a mutation in an eIF(iso)4E gene may cause an abnormal splicing of RNA in the eIF(iso)4E gene. A mutation in an eIF4E2 gene may cause an abnormal splicing of RNA in the eIF4E2 gene. For example, in a case where a mutation(s) occur(s) in any of GT bases at a 5' end side of an intron and 10 bases upstream and downstream of the GT bases, preferably in any of GT bases at a 5' end side of an intron and 5 bases upstream and downstream of the GT bases, more preferably in any of GT bases at a 5' end side of an intron and one base upstream and downstream of the GT bases, or occurs in any of AG bases at a 3' end side of an intron and 10 bases upstream and downstream of the AG bases, preferably in any of AG bases at a 3' end side of an intron and 5 bases upstream and downstream of the AG bases, more preferably in any of AG bases at a 3' end side of an intron and one base upstream and downstream of the AG bases, intron splicing is unsuccessfully completed, and an abnormal mRNA occurs accordingly. This can (i) produce an eIF(iso)4E protein or an eIF4E2 protein which is non-functional with respect to a virus or (ii) suppress translation of the eIF(iso)4E gene or the eIF4E2 gene.

A method of inducing a mutation in a target gene is not limited to any specific method and can be a known method.

The mutagen can be any chemical agent that induces a mutation in a genomic DNA of tobacco. Such a chemical agent is exemplified by, but not limited to, ethyl methane sulfonate (EMS), sodium azide, ethidium bromide, and nitrous acid. Alternatively, the mutagen can be any radiation or the like that induces a mutation in a genomic DNA of tobacco. Such a radiation or the like is exemplified by, but not limited to, gamma rays, heavy ion beams, X-rays, neutron beams, and UV. The mutagen is preferably EMS.

Any type of tissues or organs of tobacco can be treated with the mutagen, provided that a plant body can be regenerated therefrom. Such tissues or organs are exemplified by, but not limited to, a seed, a root, a leaf, and a flower. A seed is preferably treated with the mutagen. With respect to mutagenesis population, a dosage of a mutagenic chemical agent or a radiation is empirically determined for each type of plant tissue so as to obtain a mutation frequency lower than a threshold level that leads to lethality or reproductive sterility.

Alternatively, the mutagen can be a transposon (movable genetic element). A transposon can be transferred in a tobacco genome to suppress the function of a target gene. A preferred example of such a transposon is exemplified by retrotransposon tnt1 of tobacco. Alternatively, a transposon of another plant can also be used by being introduced into tobacco. Such a transposon is exemplified by, but not limited to, transposons Ac/Ds, Spm/dSpm, and Mu of maize, transposon nDart of rice, and transposon tam of snapdragon.

Further alternatively, T-DNA in Ti plasmid of *Agrobacterium* can be inserted into tobacco at random to suppress the function of an eIF(iso)4E gene or an eIF4E2 gene. Thus, from a prepared tobacco mutant population (panel) with T-DNA inserted, an individual in which the function of the eIF(iso)4E gene or the eIF4E2 gene is suppressed can be selected with use of a base sequence of the eIF(iso)4E gene or the eIF4E2 gene as an index.

In an example of a method for producing a virus-resistant tobacco having a homozygous mutation in a target gene, tobacco is treated with a mutagen, as discussed above, to prepare a population (panel) of tobacco mutants with mutations in the whole tobacco genome, and genomic DNAs are extracted. By using gene-specific primers, the target gene is amplified from each genomic DNA of the panel, or from a pool of the genomic DNAs of the panel. Subsequently, base sequences of resulting products are determined, and a line having a mutation is then selected. The type of the mutation is preferably a mutation involving an amino acid mutation, or a nonsense mutation, and is more preferably a nonsense mutation. DNAs are extracted from plants cultivated from seeds of the selected line, and individuals having a homozygous mutation for the target gene are selected. The thus obtained line having homozygous gene mutations in the target gene is subjected to a virus assay to verify resistance. In so doing, analysis of expression of the target gene can be carried out by quantitative PCR or the like to determine a reduced amount of transcripts.

Thus, an aspect of a method for producing a virus-resistant tobacco can include at least one of the following steps of: preparing a population (panel) of tobacco mutants with mutations in the whole tobacco genome; extracting genomic DNAs; determining a base sequence of a target gene; selecting a line having a homozygous mutation; and carrying out a virus assay to verify resistance.

Further, for the purpose of removing a mutation(s) at a position(s) different from the target gene in DNA, a line which has been subjected to a mutation treatment can be crossed at any given timing with a line which has not been subjected to a mutation treatment.

Extraction of genomic DNA from a tobacco mutant can be carried out by a known method and can be carried out by using a commercially available extraction kit. Further, genomic DNA can be semi-purified genomic DNA or can be purified genomic DNA obtained through several purification steps.

A polynucleotide can be amplified by, for example, a PCR method, but can be amplified by any of other known gene amplification methods including, for example, a ligase chain reaction (LCR) method and a Loop-Mediated Isothermal Amplification (LAMP) method.

A primer sequence for amplifying each polynucleotide can be designed, for example, in the following manner. A primer can be designed for an S-type specific region and a T-type specific region identified from a result of analysis of homology between the base sequence represented by the base sequence of an eIF(iso)4E-S gene and a base sequence of an eIF(iso)4E-T gene. With use of such a primer, the S-type gene and the T-type gene can be independently amplified specifically from a tobacco genome in which an S-type genome and a T-type genome coexist. The same applies to an eIF4E2 gene. A target site for which each of the primers is designed can be selected from the S-type specific region or the T-type specific region, but is preferably an intron, a 5' untranslated region, or a 3' untranslated region. The length of each primer is preferably 15 bases to 30 bases and particularly preferably 17 bases to 25 bases. As long as the primer can serve as a primer for amplifying a sequence of a predetermined number of bases including a mutation site, the sequence of the primer can include one or more substitutions, deletions, and/or additions. Further, the primer can be labeled with, for example, a fluorescent substance or a radioactive substance, if necessary.

The length of each polynucleotide to be amplified can be any length that can be used by various detection methods (described later) and is, for example, 20 bases to 5000 bases, more preferably 50 bases to 2000 bases, even more preferably 100 bases to 700 bases, further more preferably 100 bases to 500 bases.

A method of detecting a mutation(s) is typically exemplified by, but not limited to, the following methods: (1) A method of detecting the presence or absence of a mutation(s) by directly reading a base sequence of each polynucleotide with use of, for example, a commercially available sequencer; and (2) A method of detecting the presence or absence of a mutation(s) by using a single strand conformation polymorphism (SSCP) method.

By identifying base sequences of (PCR) products which are amplified by primers specific to the target gene from a tobacco mutant in which a mutation has been detected by any of the above methods, it is possible to determine whether the mutation is a homozygous mutation or a heterozygous mutation.

In a case where the EMS treatment is carried out, most of mutations that occur in DNA are C to T mutations and G to A mutations. Thus, codons that can turn into stop codons when mutated by the EMS treatment (i.e., potential codons for nonsense mutation) are the following four types of codons: CAA (C appearing in the 1st site is substituted by T), CGA (C appearing in the 1st site is substituted by T), TGG (G appearing in the 2nd or 3rd site is substituted by A), and CAG (C appearing in the 1st site is substituted by T).

For example, in the case of the genomic sequence of the eIF4E2-S gene represented by SEQ ID NO: 3, a change to a termination codon (TAA, TAG, or TGA) occurs when there occurs (1) G to A substitution at position 389, (2) G to A substitution at position 390, (3) G to A substitution at position 398, (4) G to A substitution at position 399, (5) C to T substitution at position 427, (6) G to A substitution at position 437, (7) G to A substitution at position 438, (8) G to A substitution at position 488, (9) G to A substitution at position 489, (10) G to A substitution at position 3114, (11) G to A substitution at position 3115, (12) G to A substitution at position 3147, (13) G to A substitution at position 3148, (14) G to A substitution at position 3186, (15) G to A substitution at position 3187, (16) C to T substitution at position 3330, (17) C to T substitution at position 3375, (18) G to A substitution at position 3403, (19) G to A substitution at position 3404, (20) C to T substitution at position 3432, (21) C to T substitution at position 5121, (22) G to A substitution at position 5125, or (23) G to A substitution at position 5126. Thus, a preferred example of a virus-resistant tobacco has one or more of the above mutations (1) to (23) in the genomic sequence of the eIF4E2-S gene represented by SEQ ID NO: 3. Among these mutations, it is preferable that any of the mutations (1) to (22) occurs, and it is more preferable that any of the mutations (1) to (20) occurs.

In the case of the genomic sequence of the eIF4E2-T gene represented by SEQ ID NO: 6, a change to a termination codon (TAA, TAG, or TGA) occurs when there occurs (1) G to A substitution at position 1913, (2) G to A substitution at position 1914, (3) G to A substitution at position 1922, (4) G to A substitution at position 1923, (5) C to T substitution at position 1948, (6) G to A substitution at position 1958, (7) G to A substitution at position 1959, (8) G to A substitution at position 2009, (9) G to A substitution at position 2010, (10) G to A substitution at position 4722, (11) G to A substitution at position 4723, (12) G to A substitution at position 4755, (13) G to A substitution at position 4756, (14) G to A substitution at position 4794, (15) G to A substitution at position 4795, (16) C to T substitution at position 4936, (17) C to T substitution at position 4981, (18) G to A substitution at position 5009, (19) G to A substitution at position 5010, (20) C to T substitution at position 5038, (21) C to T substitution at position 6942, (22) G to A substitution at position 6946, or (23) G to A substitution at position 6947. Thus, a preferred example of a virus-resistant tobacco has one or more of the above mutations (1) to (23) in the genomic sequence of the eIF4E2-T gene represented by SEQ ID NO: 6. Among these mutations, it is preferable that any of the mutations (1) to (22) occurs, and it is more preferable that any of the mutations (1) to (20) occurs.

In the case of a genomic sequence of the eIF(iso)4E-S gene represented by SEQ ID NO: 9, a change to a termination codon (TAA, TAG, or TGA) occurs when there occurs (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, or (27) C to T substitution at position 4926. Thus, a preferred example of a virus-resistant tobacco has one or more of the above mutations (1) to (27) in the genomic sequence of the eIF(iso)4E-S gene represented by SEQ ID NO: 9. Among these mutations, it is preferable that any of the mutations (1) to (26) occurs, and it is more preferable that any of the mutations (1) to (24) occurs.

In the case of the genomic sequence of the eIF(iso)4E-T gene represented by SEQ ID NO: 12, a change to a termination codon (TAA, TAG, or TGA) occurs when there occurs (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, or (26) C to T substitution at position 3406. Thus, a preferred example of a virus-resistant tobacco has one or more of the above mutations (1) to (26) in the genomic sequence of the eIF(iso)4E-T gene represented by SEQ ID NO: 12. Among these mutations, it is preferable that any of the mutations (1) to (25) occurs, and it is more preferable that any of the mutations (1) to (23) occurs.

Alternatively, the mutation can be a mutation in (a) an exon of a wild-type eIF4E2 gene which encodes an eIF4E2 protein consisting of an amino acid sequence represented by SEQ ID NO: 2 or SEQ ID NO: 5, (b) an exon of a wild-type eIF4E2 gene which encodes a functional eIF4E2 protein having a sequence identity of 88% or higher with respect to the amino acid sequence represented by SEQ ID NO: 2 or SEQ ID NO: 5, (c) an exon of a wild-type eIF(iso)4E gene which encodes an eIF(iso)4E protein consisting of an amino acid sequence represented by SEQ ID NO: 8 or SEQ ID NO: 11, or (d) an exon of a wild-type eIF(iso)4E gene which encodes a functional eIF(iso)4E protein having a sequence identity of 92% or higher with respect to the amino acid sequence represented by SEQ ID NO: 8 or SEQ ID NO: 11. In the above exons, the mutation can be one or more of the following mutations (1) to (4): (1) a mutation in which C of codon CAA is substituted by T; (2) a mutation in which C of codon CGA is substituted by T; (3) a mutation in which C of codon CAG is substituted by T; and (4) a mutation in which G (either one or both of two Gs) of codon TGG is substituted by A.

As another means for causing a mutation in the target gene, a gene editing technique can be used. The gene editing technique is a technique of introducing a mutation into any region of genome. Examples of such a technique include TALEN (Transcription activator-like effector nuclease), CRISPR (Clustered regularly interspaced short palindromic repeat)/CAS, ODM (Oligonucleotide Directed Mutagenesis), and ZFN (Zinc Finger Nuclease).

The definitions of ODM and ZFN are described in Lusser et al. (2012) Nature Biotechnology 30: 231-239. As for ODM, its application to a plant is described in, for example, Zhu et al. (1999) Proc. Natl. Acad. Sci. USA 96: 8768-8773 and Oh and May (2001) Current Opinion in Biotechnology 12:169-172. As for ZFN, its application to a plant is described in Durai et al. (2005) Nucleic Acids Res 33: 5978-5990. In accordance with any of the methods described in these literatures, it is possible to introduce a mutation into the target gene.

An explanation of TALEN is as follows. A DNA-binding protein derived from a plant pathogen, transcription activator-like (TAL) effector, has a structural portion in which 34 amino acids are repeated. Each repeating structure recognizes one base of a DNA. Four types of bases (A, T, G, and C) are present in DNA, and binding specificity of a DNA sequence is determined by two amino acids (13th and 14th amino acids) in the repeating structure of the TAL effector. That is, by selecting the 13th and 14th amino acids in each of the repeating structures, it is possible to artificially bind the TAL effector to a desired region of a DNA. A fusion of the TAL effector with the enzyme FokI, which shows a DNA cleavage activity when it is a dimer, is referred to as TAL effector nuclease (TALEN). When two TALENs are so designed as to bind in close vicinity to each other, FokI forms a dimer to cleave a DNA that is present between the two TALENs. After the cleavage occurs, the DNA is repaired. During the repair, deletion or addition may occur to some extent at a site of the cleavage. TALENs have been found to function in plants (Literature: Zhang et al. (2013) Plant Physiology 161: 20-27).

For example, a nucleotide sequence which is specific to the target gene and has preferably 15 bases to 25 bases, more preferably 18 bases to 22 bases, is designed preferably for a protein coding region. Then, another nucleotide sequence is designed similarly for a place preferably 9 bases to 15 bases away from the previously designed nucleotide sequence. A portion flanked by these two nucleotides is supposed to be cut later.

In order to determine whether the nucleotide sequences thus designed are specific to the target gene, not only a sequence itself but also the presence or absence of a region having a high homology including that sequence can be determined by carrying out, for example, homology search of the designed nucleotide sequences with respect to a known sequence database of *N. tabacum*, alternatively *N. sylvestris* or *N. tomentosiformis*. Examples of the sequence database as used include GenBank, EMBL (The European Molecular Biology Laboratory), and DDBJ (DNA Data Bank of Japan). As a sequence analysis algorithm, for example, BLAST can be used. Types of database sequences are exemplified by, but not limited to, Nucleotide Collection (nr/nt), Expressed Sequence Tags (EST), Genomic survey sequences (GSS), and Whole genome shotgun contigs (WGS).

Based on the designed specific nucleotide sequence, a gene sequence of a TALE is designed. A plurality of repeating structures can be bound with use of a kit which is exemplified by, but not limited to, GoldenGateTALEN Kit (Addgene). In fusing the TALE and the FokI, a suitable linker sequence, for example can be arranged. Note that a sequence of the FokI is included in a known database. A promotor for expressing a TALE/FokI fusion gene in tobacco is preferably a promotor that achieves high-level expression. Such a promoter is exemplified by, but not limited to, constitutive expression promotors such as a promoter of a cauliflower mosaic virus 35S RNA gene, a promoter of an actin gene, and a promotor of a ubiquitin gene; green tissue specific promotors such as a promoter of a Rubisco small subunit gene and a promotor of a PPDK gene; and organ specific promotors and stage specific promotors. In order to increase an expression level, a desired intron can be arranged between the promotor and TALE/FokI. In order to further increase an expression level, codons of TALE/FokI can be optimized to be plant (tobacco) codons. The plant codons are listed in, for example, a known database such as Codon Usage Database www.kazusa.or.jp/codon/).

A vector for introducing a TALEN expression cassette into a plant can have incorporated thereinto not only the aforementioned cassette, but also an expression cassette of a drug resistance gene (selection marker) for selecting a plant cell into which the TALEN expression cassette is introduced. The drug resistance gene is any gene having resistance to a drug that allows a tobacco cell to be selected, and is exemplified by, but not limited to, a kanamycin resistance gene (neomycin phosphotransferase: NPT-II) and a hygromycin resistance gene (hygromycin phosphotransferase: HPT). Further, the promoter is not limited to any specific one, provided that it enables constitutive expression.

Furthermore, in a case where *Agrobacterium* is used to stably introduce the TALEN expression cassette into a plant, the TALEN expression cassette and the selection marker expression cassette need to be present in T-DNA. In this case, a right border (RB) sequence and a left border (LB) sequence, as boundary sequences of the T-DNA, are arranged at respective both ends of the T-DNA.

A vector for introducing the TALEN expression cassette into a plant, the vector enabling a gene to be introduced into tobacco, is exemplified by, but not limited to, a pBI vector and a pSB vector (Literature: Komari et al. 2006 Methods in Mol. Biol. 343: 15-41), a pLC vector (Literature: Specification of U.S. Pat. No. 8,298,819), and a pGreen vector (Literature: Hellens et al. 2000 Plant Mol. Biol. 42: 819-832).

A method of introducing the TALEN expression cassette into a plant is not limited to any specific method, and can be a method commonly employed by a person skilled in the art, such as the aforementioned method using *Agrobacterium*, a method using a particle gun, a PEG method, an electroporation method, or an agroinfiltration method. A tissue or organ of tobacco to be subjected to the introduction is not limited to any specific type of tissue or organ, provided that a plant body can be regenerated. Examples of such a tissue or organ include a seed, a root, a leaf, and a flower.

A transformed plant can be easily selected and easily cultivated by a person skilled in the art. A drug used for the selection is exemplified by, but not limited to, kanamycin and hygromycin. The concentration of the drug is, for example, 20 mg/mL to 200 mg/mL, preferably 50 mg/mL to 100 mg/mL. A medium for the cultivation of a plant culture can be a commonly-used medium. Examples of a type of inorganic salt include MS and LS. To the inorganic salt, sucrose, agar, plant hormone, or the like is added. A concentration at which such a substance is used can be determined in accordance with a protocol commonly used by a person skilled in the art.

As a tissue or organ to be subjected to gene introduction, not only the tissue or organ listed above, but also a protoplast can be used. The protoplast can be prepared by a usual method using a cell wall degrading enzyme. Further, as a gene introduction method, not only the aforementioned stable transformation method, but also a transient method can be employed. Transient assay can be carried out with use of an electroporation method, a PEG method, or other usual method. Another transient assay method is exemplified by, for example, agro-infiltration and a viral vector. The viral vector is exemplified by, but not limited to, ALSV (Apple latent spherical virus) and TRV (Tobacco rattle virus).

Whether or not the target gene is mutated in an individual, or in a tissue or organ, which has been regenerated from a transgenic cell can be determined by designing primers that flank a target region, extracting DNA from a desired plant tissue, amplifying that region by PCR or the like, and then examining a base sequence of a PCR product.

A method of analyzing gene expression is not limited to any specific one, and can be any of known methods including, for example, a northern hybridization method and a quantitative PCR method. A probe used in hybridization can be designed to have a base sequence of cDNA of the target gene or a part of that base sequence, or to have a base sequence in which one or more bases are substituted, deleted, or inserted in the base sequence of the cDNA or in the part thereof. The length of the probe can be, for example, 20 bases to a full length of the sequence.

Extraction of RNA for use in the expression analysis is carried out by a known method including, for example, a method using guanidine hydrochloride and an SDS-phenol method, and can be carried out with use of a commercially available kit. Total RNA can be purified to obtain mRNA (polyA+RNA).

Synthesis of cDNA for use in the quantitative PCR can be carried out by a known method using reverse transcriptase and either an oligo dT primer or a gene-specific primer, and can be carried out with use of a commercially available kit.

Further, a primer for quantitative PCR can be designed based on the base sequence of cDNA of the target gene. The length of the primer is preferably 15 bases to 30 bases, particularly preferably 17 bases to 25 bases. The length of a target sequence to be amplified by a set of primers is not limited to any specific length, and can be, for example, 40 bases to a full length of the sequence, preferably 50 bases to 500 bases.

In carrying out quantitative PCR using a fluorescent PCR apparatus, not only sequences of the primers, but also a sequence of a probe are set in a target sequence. The length of the target sequence is preferably 40 bases to 200 bases, more preferably 50 bases to 150 bases. A reporter dye for labeling the primers and the probe is exemplified by FAM, HEX, TET, and Cyanine5, and a quencher dye is exemplified by, for example, TAMRA and BHQ1. The reporter dye and the quencher dye are not limited to these dyes, and can be selected and combined as appropriate by a person skilled in the art. A gene used as an internal standard for quantitative PCR can be any constitutive expression gene. A preferable internal standard gene is exemplified by, for example, an elongation factor gene and an actin gene.

An explanation of CRISPR/CAS is as follows. The CRISPR/CAS system, which is a gene editing technique using (i) a guide RNA that recognizes a DNA sequence and (ii) CAS nuclease, is known to function in a plant (Literature: Belhaj et al. (2013) Plant Methods 9:39). This technique, which is a technique for cutting a DNA having a desired sequence on genome, relies, regarding deletion, addition, and insertion in a target genomic sequence, on mistakes made by a DNA repair system of a host, as is the case with TALEN.

A promotor for expressing CAS9 in a plant is preferably a promotor that achieves high-level expression. Such a promotor is exemplified by, but not limited to, the aforementioned promotor of a 35S RNA gene, the aforementioned promotor of a ubiquitin gene, and the aforementioned promotor of a PPDK gene. In order to increase an expression level, a desired intron can be arranged between the promoter and CAS9. Note that the base sequence of CAS9 is known. In order to further increase an expression level, codons of CAS9 can be optimized to be plant (tobacco) codons. Further, a nuclear localization signal (NLS) can be added to CAS9.

A desired genomic sequence and a complementary guide RNA are designed. For example, a nucleotide sequence which is unique to the target gene and has preferably 19 bases to 22 bases is determined, preferably for a protein coding region. In this case, at a 3' end side of that sequence, an NGG sequence called protospacer-adjacent motif (PAM) needs to be present. Further, in a case where the type of the promoter described later is U6, a transcription initiation point (5' end of a guide RNA) needs to be G. In a case where the type of the promoter is U3, the transcription initiation point needs to be A.

In order to determine whether the sequence of the guide RNA is specific to the target gene, not only a sequence itself but also the presence or absence of a region having a high homology including that sequence can be determined by carrying out, for example, homology search of the designed sequence through the sequence database of *N. tabacum*, alternatively *N. sylvestris* or *N. tomentosiformis*. The sequence database and the sequence analysis algorithm are similar to those discussed earlier.

After the guide RNA is designed, an sgRNA scaffold sequence is fused to a 3' end of the guide RNA to obtain an sgRNA (guide (g)RNA+gRNA scaffold), and a construct for expressing the sgRNA is then produced. At that time, a promoter including, for example, U6 and U3 of RNA polymerase III can be used as a promotor. The construct completed with use of a suitable vector is introduced into tobacco, a recombinant is selected, and regeneration is then carried out. In order to further ensure the occurrence of a mutation, a plurality of guide RNAs can be designed for a region within the target gene, and constructs for expressing the respective guide RNAs can be introduced into tobacco simultaneously. In this case, a plurality of guide RNA expression cassettes and a CAS9 expression cassette can be arranged on one T-DNA simultaneously.

Note that a vector for introducing, into a plant, a cassette that enables expression of a guide RNA and CAS9 and a method of tobacco transformation are similar to those explained earlier for TALEN.

As a tissue or organ to be subjected to gene introduction, not only the tissue or organ listed above, but also a protoplast can be used. The protoplast can be prepared by a usual method using a cell wall degrading enzyme. Further, as a gene introduction method, not only the aforementioned stable transformation method, but also a transient method can be employed. Transient assay is similar to that explained earlier for TALEN.

Whether or not the target gene is mutated in an individual, or in a tissue or organ, which has been regenerated from a transgenic cell can be determined by a method similar to that explained earlier for TALEN.

A virus assay method is exemplified by, but not limited to, a mechanical inoculation method using a combination of a virus solution and solid powder such as carborundum and an insect inoculation method using a viruliferous aphid. The virus used is not limited to any specific virus, and can be any of the viruses listed above as the virus to which a virus-resistant tobacco has resistance.

A method of producing a virus-resistant tobacco having both a mutation in an eIF(iso)4E gene and a mutation in an eIF4E2 gene is not particularly limited. Examples of such a method include: a method which utilizes crossbreeding between a virus-resistant tobacco having a mutation in the eIF(iso)4E gene and a virus-resistant tobacco having a mutation in the eIF4E2 gene; a method in which a mutation is introduced into an eIF4E2 gene in a virus-resistant tobacco having a mutation in an eIF(iso)4E gene; a method of introducing, into a virus-resistant tobacco having a mutation in an eIF(iso)4E gene, a factor that reduces the expression level of an eIF4E2 gene; a method of introducing a mutation into an eIF(iso)4E gene in a virus-resistant tobacco having a mutation in an eIF4E2 gene; and a method of introducing, into a virus-resistant tobacco having a mutation in an eIF4E2 gene, a factor that reduces the expression level of an eIF(iso)4E gene.

It is possible to use the mutant, disclosed in Patent Literature 5, as a tobacco mutant in which the function of an S-type eIF(iso)4E gene, the function of a T-type eIF(iso)4E gene, or both of these functions is/are suppressed.

In the present embodiment, the "virus-resistant tobacco" encompasses not only tobacco produced and selected as described above, but also tobacco that is an offspring (progeny) of the tobacco.

(Aspect 2 of virus-resistant tobacco) In an aspect, the expression of a translation initiation factor eIF(iso)4E gene is suppressed in a virus-resistant tobacco by introducing, into the tobacco, a factor that causes the translation initiation factor eIF(iso)4E gene to be expressed at a lower level than a wild type.

Alternatively, expression of a translation initiation factor eIF4E2 gene is suppressed by introducing, into the tobacco, a factor that causes the translation initiation factor eIF4E2 gene to be expressed at a lower level than a wild type.

Alternatively, both (i) the factor that causes the translation initiation factor eIF(iso)4E gene to be expressed at a lower level than a wild type and (ii) the factor that causes the translation initiation factor eIF4E2 to be expressed at a lower level than a wild type are introduced into the tobacco.

For a method of causing a target gene to be expressed at a lower level than a wild type, any of known methods in the art can be employed, including, for example, a method using antisense, a method using cosuppression, a method using RNA interference (RNAi), a method using microRNA, a method using virus induced gene silencing (VIGS), a method using ribozymes, a method using homologous recombination, and a method using expression of dominant negative gene products.

Herein, the intended meaning of "causing a gene to be expressed at a lower level than a wild type" is not limited as long as a decrease in expression is achieved as compared with the wild type. However, the expression level is preferably decreased to not more than 20%, more preferably not more than 10%, and even more preferably not more than 5% of the expression level (100%) of the wild type. Here, the "wild type" refers to tobacco into which a factor that suppresses expression of a target gene has not been introduced and in which the target gene is not mutated.

In the present embodiment, the "virus-resistant tobacco" encompasses not only original-generation tobacco into which the factor or the like is introduced, but also tobacco that is an offspring (progeny) of the original-generation tobacco.

A method of suppressing expression of the target gene is preferably RNAi. Specifically, an RNAi construct is prepared by using, as a trigger, a base sequence of the target gene (eIF(iso)4E gene or eIF4E2 gene) or a part of that base sequence. The RNAi construct thus prepared is connected to a promotor that causes expression in a plant, and then introduced into tobacco by using a vector. Thus, a virus-resistant tobacco is obtained in which the RNAi construct is expressed to suppress expression of the target gene. Therefore, a virus-resistant tobacco according to an aspect can retain an RNAi construct for suppressing expression of the target gene.

The length of the trigger can be, for example, 21 bases to a full length of the sequence, but is preferably 50 bases or more, more preferably 100 bases or more. A trigger sequence can be such that one or more bases are substituted, deleted, or inserted.

By using, as a trigger sequence, a part of a base sequence in which the S-type gene and the T-type gene have a high degree of identity, it is possible to use one kind of RNAi construct to suppress expression of both the S-type gene and the T-type gene. In other words, for example, in a case where the trigger of the introduced RNAi construct is a sequence of an eIF(iso)4E-S gene, and the sequence of the trigger has a high degree of identity with the sequence of an eIF(iso)4E-T gene, it is possible to suppress not only expression of the eIF(iso)4E-S gene, but also suppression of the eIF(iso)4E-T gene. The same applies to an eIF4E2 gene.

In RNAi, an RNAi construct is prepared such that an inverted repeat sequence is achieved by functionally linking a first trigger sequence and a second trigger sequence so that the first trigger sequence extends in a sense direction and the second first trigger sequence extends in an antisense direction. In preparation of the RNAi construct, a spacer sequence is preferably provided between both of the triggers. Such a spacer sequence is preferably a sequence that is not contained in a tobacco genome or a region, such as an intron sequence, that is not contained in mature mRNA. Such a sequence is exemplified by, but not limited to, intron sequences of β-glucuronidase (GUS) gene, pyruvate dehydrogenase kinase (pdk) gene, and catalase (cat) gene.

A promotor for causing transcription of the RNAi construct in a plant is exemplified by, but not limited to, constitutive expression promotors such as a promoter of a cauliflower mosaic virus 35S RNA gene, a promoter of an actin gene, and a promotor of a ubiquitin gene; green tissue specific promotors such as a promotor of a Rubisco small subunit gene and a promotor of a PPDK gene; and organ specific promotors and stage specific promotors. The promotor is preferably a promotor that causes expression in a tissue which a virus infects.

A terminator can be any terminator that functions in a plant. The terminator is exemplified by, but not limited to, a terminator of a cauliflower mosaic virus 35S RNA gene, a terminator of a cauliflower mosaic virus 19S RNA gene, and a terminator of a nopaline synthetase gene.

A vector for introducing an RNAi expression cassette into a plant can have incorporated thereinto not only the aforementioned cassette, but also an expression cassette of a drug resistance gene for selecting a plant cell into which the RNAi expression cassette is introduced. The drug resistance gene is any gene having resistance to a drug that allows a tobacco cell to be selected, and is exemplified by, but not limited to, a kanamycin resistance gene (neomycin phosphotransferase: NPT-II) and a hygromycin resistance gene (hygromycin phosphotransferase: HPT). Further, the promoter is not limited to any specific one, provided that it enables constitutive expression.

Furthermore, in a case where *Agrobacterium* is used to stably introduce the RNAi expression cassette into a plant, the RNAi expression cassette and the selection marker expression cassette need to be present in T-DNA. In this case, a right border (RB) sequence and a left border (LB) sequence, as boundary sequences of the T-DNA, are arranged at respective both ends of the T-DNA.

Further, in order to visually predict gene expression, an expression cassette of a fluorescent protein can be arranged in the T-DNA. The fluorescent protein is exemplified by, but not limited to, green fluorescent protein (GFP) and yellow fluorescent protein (YFP). The fluorescent protein is preferably GFP. Fluorescence can be observed by an image analyzer.

A vector for introducing the RNAi expression cassette into a plant, the vector enabling a gene to be introduced into tobacco, is exemplified by, but not limited to, pBI vectors and pSB vectors (Literature: Komari et al. 2006 Methods in Mol. Biol. 343: 15-41), pLC vectors (Literature: Specification of U.S. Pat. No. 8,298,819), a pGreen vector (Literature: Hellens et al. 2000 Plant Mol. Biol. 42: 819-832), a pHellsgate vector (Literature: Wesley et al. 2001 Plant J 27: 581-590), and a pSP231 vector (Literature: International publication No. WO 2011/102394).

A method of introducing the RNAi expression cassette into a plant is not limited to any specific method, and can be a method commonly employed by a person skilled in the art, such as the aforementioned method using *Agrobacterium*, a method using a particle gun, a PEG method, an electroporation method, or an agroinfiltration method. A tissue or organ of tobacco to be subjected to the introduction is not limited to any specific type of tissue or organ, provided that a plant body can be regenerated. Examples of such a tissue or organ include a seed, a root, a leaf, and a flower.

A transformed plant can be easily selected and easily cultivated by a person skilled in the art. A drug used for the selection is exemplified by, but not limited to, kanamycin and hygromycin. The concentration of the drug is, for example, 20 mg/mL to 200 mg/mL, preferably 50 mg/mL to 100 mg/mL. A medium for the cultivation of a plant culture can be a commonly-used medium. Examples of a type of inorganic salt include MS and LS. To the inorganic salt, sucrose, agar, plant hormone, or the like is added. A concentration at which such a substance is used can be determined in accordance with a protocol commonly used by a person skilled in the art.

A method of analyzing gene expression and a virus assay method are as discussed earlier.

It will be easily understood by a person skilled in the art that the virus-resistant tobacco can involve a combination of Aspects 1 and 2 described above. In other words, in another aspect, with regards to a first one of the target genes, the virus-resistant tobacco can have a mutation in the first one of the target genes, the mutation (i) causing production of a protein which is non-functional with respect to a virus or (ii) suppressing expression of the first one of the target genes, and with regards to a second one of the target genes, an expression level of the second one of the target genes can be suppressed by introducing, into the tobacco, a factor which causes the second one of the target genes to be expressed at a lower level than a wild type.

Alternatively, a tobacco variety, line, or domestic cultivar which is thought to exhibit deletion of the function of any one of the target genes can be used and combined with Aspect 1 or Aspect 2. Such a tobacco variety, line, or domestic cultivar is exemplified by a tobacco variety, line, or domestic cultivar which is thought to exhibit deletion of, for example, the function of the S-type eIF4E2 gene and is exemplified by, but not limited to, Virgin A Mutant, Perevi, SCR, Bursana, Kerti, Havana 211, Enshu, Okinawa 1, TN86, TN90, TN97, K326 PVY, NC291, and NC745. Such a tobacco variety, line, or domestic cultivar is also exemplified by, but not limited to, a tobacco plant which is described in non-patent literature Yamamoto, Y. ((1992) Studies on Breeding of Tobacco Varieties Resistant to Veinal Necrosis Disease by Potato virus Y Strain T. Bulletin of the Leaf Tobacco Research Laboratory, 1-87) and which is tobacco in which the S-type eIF4E2 gene itself is deleted or the S-type eIF4E2 gene has been subjected to base deletion, base substitution, or base insertion. Note that the term "gene" as used here encompasses not only a protein-coding region, but also a promotor, an intron, and a terminator. Whether or not the gene itself has been deleted, or whether or not there is a deletion, substitution, or insertion in the gene can be determined by (i) designing, in accordance with the base sequence of the target gene, a primer such that, for example, the entire length of the gene or a part thereof is amplified, and (ii) then carrying out PCR, using as a template the DNA of the tobacco to be examined. For example, in a case where a product is not amplified, it can be determined that the gene itself has been deleted. In a case where the product is amplified, the base sequence of the product can be read to easily determine whether or not there is a base deletion, substitution, or insertion.

In production of leaf tobacco, a genetic resource which provides resistance to a plurality of viruses simultaneously is of extreme importance. Unfortunately, to date, there has been no known tobacco which is resistant to all of PVY, PVY-B, and TBTV. An aspect of the virus-resistant tobacco in accordance with the present embodiment makes it possible to provide a virus-resistant tobacco having resistance to all of PVY, PVY-B, and TBTV.

[2. Method for Producing Bred Progeny of Virus-Resistant Tobacco]

An embodiment of the present invention also provides a method for producing a breeding progeny of a virus-resistant tobacco.

An aspect of the method involves self-pollination or cross-pollination of (i) a virus-resistant tobacco produced by the aforementioned method for producing a virus-resistant tobacco or (ii) a progeny of the virus-resistant tobacco thus produced. The pollination can be conducted naturally or artificially. In an embodiment, the progeny can be obtained by self-pollinating or cross-pollinating an original-generation virus-resistant tobacco produced through the aforementioned method for producing a virus-resistant tobacco, or by further repeating self-pollination or cross-pollination of a progeny thus obtained.

In cross-pollination, the virus-resistant tobacco or a progeny thereof can be crossed with a virus-resistant tobacco that has the same mutation in each gene, a virus-resistant tobacco that has a different mutation in each gene, tobacco that has no mutation in each gene, or tobacco that does have a mutation in each gene but does not have resistance to a virus.

An aspect of the method makes it possible to obtain tobacco of a bred progeny such as a filial generation ($F_1$, $F_2$, . . . ), a selfed generation of a mutant ($M_1$, $M_2$, . . . ), or a backcrossed generation ($BC_1$, $BC_2$, . . . ). Such tobacco can have male sterility (MS).

An embodiment of the present invention also provides a method for breeding a virus-resistant tobacco, including self-pollinating or cross-pollinating (i) a virus-resistant tobacco produced by the aforementioned method for producing a virus-resistant tobacco or (ii) a progeny of the virus-resistant tobacco produced. An aspect of the method is exemplified by, but not limited to a method in which a virus-resistant tobacco individual having a mutation in an eIF(iso)4E gene or an eIF4E2 gene is obtained by the aforementioned method for producing a virus-resistant tobacco, and then the virus-resistant tobacco individual is crossed with a tobacco variety or a tobacco line to produce a first filial generation F1. To F1, the tobacco variety or the tobacco line is backcrossed to produce BC1F1. While selecting an individual having the mutation, crossing (backcrossing) of the individual with the tobacco variety or the tobacco line is further repeated to produce BCXF1 (where X is, for example, 3 to 8). Subsequently, BCXF1 is selfed to produce a BCXF2 generation, where an individual having the mutation homozygously is selected. For the purpose of fixing the genetic background, selfing is further repeated (BCXF3, BCXF4, . . . ) to breed a novel virus-resistant tobacco. Note that an individual of each generation can be selected with use of a DNA marker (described later).

[3. DNA Marker and Use Thereof]

According to an embodiment of the present invention, a DNA marker can be developed by using the mutation that occurs on an eIF4E2 gene (eIF4E2-S gene or eIF4E2-T gene), and the DNA marker can be utilized for marker breeding. The "DNA marker" refers to a difference in DNA base sequence (mutation or polymorphism) between varieties or individuals or a tool for detecting the difference, and also refers to a difference in DNA base sequence (mutation or polymorphism) which serves as a marker for discriminating varieties or individuals from each other or a tool for detecting the difference. In a case where a mutation in an eIF4E2 gene is determined, and it is determined that the mutation renders tobacco resistant to a virus, a tobacco mutant having that mutation can be used as a breeding mother plant having that virus resistance. Further, since the mutation responsible for the resistance has been already found, it is possible to design, on an eIF4E2 gene, a marker which can be used for identification of the mutation responsible for the resistance. Since a relation between that mutation and the virus resistance will never be broken by genetic segregation, it is possible to carry out precise marker breeding. Detection of the presence or absence of this mutation eliminates a need to determine virus resistance after each repetition of crossbreeding or the like breeding.

The DNA marker for the eIF4E2 gene can be used in conjunction with a similar DNA marker for the eIF(iso)4E gene. Such combined use of the markers for both of those genes makes it possible to reduce the time and effort required for breeding.

Extraction of genomic DNA from tobacco can be carried out by a usual method, and can be carried out by using a commercially available extraction kit, which is not particularly limited. Further, genomic DNA can be semi-purified genomic DNA or can be purified genomic DNA obtained through several purification steps. The presence or absence of a mutation can be detected by any technique that enables detection of the presence or absence of a mutation. Examples of such a technique include a technique to which nucleic acid (also referred to as a "polynucleotide") hybridization using RFLP or a single-stranded DNA as a probe is applied, and a technique (e.g., PCR) involving amplification of a polynucleotide.

A polynucleotide can be amplified by not only, for example, a PCR method but also any of other known gene amplification methods including, for example, an LCR method, a Strand Displacement Amplification (SDA) method, and a LAMP method. The length of each polynucleotide to be amplified can be any length that can be used by various detection methods (described later) and is, for example, preferably 40 bases to 5000 bases, more preferably 100 bases to 1000 bases, even more preferably 100 bases to 700 bases, further more preferably 100 bases to 500 bases.

A primer sequence for amplifying each polynucleotide is preferably designed so as to flank or contain a mutation site. However, the position at which the primer sequence is designed is not limited to any specific position. In a case where the primer sequence is designed so as to flank a mutation site, the primer sequence can be designed, for example, to be located within an eIF4E2 gene. The length of each primer is preferably 15 bases to 30 bases and particularly preferably 17 bases to 25 bases. As long as the primer can serve as a primer for amplifying a sequence of a predetermined number of bases including a mutation site, the sequence of the primer can include one or more substitutions, deletions, and/or additions. Further, the primer can be labeled with, for example, a fluorescent substance or a radioactive substance, if necessary.

The mutation to be detected is a mutation that causes production of an eIF4E2 protein which is non-functional with respect to a virus, or a mutation that suppresses expression of an eIF4E2 gene. Specific examples of the mutation are as discussed in [1. Virus-resistant tobacco].

A method of detecting a mutation(s) is typically exemplified by, but not limited to, the following methods.

(1) A method of detecting the presence or absence of a mutation(s) by directly reading base sequence of an amplified polynucleotide with use of, for example, a commercially available sequencer.

(2) A method of detecting the presence or absence of a mutation(s) in an amplified polynucleotide by using a single strand conformation polymorphism (SSCP) method.

(3) A method of treating an amplified polynucleotide with a restriction enzyme that specifically recognizes a sequence of a mutation site (a sequence which has not been subjected to or has been subjected to a mutation), and then determining the presence or absence of cleavage (Cleaved Amplified Polymorphic Sequence (CAPS) method). Another method that can be employed is a derived CAPS (dCAPS) method of using a primer set containing an intentionally designed mismatch primer to produce a restriction enzyme recognition site. A person skilled in the art can design a primer sequence, carry out PCR, and detect an intended mutation, without the need for much effort. For example, the primer sequence can be designed via the web (Literature: Neff et al. (2002) Web-based primer design for single nucleotide polymorphism analysis. TRENDS in Genetics 18: 613-615).

Note that in a case where a DNA polymerase having proofreading activity is used to carry out PCR with respect to primers containing a mismatch near a 3' end of one of the primers, the mismatch may be corrected, which prevents cleavage by the restriction enzyme. Thus, in a case where a mismatch primer is used in the dCAPS method, DNA polymerase having no proofreading activity is preferably used. Such DNA polymerase is exemplified by, but not limited to, TaKaRa Taq™ (Takara-Bio Inc.). Further, in a case where a restriction enzyme cleavage site is provided near the 3' end of the primer, the presence or absence of cleavage is detected as a difference in primer length.

(4) A method of designing a probe to hybridize specifically with a mutation site, and hybridizing the probe so as to determine the presence or absence of a mutation.

An analysis process is not limited to any specific one. For example, PCR carried out by a TaqMan (registered trademark) probe method, MassARRAY (registered trademark) analysis which is a measurement technique using TOF-MS, or the like can be used.

(5) A method of designing a primer sequence which contains, as a part thereof, a sequence of a mutation site (sequence which has not been subjected to and/or has been subjected to a mutation), and amplifying a polynucleotide by, for example, a PCR method so as to detect the presence or absence of a mutation in accordance with the presence or absence of amplification (allele-specific PCR method). For example, a nucleic-acid primer consisting of a base sequence specific to the base sequence before the mutation occurs can be used as a control.

In a case where a base corresponding to a target mutation is to be provided near a 3' end of a primer, that base is preferably provided at the end of the primer or at any of positions corresponding to several bases near the end of the primer. Further, in a case where a target mutation is provided near the 3' end of the primer, not only a sequence of a mutant type but also a sequence of a wild type having no mutation may be amplified. In such a case, a mismatch different from a target mismatch can be introduced into each of a primer for mutant-type detection and a primer for wild-type detection at an identical position, so that PCR is carried out to obtain mutant type-specific or wild type-specific amplification.

In addition to primers for a target gene, primers for a gene that serves as an internal standard of PCR can be added to a PCR reaction solution, if necessary.

Note that, in a case where a mutation different from the mutations listed above is to be detected, a person skilled in the art can design a primer sequence, carry out PCR, and detect an intended mutation, without the need for much effort.

Note that a gene mutation detection technique is detailed in the following literature: the web site of the Japan Patent Office: wwwjpo.go.jp/shiryou/s_sonota/hyoujun_gijutsu/kakusan/0025.html. Further, gene mutation detection and analysis methods are detailed in the following literature: the website of the Japan Patent Office: wwwjpo.go.jp/shiryou/s_sonota/hyoujun_gijutsu/kakusan/0028.html. Alternatively, reference can be made to the following literature: Agarwal et al. (2008): Advances in molecular marker techniques and their applications in plant sciences. Plant Cell Rep. 27:617-631; and Neff et al. (1998): dCAPS, a simple technique for the genetic analysis of single nucleotide polymorphisms: experimental applications in *Arabidopsis thaliana* genetics. Plant J. 14: 387-392.

Thus, an embodiment of the present invention provides a polynucleotide for detecting a mutation in an eIF4E2 gene. The mutation is a mutation that causes production of an eIF4E2 protein which is non-functional with respect to a virus, or a mutation that suppresses expression of the eIF4E2 gene. Specific examples of the mutation are as discussed in [1. Virus-resistant tobacco].

Further, an aspect of the detection polynucleotide is a nucleic-acid primer or a set of nucleic-acid primers. The set of nucleic-acid primers can be a set of nucleic-acid primers flanking the mutation, or a set of nucleic-acid primers which contains a polynucleotide consisting of a continuous base sequence which contains the mutation or a sequence complementary to the continuous base sequence. Another aspect of the detection polynucleotide is a nucleic-acid probe that hybridizes with a continuous base sequence which contains the mutation, or a sequence complementary to the continuous base sequence.

The above detection polynucleotide for the eIF4E2 gene can be used in combination with a similar detection polynucleotide for the eIF(iso)4E gene. Such combined use of the detection polynucleotide for the eIF4E2 gene and the detection polynucleotide for the eIF(iso)4E gene makes it possible to detect mutations in both of those genes simultaneously, and consequently makes it possible to reduce the time and effort required for breeding. Note that the detection polynucleotide disclosed in Patent Literature 5 can be used as the detection polynucleotide for the eIF(iso)4E gene.

How such combination is carried out is not particularly limited. The combination can be achieved, for example, by providing the detection polynucleotides in a pre-mixed state, or by a kit in which the detection polynucleotides are provided separately in respective containers and then combined by a user of the kit immediately before the kit is used.

An embodiment of the present invention also provides a determination method of determining whether tobacco is resistant to a virus, the method using, as an index of virus resistance, occurrence of the mutations in the eIF(iso)4E gene and the eIF4E2 gene in genomic DNA of tobacco.

An embodiment of the present invention also provides a method for breeding a virus-resistant tobacco, the method including a selection step of selecting, by using the determination method, tobacco having resistance to a virus.

An embodiment of the present invention also provides a method for selecting a virus-resistant tobacco, including: an examination step of examining tobacco for presence or absence of a mutation in genomic DNA by using the aforementioned detection polynucleotide; and a selection step of selecting, as the virus-resistant tobacco, tobacco in which the mutation has been detected in the examination step. Details of an examination method using a detection polynucleotide are as discussed earlier.

An embodiment of the present invention also provides a DNA marker for determining whether tobacco is resistant to a virus, the DNA marker containing: a polynucleotide consisting of a continuous base sequence which contains the above-described mutation in an eIF(iso)4E gene or of a sequence complementary to the continuous base sequence; and a polynucleotide consisting of a continuous base sequence which contains the above-described mutation in an eIF4E2 gene or of a sequence complementary to the continuous base sequence.

[4. Leaf Tobacco and Tobacco Product]

Leaf tobacco produced through cultivation of a virus-resistant tobacco of an embodiment of the present invention does not suffer from a disease caused by the virus (for example, the PVY strain that breaks virus resistance of Virgin A mutant). Therefore, such leaf tobacco is less deteriorated and is of a higher quality, as compared with leaf tobacco produced from a virus non-resistant tobacco which has been cultivated particularly in an environment where the disease may break out. As a result, it is possible to produce a tobacco product of higher quality.

The term "leaf tobacco" refers to dried leaves which are obtained by drying harvested fresh leaves of a tobacco plant, and which are a material for production of a tobacco product. The term "tobacco product" refers to, for example, cigarettes (with a filter and without a filter), cigars, cigarillos, snus, snuff, chewing tobacco, and electronic tobacco.

Thus, an embodiment of the present invention provides leaf tobacco which is produced from the virus-resistant tobacco. Further, an embodiment of the present invention provides a method for producing leaf tobacco, the method including a step of drying harvested fresh leaves of the virus-resistant tobacco.

An embodiment of the present invention also provides a tobacco product containing the leaf tobacco as a material.

[5. Recap]

As described earlier, an aspect of a virus-resistant tobacco in accordance with the present invention is arranged such that: (i) a translation initiation factor eIF(iso)4E protein which is non-functional with respect to a virus is produced or (ii) expression of a translation initiation factor eIF(iso)4E gene is suppressed; and (a) a translation initiation factor eIF4E2 protein, which is non-functional with respect to a virus, is produced or (b) expression of a translation initiation factor eIF4E2 gene is suppressed, the translation initiation factor eIF(iso)4E being at least one of eIF(iso)4E-S and eIF(iso)4E-T, and the translation initiation factor eIF4E2 being at least one of eIF4E2-S and eIF4E2-T.

An aspect of the virus-resistant tobacco in accordance with the present invention can be arranged such that the virus-resistant tobacco has a mutation in the translation initiation factor eIF(iso)4E gene, the mutation (i) causing production of the translation initiation factor eIF(iso)4E protein which is non-functional with respect to a virus or (ii) suppressing expression of the translation initiation factor eIF(iso)4E gene.

An aspect of the virus-resistant tobacco in accordance with the present invention can be arranged such that the virus-resistant tobacco has a mutation in the translation initiation factor eIF4E2 gene, the mutation (i) causing production of the translation initiation factor eIF4E2 protein which is non-functional with respect to a virus or (ii) suppressing expression of the translation initiation factor eIF4E2 gene.

An aspect of the virus-resistant tobacco in accordance with the present invention is preferably arranged such that the mutation is a nonsense mutation.

An aspect of the virus-resistant tobacco in accordance with the present invention can be arranged such that:
the mutation in the translation initiation factor eIF(iso)4E gene is
  a mutation in an eIF(iso)4E-S gene, which mutation is a nonsense mutation in
  (a1) an exon of a wild-type translation initiation factor eIF(iso)4E-S gene which encodes a translation initiation factor eIF(iso)4E-S protein consisting of an amino acid sequence represented by SEQ ID NO: 8 or
  (a2) an exon of a wild-type translation initiation factor eIF(iso)4E-S gene which encodes a functional translation initiation factor eIF(iso)4E-S protein having a sequence identity of 92% or higher with respect to the amino acid sequence represented by SEQ ID NO: 8;
  a mutation in an eIF(iso)4E-T gene, which mutation is a nonsense mutation in
  (b1) an exon of a wild-type translation initiation factor eIF(iso)4E-T gene which encodes a translation initiation factor eIF(iso)4E-T protein consisting of an amino acid sequence represented by SEQ ID NO: 11 or
  (b2) an exon of a wild-type translation initiation factor eIF(iso)4E-T gene which encodes a functional translation initiation factor eIF(iso)4E-T protein having a sequence identity of 92% or higher with respect to the amino acid sequence represented by SEQ ID NO: 11; or
  both the mutation in the eIF(iso)4E-S gene and the mutation in the eIF(iso)4E-T gene.

An aspect of the virus-resistant tobacco in accordance with the present invention can be arranged such that:
the mutation in the translation initiation factor eIF4E2 gene is
  a mutation in an eIF4E2-S gene, which mutation is a nonsense mutation in
  (c1) an exon of a wild-type translation initiation factor eIF4E2-S gene which encodes a translation initiation factor eIF4E2-S protein consisting of an amino acid sequence represented by SEQ ID NO: 2 or
  (c2) an exon of a wild-type translation initiation factor eIF4E2-S gene which encodes a functional translation initiation factor eIF4E2-S protein having a sequence identity of 88% or higher with respect to the amino acid sequence represented by SEQ ID NO: 2;
  a mutation in an eIF4E2-T gene, which mutation is a nonsense mutation in
  (d1) an exon of a wild-type translation initiation factor eIF4E2-T gene which encodes a translation initiation factor eIF4E2-T protein consisting of an amino acid sequence represented by SEQ ID NO: 5 or
  (d2) an exon of a wild-type translation initiation factor eIF4E2-T gene which encodes a functional translation initiation factor eIF4E2-T protein having a sequence identity of 88% or higher with respect to the amino acid sequence represented by SEQ ID NO: 5; or
  both the mutation in the eIF4E2-S gene and the mutation in the eIF4E2-T gene.

An aspect of the virus-resistant tobacco in accordance with the present invention is preferably arranged such that the nonsense mutation is one or more of the following mutations (1) through (4): (1) a mutation in which C of codon CAA is substituted by T; (2) a mutation in which C of codon CGA is substituted by T; (3) a mutation in which C of codon CAG is substituted by T; and (4) a mutation in which G (either one or both of two Gs) of codon TGG is substituted by A.

An aspect of the virus-resistant tobacco in accordance with the present invention is preferably arranged such that the mutation in the translation initiation factor eIF4E2 gene includes a mutation in an eIF4E2-S gene.

An aspect of the virus-resistant tobacco in accordance with the present invention is preferably arranged such that the mutation in the translation initiation factor eIF(iso)4E gene includes a mutation in an eIF(iso)4E-T gene.

An aspect of the virus-resistant tobacco in accordance with the present invention can be arranged such that the virus is a virus belonging to the genus *Potyvirus*.

An aspect of the virus-resistant tobacco in accordance with the present invention can be arranged such that the virus belonging to the genus *Potyvirus* is at least one of (i) a strain of Potato virus Y which strain breaks virus resistance of Virgin A mutant of tobacco and (ii) the Potato virus Y.

An aspect of the virus-resistant tobacco in accordance with the present invention can be arranged such that the virus-resistant tobacco further has resistance to a virus belonging to the genus *Umbravirus*.

An aspect of the virus-resistant tobacco in accordance with the present invention can be arranged such that the virus belonging to the genus *Umbravirus* is Tobacco bushy top virus.

An aspect of a method in accordance with the present invention for producing a virus-resistant tobacco includes the step of: producing tobacco resistant to a virus by (i) introducing a mutation into a translation initiation factor eIF(iso)4E gene, the mutation (a) causing production of a translation initiation factor eIF(iso)4E protein which is non-functional to a virus or (b) suppressing expression of the translation initiation factor eIF(iso)4E gene, and (ii) introducing a mutation into a translation initiation factor eIF4E2 gene, the mutation (c) causing production of a translation initiation factor eIF4E2 protein, which is non-functional with respect to a virus, or (d) suppressing expression of the translation initiation factor eIF4E2 gene, the translation initiation factor eIF(iso)4E being at least one of eIF(iso)4E-S and eIF(iso)4E-T, and the translation initiation factor eIF4E2 being at least one of eIF4E2-S and eIF4E2-T.

An aspect of the method in accordance with the present invention can be arranged such that the mutation is a nonsense mutation.

An aspect of the method in accordance with the present invention can be arranged such that the mutation is caused by ethyl methane sulfonate.

An aspect of the method in accordance with the present invention can be arranged such that: the mutation in the translation initiation factor eIF(iso)4E gene is a mutation in an eIF(iso)4E-S gene, which mutation is a nonsense mutation in (a1) an exon of a wild-type translation initiation factor eIF(iso)4E-S gene which encodes a translation initiation factor eIF(iso)4E-S protein consisting of an amino acid sequence represented by SEQ ID NO: 8 or (a2) an exon of a wild-type translation initiation factor eIF(iso)4E-S gene which encodes a functional translation initiation factor eIF(iso)4E-S protein having a sequence identity of 92% or higher with respect to the amino acid sequence represented by SEQ ID NO: 8;

a mutation in an eIF(iso)4E-T gene, which mutation is a nonsense mutation in (b1) an exon of a wild-type translation initiation factor eIF(iso)4E-T gene which encodes a translation initiation factor eIF(iso)4E-T protein consisting of an amino acid sequence represented by SEQ ID NO: 11 or (b2) an exon of a wild-type translation initiation factor eIF(iso)4E-T gene which encodes a functional translation initiation factor eIF(iso)4E-T protein having a sequence identity of 92% or higher with respect to the amino acid sequence represented by SEQ ID NO: 11; or both the mutation in the eIF(iso)4E-S gene and the mutation in the eIF(iso)4E-T gene.

An aspect of the method in accordance with the present invention can be arranged such that: the mutation in the translation initiation factor eIF4E2 gene is a mutation in an eIF4E2-S gene, which mutation is a nonsense mutation in (c1) an exon of a wild-type translation initiation factor eIF4E2-S gene which encodes a translation initiation factor eIF4E2-S protein consisting of an amino acid sequence represented by SEQ ID NO: 2 or (c2) an exon of a wild-type translation initiation factor eIF4E2-S gene which encodes a functional translation initiation factor eIF4E2-S protein having a sequence identity of 88% or higher with respect to the amino acid sequence represented by SEQ ID NO: 2;

a mutation in an eIF4E2-T gene, which mutation is a nonsense mutation in (d1) an exon of a wild-type translation initiation factor eIF4E2-T gene which encodes a translation initiation factor eIF4E2-T protein consisting of an amino acid sequence represented by SEQ ID NO: 5 or (d2) an exon of a wild-type translation initiation factor eIF4E2-T gene which encodes a functional translation initiation factor eIF4E2-T protein having a sequence identity of 88% or higher with respect to the amino acid sequence represented by SEQ ID NO: 5; or both the mutation in the eIF4E2-S gene and the mutation in the eIF4E2-T gene.

An aspect of the method in accordance with the present invention can be arranged such that the nonsense mutation is one or more of the following mutations (1) through (4): (1) a mutation in which C of codon CAA is substituted by T; (2) a mutation in which C of codon CGA is substituted by T; (3) a mutation in which C of codon CAG is substituted by T; and (4) a mutation in which G (either one or both of two Gs) of codon TGG is substituted by A.

Another aspect of a method in accordance with the present invention for producing a virus-resistant tobacco includes the step of: producing tobacco resistant to a virus by (i) introducing a factor that causes a translation initiation factor eIF(iso)4E gene to be expressed at a lower level than a wild type, and (ii) introducing a factor that causes a translation initiation factor eIF4E2 gene to be expressed at a lower level than a wild type, the translation initiation factor eIF(iso)4E being at least one of eIF(iso)4E-S and eIF(iso)4E-T, and the translation initiation factor eIF4E2 being at least one of eIF4E2-S and eIF4E2-T.

An aspect of the method in accordance with the present invention can be arranged such that the virus is a virus belonging to the genus *Potyvirus*.

An aspect of the method in accordance with the present invention can be arranged such that the virus belonging to the genus *Potyvirus* is at least one of (i) a strain of Potato virus Y which strain breaks virus resistance of Virgin A mutant of tobacco and (ii) the Potato virus Y.

An aspect of a method in accordance with the present invention for producing a bred progeny of a virus-resistant tobacco includes self-pollinating or cross-pollinating (i) a virus-resistant tobacco produced by a method recited above or (ii) a progeny of the virus-resistant tobacco thus produced.

An aspect of a combination of detection polynucleotides in accordance with the present invention includes: a first detection polynucleotide which is a polynucleotide for detecting a mutation in a translation initiation factor eIF4E2 gene of tobacco, the mutation (i) causing production of an eIF4E2 protein which is non-functional with respect to a virus or (ii) suppressing expression of the eIF4E2 gene; and a second detection polynucleotide which is a polynucleotide for detecting a mutation in a translation initiation factor eIF(iso)4E gene of tobacco, the mutation (a) causing production of an eIF(iso)4E protein which is non-functional with respect to a virus or (b) suppressing expression of the eIF(iso)4E gene.

An aspect of a method in accordance with the present invention for selecting a virus-resistant tobacco includes: an examination step of examining tobacco for presence or absence of a mutation in genomic DNA by using a combination recited above; and a selection step of selecting, as the virus-resistant tobacco, tobacco in which the mutation has been detected in the examination step.

An aspect of a combination of DNA markers in accordance with the present invention for determining whether tobacco is resistant to a virus includes: a first determination DNA marker which contains a polynucleotide consisting of a continuous base sequence which contains a mutation in a translation initiation factor eIF4E2 gene or of a sequence complementary to the continuous base sequence, the mutation (i) causing production of an eIF4E2 protein which is non-functional with respect to a virus or (ii) suppressing expression of the eIF4E2 gene; and a second determination DNA marker which contains a polynucleotide consisting of a continuous base sequence which contains a mutation in a translation initiation factor eIF(iso)4E gene or of a sequence complementary to the continuous base sequence, the mutation (a) causing production of an eIF(iso)4E protein which is non-functional with respect to a virus or (b) suppressing expression of the eIF(iso)4E gene.

An aspect of leaf tobacco in accordance with the present invention is leaf tobacco of a virus-resistant tobacco recited above.

An aspect of a tobacco product in accordance with the present invention contains, as a material, leaf tobacco recited above.

The following description will more specifically discuss the embodiment of the present invention with reference to Examples. It is a matter of course that the present invention is not limited to the Examples below and that details of the present invention can have various aspects. Further, the present invention is not limited to the embodiments, but can be altered by a skilled person in the art within the scope of the claims. An embodiment derived from a proper combination of technical means disclosed in respective different embodiments is also encompassed in the technical scope of the present invention. Moreover, all the literatures described herein are thereby incorporated by reference.

EXAMPLE 1

(Gene sequence acquisition)
[eIF4E2 gene]

GenBank database (www.ncbi.nlm.nih.gov/pubmed) was searched to acquire, as translation initiation factors of tobacco (*N. tabacum*), the mRNA base sequence of eIF4E assigned GenBank accession number EB451717, the mRNA base sequence of eIF4E assigned GenBank accession number KF155696, and the mRNA base sequence of eIF4E assigned GenBank accession number KM202068. These eIF4Es were named eIF4E2. These eIF4Es had a homology of 70% to 74% with respect to eIF4E1 (accession number: AY702653, Non-Patent Literature 19). By BLAST analysis using the Whole-genome shotgun contigs (WGS) of *N. tomentosiformis* and *N. sylvestris* on the GenBank database, it was determined that eIF4E2 assigned accession number EB451717 and eIF4E2 assigned accession number KF155696 are derived from *N. sylvestris*, and eIF4E2 assigned accession number KM202068 is derived from *N. tomentosiformis*. EB451717 (whose protein coding region sequence is from the 87th base to the 746th base) and KF155696 (whose protein coding region sequence is from the 112th base to the 771st base) have a DNA sequence identity, in the protein coding region, of 99.8% (659 out of 660 bases coincide), and the proteins encoded therein have an amino acid sequence identity of 100%. The single different base in the DNA sequences is presumably due to a difference in the plant varieties from which the respective DNA is derived. These sequences were named eIF4E2-S (GenBank accession numbers: EB451717, KF155696) and eIF4E2-T (GenBank accession number: KM202068). It has been shown that tobacco in which a function of the eIF4E2-S gene is disrupted becomes resistant to PVY (Non-Patent Literature 22).

The base sequence of eIF4E2-S (KF155696) is represented by SEQ ID NO: 1, the amino acid sequence of a protein encoded by eIF4E2-S is represented by SEQ ID NO: 2, and the genomic sequence of an eIF4E2-S gene is represented by SEQ ID NO: 3. The genomic sequence is derived from variety K326 and consists of the 7001st to 13000th bases of accession number AWOJ01222271. The base sequence of eIF4E2-T is represented by SEQ ID NO: 4, the amino acid sequence of a protein encoded by eIF4E2-T is represented by SEQ ID NO: 5, and the genomic sequence of an eIF4E2-T gene is represented by SEQ ID NO: 6. SEQ ID NO: 6 was obtained by carrying out BLAST analysis with respect to the WGS of *N. tabacum* on the GenBank database by using the sequence of KM202068 as a query. Specifically, SEQ ID NO: 6 is a sequence corresponding to the 30001st to 38039th positions of a sequence complementary to accession number AWOJ01182781 (a genomic DNA sequence derived from variety K326). The exon sequence of this genomic sequence had a sequence identity of 99.2% (652 out of 657 bases coincided) with respect to the DNA sequence of a protein coding region of KM202068. KM202068 is derived from the line T021658, and AWOJ01182781 is derived from the variety K326. As such, it was presumed that the above difference of approximately 1% (5 out of the 657 bases differing) was due to the difference between tobacco lines/tobacco varieties. The protein coding regions of the eIF4E2-S gene and the eIF4E2-T gene showed a DNA sequence identity of 93.2% (612 out of 657 bases coincided). Further, proteins encoded by the eIF4E2-S gene and the eIF4E2-T gene showed an amino acid sequence identity of 87.7% (192 out of 219 amino acids coincided), and an amino acid sequence similarity of 97.3% (213 out of 219 amino acids coincided or had similarity). For analyses of sequence identities, etc., nucleic acid and amino acid sequence analysis software GENETYX (registered trademark) (ver.12) (GENETYX CORPORATION) was used.

[eIF(iso)4E Gene]

GeneBank database was searched to acquire the mRNA base sequence of a translation initiation factor eIF(iso)4E of tobacco (*N. tabacum*), which is assigned the accession number AY699609. This sequence is represented by SEQ ID NO: 7. The amino acid sequence of a protein encoded by this gene is represented by SEQ ID NO: 8. By BLAST analysis using the WGS of the GenBank database, it was determined that this eIF(iso)4E is derived from *N. sylvestris*. As such, this gene was named eIF(iso)4E-S. By using this sequence as a query to search WGS contigs of *N. tabacum* on the GenBank database, a genomic sequence (accession number AWOJ01412288), derived from tobacco variety K326, which has a sequence identity of 100% in the protein coding region was obtained. Of this genomic sequence, a sequence of an eIF(iso)4E-S gene region thereof (genomic sequence of the eIF(iso)4E-S gene) is represented by SEQ ID NO: 9.

Furthermore, two sequences assigned GenBank accession number EB683576 (represented by SEQ ID NO: 10) and FN666434 were identified as eIF(iso)4E-T of *N. tabacum* which is encoded by a tobacco genome derived from *N. tomentosiformis*. EB683576 is the sequence of an eIF(iso)4E-T gene derived from tobacco variety K326, and FN666434 is the sequence of an eIF(iso)4E-T gene derived from tobacco variety Samsun NN. The two have a sequence identity of 97%. Proteins encoded by these two genes showed an amino acid sequence identity of 97% and an amino acid sequence similarity of 99%. Such a sequence difference was attributed to the difference between varieties from which the genes are derived. Further, eIF(iso)4E-S (AY699609) and eIF(iso)4E-T (EB683576) showed a DNA sequence identity of 91%. The amino acid sequence (SEQ ID NO: 8) of eIF(iso)4E-S and the amino acid sequence (SEQ ID NO: 11) of eIF(iso)4E-T showed an identity of 91% and a similarity of 96%. By using the mRNA sequence of eIF(iso)4E-T (EB683576) to search WGS contigs of *N. tabacum* on the GenBank database, a genomic sequence (accession number AWOJ01054542), derived from tobacco variety K326, which has a sequence identity of 100% in the protein coding region was obtained. Of this genomic sequence, a sequence of an eIF(iso)4E-T gene region thereof (genomic sequence of the eIF(iso)4E-T gene) is represented by SEQ ID NO: 12.

(Construction of RNAi Constructs)

In order to produce tobacco in which expression of eIF4E2 and eIF(iso)4E are suppressed, RNAi constructs having respective internal sequences of those genes as triggers were constructed.

Primers for specifically amplifying an eIF4E2 trigger sequence (SEQ ID NO: 13; 339 bases derived from EB451717) and an eIF(iso)4E trigger sequence (SEQ ID NO: 14; 313 bases derived from AY699609) were produced (Table 1). A CACC sequence for use in cloning (described later) was added to the 5'end of an FW primer for each gene. Note that, though the trigger for eIF4E2 and the trigger for eIF(iso)4E were both designed based on a sequence of an S-type gene, the sequences of these triggers each have a sequence identity of 90% or higher with respect to the T-type of the respective genes. As such, it was presumed that these triggers are effective in reducing the amount of transcripts of both S-type and T-type genes.

TABLE 1

Primers for Cloning of RNAi Trigger Sequence of Translation Initiation Factor

| Primer name | Sequence (5'-3') | Target gene | SEQ ID NO |
|---|---|---|---|
| Nt-eIF4E2-FW(CACC) | CACCGCGGGTAGATGAAGTAGAAG | Nt-eIF4E2 | SEQ ID NO: 15 |
| Nt-eIF4E2-RV | CCTCCATTCGCACATACAGG | | SEQ ID NO: 16 |
| Nt-eIF(iso)4E-FW(CACC) | CACCAGAGGCGACGGAGGTTCC | Nt-eIF(iso)4E | SEQ ID NO: 17 |
| Nt-eIF(iso)4E-RV | TCTGCTGCTCGTAACAGTCC | | SEQ ID NO: 18 |

By using MagDEA (Registered Trademark) RNA100 (GC) (Precision System Science Co., Ltd.), RNA was extracted from a tobacco seedling and purified. Then, PrimeScript™ RT reagent kit (Takara-Bio Inc.) was used to synthesize cDNA from the purified RNA. With use of the cDNA as a template and the gene-specific primers shown in Table 1, gene fragments of eIF4E2 and eIF(iso)4E were amplified. Specifically, 10 ng of the template DNA and 5 pmoles each of the primers were contained in a 20 μL reaction solution, PrimeSTAR Max DNA Polymerase (Takara-Bio Inc.) was used as an enzyme, and a reaction was carried out under the following conditions: 35 cycles each consisting of (i) 98° C. for 10 seconds, (ii) 55° C. for 15 seconds, and (iii) 72° C. for 15 seconds. PCR products (approximately 320 bp for eIF4E2; approximately 310 bp for eIF(iso)4E) were purified by using MiniElute PCR Purification kit (Qiagen Inc.). Thereafter, the purified PCR products were cloned in a vector pENTR™/D-TOPO (registered trademark) (Life Technologies Corporation). After a base sequence of an insert was checked, GateWay (registered trademark) LR Clonase (registered trademark) II Enzyme mix (Life Technologies Corporation) was used to clone the insert into RNAi vector pSP231 (see the literature: International publication WO2011/102394). The vector pSP231, which is a vector in which a GFP (Green-fluorescent protein gene) expression cassette was inserted into a SacI site of pHellsgate 12 (see the literature: Wesley et al., 2001, Plant J., 27, 581-590), is a binary vector that causes a cauliflower mosaic virus 35SRNA gene promotor to drive an RNAi sequence which is formed such that a pdk/cat intron is located between inverted repeat sequences of a trigger sequence. After the cloning into pSP231, an RNAi trigger sequence and its orientation were checked. As a result, a final RNAi construct was obtained.

The RNAi construct thus prepared was introduced into an *Agrobacterium* LBA4404 strain by an electroporation method.

(Tobacco Transformation)

Tobacco was transformed by a usual method (leaf disc method). The tobacco varieties used were Petit Havana SR1 and TN90. SR1 is a variety susceptible to PVY and PVY-B. TN90 is a variety in which the eIF4E2-S gene has been deleted, and which is resistance to PVY (but susceptible to PVY-B).

A tobacco cotyledon was cut at four corners thereof, and leaf segments thus obtained were immersed in an *Agrobacterium* solution for 10 minutes. The leaf segments were wiped dry and then placed on an LS solid medium (containing 3% sucrose and 0.8% agar). The leaf segments were cultured in the dark at 25° C. for 3 days so that tobacco was infected with recombinant *Agrobacterium* to introduce an RNAi construct of each translation initiation factor into SR1. An RNAi construct of the translation initiation factor eIF(iso)4E was introduced into TN90 leaf segments. The leaf segments were placed for 4 days on an LS solid medium containing 250 mg/L of Cefotaxime, 2-isopentenyl adenine (2iP) (10 mg/L), and IAA (0.3 mg/L), both of which are plant hormones, to eradicate *Agrobacterium* therefrom. A recombinant was selected on an LS medium containing Cefotaxime and the plant hormones in the above concentrations and further containing 50 mg/L kanamycin. A shoot, which had been redifferentiated from the selected recombinant, was placed on a rooting medium (LS solid medium containing 1.5% sucrose, 0.3% gellan gum and further containing Cefotaxime and kanamycin in the above concentrations) so that the shoot was rooted. The resulting recombinant tobacco was cultivated in a greenhouse.

(Transcriptional Analysis of the Translation Initiation Factor in the Recombinant Tobacco of the Original Generation of Transformation)

In order to examine expression of the eIF4E2 or eIF(iso)4E gene in the recombinant tobacco, a set of primers and a probe for real-time PCR were designed based on the base sequence of each gene (Table 2). Further, total RNA was extracted from a leaf of each recombinant tobacco by using RNeasy Plant Mini Kit (QIAGEN Inc.). cDNA was synthesized from the obtained RNA by using Prime Script reagent Kit (Takara-Bio Inc.), and the cDNA was used as a template for real-time PCR. In the real-time PCR, TaqMan Fast Advanced Master mix (Life Technologies Corporation) was used to carry out an amplification reaction. The reaction was carried out under the following conditions: 50° C. for 2 minutes and 95° C. for 20 seconds, followed by 40 cycles each consisting of (i) 95° C. for 1 second and (ii) 60° C. for 20 seconds. Expression analysis was carried out with use of StepOne Software v2.2 (Life Technologies Corporation). As an internal standard for PCR, an elongation factor1-alpha (EF1-α) gene was used. For comparison to an expression level of the EF1-α gene, a relative gene expression level of a target gene was calculated. As a control, a non-recombinant tobacco (SR1 and TN90) was used.

TABLE 2

Primers/Probes for Quantitative PCR

| Target gene | Primer/Probe | Sequence (5'-3') | SEQ ID NO |
|---|---|---|---|
| eIF4E2-S | Forward | GCCACTGAAGCACCGATAGAG | SEQ ID NO: 19 |
| | Reverse | TTATCGAACCAGAATGTCCATCTC | SEQ ID NO: 20 |
| | Probe | TTTCTGGATTACAGCAACTCGATTGGCC | SEQ ID NO: 21 |
| eIF(iso)4E-S | Forward | GCCACTGAAGCACCGATAGAG | SEQ ID NO: 22 |
| | Reverse | TTATCGAACCAGAATGTCCATCTC | SEQ ID NO: 23 |
| | Probe | TCGCCGGCGTCAGCGAC | SEQ ID NO: 24 |
| eIF(iso)4E-T | Forward | GCCGGATACGGTGGAGAAG | SEQ ID NO: 25 |
| | Reverse | CCAAACAGCGCCTTGCTT | SEQ ID NO: 26 |
| | Probe | ATGGACATTCTGGTFCGAT | SEQ ID NO: 27 |
| EF-a | Forward | CTAAGGGTGCTGCCAGCTTT | SEQ ID NO: 28 |
| | Reverse | GTCAAGCACTGGAGCATATCCA | SEQ ID NO: 29 |
| | Probe | ATCATGAACCATCCAGGACAGATTGG | SEQ ID NO: 30 |

Measurements were made to determine the amount of transcripts of the eIF4E2 gene in the recombinant tobacco in which the RNAi construct of eIF4E2 had been introduced into tobacco variety SR1, and the amount of transcripts of the eIF(iso)4E gene in the recombinant tobacco into which the RNAi construct of the eIF(iso)4E had been introduced. With regards to eIF4E2, three lines were obtained which had an expression level being not more than 10% of that in the control variety SR1. These lines were 4E2 #3, 4E2 #4, and 4E2 #5. With regards to eIF(iso)4E, three lines were obtained which had an expression level being not more than 5% of that in the control variety SR1. These lines were iso4E #1, iso4E #7, and iso4E #15. Measurements were also made to determine the amount of transcripts of the eIF(iso)4E gene in the TN90 into which an RNAi construct of eIF(iso)4E had been introduced. The results of these measurements are shown in FIG. 1. As a line in which transcription was suppressed with a high degree in the original-generation transformant, #8 (whose expression level was 6% of that of the control variety TN90) was selected. As a control line in which transcription was not suppressed, #27 (whose expression level was equivalent to that of TN90) was selected.

(Isolation of the Recombinant Tobacco of the Next Generation of Transformation)

The following selfed seeds were aseptically sown on an LS solid medium (containing 3% sucrose and 0.8% sugar): selfed seeds of transformed SR1 tobacco in which transcription was suppressed with a high degree in the original-generation transformant, i.e., three lines in which eIF4E2 expression was suppressed and three lines in which eIF(iso)4E expression was suppressed; selfed seeds of the transformed TN90 #8, in which eIF(iso)4E transcription was suppressed with a high degree in the original-generation transformant; and selfed seeds of #27, in which transcription was not suppressed. GFP fluorescences of seedling plants which had germinated and grown were measured by using Fluor Imager 595 (Molecular Dynamics, Inc.). As described earlier, pSP231 used for construct introduction includes a 35S promoter-GFP expression cassette provided next to the RNAi expression cassette on the T-DNA region. It was determined (i) that the seedling plants that had emitted strong GFP fluorescence were lines which were homozygous for the RNAi construct, (ii) that the seedling plants that had emitted no fluorescence were null segregant lines for the RNAi construct (in which none of the RNAi constructs were present), and (iii) that the seedling plants that had emitted weak fluorescence were lines which were hemizygous for the RNAi construct. A homozygous line of the eIF(iso)4E expression-suppressed line TN90 #8 was thus obtained. Note that it was determined that TN90 #27 was a null line because no fluorescence was detected. Three weeks after the sowing, the plants were transferred to a greenhouse and then planted and cultivated in a culture soil.

(Transcriptional Analysis of the Translation Initiation Factor in the Recombinant Tobacco of the Next Generation of Transformation)

In order to examine expression of the eIF4E2 gene and eIF(iso)4E gene of the next generation of each line of the recombinant tobacco, cDNA was synthesized, as described earlier, from RNA which had been extracted from a leaf of the recombinant tobacco, and the cDNA was used as a template for real-time PCR. The real-time PCR was also carried out as described earlier. As an internal standard for PCR, an EF1-α gene was used. As a control plant, non-recombinant tobacco was used. For both eIF4E2 and eIF(iso)4E, primers and probes for S-type genes were used.

Figure 2:
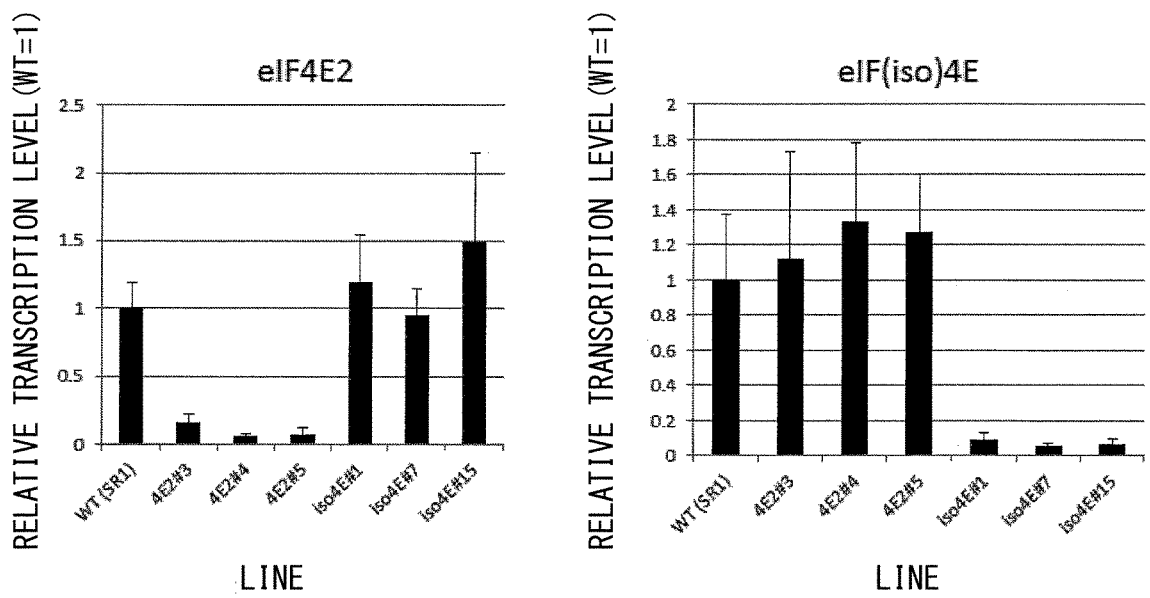
FIG. 2 shows results of quantitative PCR analysis of an eIF4E2 gene and an eIF(iso)4E gene expression in recombinant tobacco obtained by introducing an RNAi construct of the eIF4E2 gene or the eIF(iso)4E gene into tobacco variety SR1.

The results of real-time PCR analysis of eIF4E2 and eIF(iso)4E gene expression are shown in FIG. 2. In the case of SR1, it was found that in the eIF4E2 expression-suppressed lines #3, #4, and #5, expression was suppressed to approximately 15%, 5%, and 7%, respectively, of that of the non-recombinant line (SR1). It was also found that in the eIF(iso)4E expression-suppressed lines #1, #7, and #15, expression was suppressed to approximately 9%, 5%, and 6%, respectively, of that of the non-recombinant line (SR1).

The RNAi recombinant tobacco (SR1) which contained the RNAi constructs for the eIF4E2 gene homozygously and the RNAi recombinant tobacco (SR1) which contained the RNAi constructs for eIF(iso)4E gene homozygously were crossed so that a recombinant tobacco (SR1) having both an RNAi construct of the eIF4E2 gene and an RNAi construct of the eIF(iso)4E gene was produced.

(Virus Inoculation Tests on Recombinant Tobacco Plants in which Transcription of a Plurality of Translation Initiation Factors was Suppressed)

In virus inoculation tests, tobacco TN90 #8 homozygous line, which had an RNAi construct of the eIF(iso)4E gene, was used. Note that, as described above, TN90 is a variety in which the eIF4E2-S gene has been originally deleted. Furthermore, as controls, cultivar TN90, Tsukuba 1, and a mutant in which the functions of both S-type and T-type eIF(iso)4E genes were disrupted (this mutant hereinafter referred to as an "eIF(iso)4E mutant"). The eIF(iso)4E mutant was obtained by carrying out EMS treatment with respect to tobacco seeds. In the eIF(iso)4E mutant, the 330th position of the eIF(iso)4E-S gene represented by SEQ ID NO: 9 is mutated from C to T, and the 299th position of the eIF(iso)4E-T gene represented by SEQ ID NO: 12 is mutated from G to A. Each of these mutations is a nonsense mutation (the mutant is described in detail in Patent Literature 5).

Ten days after transplantation into a culture soil, plants were inoculated with PVY (PVY-N), PVY-B, or TBTV. PVY-B, which is a virus strain that was isolated at the Leaf Tobacco Research Center of Japan Tobacco Inc., is a VAM breaking strain that causes a necrosis symptom in the tobacco variety Virgin A mutant (VAM), which is PVY resistant. TBTV, which is a virus belonging to the genus *Umbravirus*, causes a mottling symptom on a leaf of tobacco. As an inoculum, a leaf of flue-cured variety Tsukuba 1 (in the case of PVY and TBTV), or a leaf of VAM (in the case of PVY-B), the leaf having been infected with each virus and having developed a disease symptom, was used. The variety Tsukuba 1 is susceptible to PVY, PVY-B, and TBTV, and shows clear disease symptoms in response to inoculation thereinto of PVY, PVY-B, and TBTV. The infected leaf was collected and then ground in 0.01N phosphate buffer solution in a mortar. Virus was inoculated, by rubbing a viral solution obtained by the grinding with use of carborundum, into a half of the largest leaf of a tobacco seedling one week after the transplantation (fourth or fifth leaf from the bottom). Thereafter, the individuals were cultivated in a greenhouse, and their disease symptoms were observed.

The results of PVY inoculation, PVY-B inoculation, and TBTV inoculation are shown in Tables 3, 4, and 5, respectively. Note that in each of the tables, with regards to the letters S and T (which represent an S-type gene and a T-type gene, respectively), a capital letter indicates no mutation, whereas a lowercase letter represents the presence of mutation (or suppressed expression).

As is shown in Table 3, in the PVY inoculation test, disease symptoms were observed in all individuals of the Tsukuba 1, serving as a control, 8 days after inoculation, and in all individuals of the eIF(iso)4E mutant, serving as a control, 15 days after inoculation. With regards to the conventional PVY-resistant variety TN90, disease symptoms were observed in more than ¼ of all individuals thereof 15 days after inoculation, and in more than half of all individuals thereof 30 days after inoculation. In contrast, with regards to tobacco TN90 #8, in which the functions of eIF4E2-S and eIF(iso)4E were suppressed, no disease symptoms were observed 15 days after inoculation, and even 30 days after inoculation, disease symptoms were observed in only one individual out of 15. This proved that the tobacco TN90 #8, in which the functions of eIF4E2-S and eIF(iso)4E were suppressed, expresses stronger resistance than a conventional PVY-resistant variety.

As is shown in Table 4, in the PVY-B inoculation test, disease symptoms were observed in almost all individuals of the TN90, serving as a control, 8 days after inoculation, and in almost all individuals of the Tsukuba 1, serving as a control, 15 days after inoculation. With regards to the eIF(iso)4E mutant which is a conventional PVY-B-resistant tobacco variety, disease symptoms were observed in 2 out of 14 individuals thereof 15 days after inoculation, and in approximately 80% of all individuals thereof 30 days after inoculation. In contrast, with regards to tobacco TN90 #8, in which the functions of eIF4E2-S and eIF(iso)4E were suppressed, disease symptoms were observed in 1 out of 15 individuals 8 days after inoculation, and in 2 individuals 15 days after inoculation. However, 30 days after inoculation, the number of individuals having disease symptoms remained at 2 (13.3%). This proved that the tobacco TN90 #8, in which the functions of eIF4E2-S and eIF(iso)4E were suppressed, expresses stronger resistance than a conventional PVY-B-resistant line.

As is shown in Table 5, in the TBTV inoculation test, the tobacco TN90 #8, in which the functions of eIF4E2-S and eIF(iso)4E were suppressed, exhibited an incidence of disease symptoms which incidence was clearly lower than that of the TN90 and the Tsukuba 1, each serving as a control.

TABLE 3

PVY Inoculation Test Results

| | | Number of individuals showing disease symptom/number of individuals under test (Disease incidence rate) | | |
|---|---|---|---|---|
| Line | Genotype | 8 days after inoculation | 15 days after inoculation | 30 days after inoculation |
| Recombinant TN90-RNAi #8 | eIF4E2-ssTT eIF(iso)4E-sstt(RNAi) | 0/15 (0.0%) | 0/15 (0.0%) | 1/15 (6.7%) |
| Cultivar TN90 | eIF4E2-ssTT eIFiso4E-SSTT | 0/15 (0.0%) | 4/15 (26.7%) | 8/15 (53.3%) |
| eIF(iso)4E mutant | eIF4E2-SSTT eIF(iso)4E-sstt | 13/15 (86.7%) | 15/15 (100.0%) | 15/15 (100.0%) |
| Cultivar Tsukuba 1 | eIF4E2-SSTT eIF(iso)4E-SSTT | 15/15 (100.0%) | 15/15 (100.0%) | 15/15 (100.0%) |

TABLE 4

PVY-B Inoculation Test Results

| | | Number of individuals showing disease symptom/number of individuals under test (Disease incidence rate) | | |
|---|---|---|---|---|
| Line | Genotype | 8 days after inoculation | 15 days after inoculation | 30 days after inoculation |
| Recombinant TN90-RNAi #8 | eIF4E2-ssTT eIF(iso)4E-sstt(RNAi) | 1/15 (6.7%) | 2/15 (13.3%) | 2/15 (13.3%) |
| Cultivar TN90 | eIF4E2-ssTT eIFiso4E-SSTT | 15/15 (100.0%) | 15/15 (100.0%) | 15/15 (100.0%) |
| eIF(iso)4E mutant | eIF4E2-SSTT eIF(iso)4E-sstt | 0/14 (0.0%) | 2/14 (14.3%) | 11/14 (78.6%) |
| Cultivar Tsukuba 1 | eIF4E2-SSTT eIF(iso)4E-SSTT | 14/15 (93.3%) | 15/15 (100.0%) | 15/15 (100.0%) |

TABLE 5

TBTV Inoculation Test Results

| Line | Genotype | Number of individuals showing disease symptom/number of individuals under test (Disease incidence rate) | | |
|---|---|---|---|---|
| | | 8 days after inoculation | 15 days after inoculation | 30 days after inoculation |
| Recombinant TN90-RNAi #8 | eIF4E2-ssTT eIF(iso)4E-sstt(RNAi) | 1/13 (7.7%) | 5/13 (38.5%) | 9/13 (69.2%) |
| Cultivar TN90 | eIF4E2-ssTT eIFiso4E-SSTT | 8/14 (57.1%) | 10/14 (71.4%) | 11/14 (78.6%) |
| eIF(iso)4E mutant | eIF4E2-SSTT eIF(iso)4E-sstt | 0/15 (0.0%) | 1/15 (6.7%) | 3/15 (20.0%) |
| Cultivar Tsukuba 1 | eIF4E2-SSTT eIF(iso)4E-SSTT | 4/10 (40.0%) | 6/10 (60.0%) | 8/10 (80.0%) |

Thus, it was proven that suppression of the transcription of not only the eIF4E2-S gene but also both the eIF(iso)4E-S gene and the eIF(iso)4E-T gene provides resistance against all three viruses, which are PVY, PVY-B, and TBTV. Furthermore, it was surprisingly proven that such suppression provides resistance against PVY and PVY-B which resistance is stronger than that in conventional resistant strains.

Example 2

(Selection of Tobacco Mutant Having Mutation in eIF4E2-S Gene, eIF(Iso)4E-S Gene, and eIF(Iso)4E-T Gene)

The variety TN90 was used as tobacco in which the function of the eIF4E2-S gene was suppressed. Furthermore, the eIF(iso)4E mutant of Example 1 was used as tobacco in which the functions of both the eIF(iso)4E-S gene and the eIF(iso)4E-T gene were suppressed. The eIF(iso)4E mutant has homozygous mutations (nonsense mutations) in both the eIF(iso)4E-S gene and the eIF(iso)4E-T gene such that transcription of the eIF(iso)4E-S gene and transcription of the eIF(iso)4E-T gene are suppressed (Patent Literature 5). Note that the genotype of the eIF4E2 gene and the eIF(iso)4E gene in each individual is represented in the following manner: eIF4E2-SSTT/eIF(iso)4E-SSTT. For example, the genotype of TN90 is eIF4E2-ssTT/eIF(iso)4E-SSTT, and the genotype of the eIF(iso)4E mutant is eIF4E2-SSTT/eIF(iso)4E-sstt.

An eIF4E2-ssTT/eIF(iso)4E-sstt line and an eIF4E2-ssTT/eIF(iso)4E-SSTT line, serving as a control, were developed as follows. First, TN90 and an eIF(iso)4E mutant were crossed to obtain F1. F1 individuals were then crossed with TN90 to obtain BC1F1. After BC1F1 seeds were sown, DNA was extracted from each individual thereof, and individuals whose genotype was eIF4E2-ssTT/eIF(iso)4E-SsTt were selected by use of (i) a dominant SCAR marker (Table 6) for determining whether or not the eIF4E2-S gene was deleted and (ii) a dCAPS marker (described in detail in Patent Literature 5; sequence listed in Table 7 below) for identifying polymorphism in the eIF(iso)4E-S gene and the eIF(iso)4E-T gene. Thereafter, selfed seeds (BC1F2) of the selected individuals were sown, and dCAPS marker analysis was carried out in a manner similar to that for BC1F1 so that individuals whose genotype was eIF4E2-ssTT/eIF(iso)4E-sstt and individuals whose genotype was eIF4E2-ssTT/eIF(iso)4E-SSTT were selected. The selected individuals were selfed, and seeds of the lines having these genotypes were propagated.

TABLE 6

| Primer name | Sequence (5'-3') | Target gene | SEQ ID NO |
|---|---|---|---|
| Nt-eIF4E2-S-F | GAATTGGACAATGAGCTTTAGT | Nt-eIF4E2-S | SEQ ID NO: 31 |
| Nt-eIF4E2-S-R | TAGATGTGTGGCTGTAAATTG | Nt-eIF4E2-S | SEQ ID NO: 32 |

TABLE 7

| Target site | Primer | Sequence (5+-3+) | SEQ ID NO |
|---|---|---|---|
| eIF(iso)4E_S_1st PCR | Forward(F) | GGCCTAAACGTTGTAAGACAA | SEQ ID NO: 33 |
| | Reverse(R) | TGCTTAGTTAAATGCTACAGGG | SEQ ID NO: 34 |
| eIF(iso)4E_S_2nd PCR | Forward(F) | AAATCGACACAAAGGGAGGAG | SEQ ID NO: 35 |
| | Reverse(R) | AACTTCCCCAAGCGGCTCCaT* | SEQ ID NO: 36 |
| eIF(iso)4E_T_1st PCR | Forward(F) | GACCTGAACATTGCAAGATGA | SEQ ID NO: 37 |
| | Reverse(R) | GGCTTACTTGAATGCTACAAGG | SEQ ID NO: 38 |
| eIF(iso)4E_T_2nd PCR | Forward(F) | GCCTCAATCGACACAAAAGGGAGAG | SEQ ID NO: 39 |
| | Reverse(R) | AGCGCCTTGCTTCGGCTTATCGAt* | SEQ ID NO: 40 |

*Lowercase letters are used to indicate a base which is a mismatch with the target template DNA and which was inserted to create a restriction enzyme site in a wild type gene.

DNA extraction during selection of individuals was carried out as follows. A tobacco leaf sample (1 cm×1 cm) was put in a 2 mL tube, and 400 µL of extraction solution (composition: 200 mM Tris-HCl (pH7.5), 250 mM NaCl, 25 mM EDTA, 0.5% SDS) and 200 µL of Protein Precipitation Solution (manufactured by QIAGEN Inc.) were added to the tube. Thereafter, the tobacco leaf sample was crushed in the presence of metal cones. Subsequently, the tube was centrifuged at 13000 rpm for 10 minutes. To another 1.5 mL tube, 300 µL of supernatant was transferred. Then, to the supernatant, 800 µL of 100% ethanol was added. A resultant mixture solution was mixed by inversion. After centrifugation at 15000 rpm for 10 minutes, the supernatant was completely removed. After a pellet was confirmed to be dry, 50 µL of TE (10 mM Tris-HCl (pH 7.5), 1 mM EDTA) was added.

Polymorphism of the eIF4E2-S gene was identified by carrying out PCR with use of primers (Table 6) designed for a region in the gene, and then determining the presence/absence of amplification by electrophoresis. PCR was carried out in a 10 µL reaction system with use of 5 ng of tobacco genomic DNA. A QIAGEN Multiplex PCR Kit (QIAGEN Inc.) was used for enzymes necessary for the PCR reaction and reagents necessary for the PCR reaction. The reaction was carried out under the following conditions: 95° C. for 15 minutes, followed by 38 cycles each consisting of (i) 94° C. for 30 seconds, (ii) 58° C. for 30 seconds, and (iii) 72° C. for 45 seconds, followed by 72° C. for 90 seconds after the 38 cycles were carried out. As a result of the electrophoresis, in a sample having a normal eIF4E2-S gene, a band equivalent to a 475 bp fragment was found, whereas no band was found in samples in which the eIF4E2-S gene was deleted (such as in TN90). It was therefore confirmed that the presence/absence of the band made it possible to determine deletion of the eIF4E2-S gene.

A dCAPS marker was used to identify polymorphism of the eIF(iso)4E-S gene and the eIF(iso)4E-T gene. $1^{st}$ PCR was carried out with use of Tks Gflex™ DNA Polymerase. As a template, approximately 5 ng of genomic DNA was used. The primers were adjusted so as to have a concentration of 1 μM. As a buffer, a buffer accompanying the enzyme was used. PCR was carried out under the following conditions: 94° C. for 1 minute, followed by 30 cycles each consisting of (i) 98° C. for 10 seconds, (ii) 60° C. for 15 seconds, and (iii) 68° C. for 30 seconds, followed by 68° C. for 90 seconds after the 30 cycles were carried out. Thereafter, products obtained by $1^{st}$ PCR were diluted by a 100-fold dilution factor. By using 1 μL of dilute as a template, $2^{nd}$ PCR was carried out with use of TaKaRa Taq™. As in $1^{st}$ PCR, the primers were adjusted so as to have a concentration of 1 μM, and the buffer accompanying the enzyme was used. PCR was carried out under the following conditions: 94° C. for 2 minutes, followed by 40 cycles each consisting of (i) 94° C. for 30 seconds, (ii) 52° C. for 30 seconds, and (iii) 72° C. for 30 seconds, followed by 72° C. for 90 seconds after the 40 cycles were carried out. Products obtained by $2^{nd}$ PCR of the eIF(iso)4E-S gene were treated with Nla III (New England Biolabs Inc.). Products obtained by $2^{nd}$ PCR of the eIF(iso)4E-T gene were treated with Mbo I (Takara-Bio, Inc.). As for a sample in which products amplified by the eIF(iso)4E_S primers were not cleaved while being treated with the restriction enzyme, it was determined that the genotype of the sample was "ss". Meanwhile, as for a sample in which products amplified by the eIF(iso)4E_T primers were not cleaved while being treated with the restriction enzyme, it was determined that the genotype of the sample was "tt". For example, as for a sample in which no cleavage occurred in products amplified by the eIF(iso)4E_S primers, and cleavage occurred in products amplified by the eIF(iso)4E_T primers, it was determined that the genotype of the sample was "ssTT". As for a sample in which cleavage occurred in products amplified by the eIF(iso)4E_S primers, and no cleavage occurred in products amplified by the eIF(iso)4E_T primers, it was determined that the genotype of the sample was "SStt". As for a sample in which cleavage occurred in both products amplified by the eIF(iso)4E_S primers and products amplified by the eIF(iso)4E_T primers, it was determined that the genotype of the sample was "SSTT". As for a sample in which no cleavage occurred in both products amplified by the eIF(iso)4E_S primers and products amplified by the eIF(iso)4E_T primers, it was determined that the genotype of the sample was "sstt". As for a sample in which cleavage occurred in some of products amplified by the eIF(iso)4E_S primers and no cleavage occurred in the others, and cleavage occurred in some of products amplified by the eIF(iso)4E_T primers and no cleavage occurred in the others, it was determined that the genotype of the sample was "SsTt". The genotype was thus easily determined.

Subsequently, the following description discusses a method of developing and selecting eIF4E2-ssTT/eIF(iso) 4E-SStt and eIF4E2-ssTT/eIF(iso)4E-ssTT. Individuals whose genotype was eIF4E2-ssTT/eIF(iso)4E-SsTt were selected from the above-described BC1F1 generation. These individuals were crossed with TN90 so that a BC2F1 was obtained. Seeds of the BC2F1 generation were sown, and dCAPS marker analysis was carried out in a manner similar to that for BC1F1 so that individuals whose genotype was eIF4E2-ssTT/eIF(iso)4E-SsTt were selected. The selected BC2F1 individuals were selfed so that a BC2F2 was obtained. From this BC2F2 line, individuals whose genotype was eIF4E2-ssTT/eIF(iso)4E-SStt and individuals whose genotype was eIF4E2-ssTT/eIF(iso)4E-ssTT were selected.

(Virus Inoculation Tests on eIF4E2/eIF(Iso)4E Tobacco Double Mutants)

Two weeks after transplantation in a culture soil, individuals were inoculated with PVY or PVY-B. As in the case of Example 1, a viral inoculum was prepared and a virus was inoculated into tobacco. After the inoculation, the individuals were grown in a greenhouse, and their disease symptoms were observed as appropriate. Tables 8 and 9 show the results of virus inoculation tests carried out on double mutant tobacco deficient with respect to the function of eIF4E2 and the function of eIF(iso)4E.

As is shown in Table 8, in the PVY inoculation test, with regards to (i) Tsukuba 1 serving as a control, (ii) the mutant (eIF(iso)4E-S & T mutant) having mutations in both the S and T of eIF(iso)4E, and (iii) the mutant (eIF(iso)4E-T mutant) having a mutation in the T of eIF(iso)4E, necrosis symptoms were observed in all individuals thereof 10 days after inoculation. With regards to the conventional PVY-resistant variety TN90, disease symptoms were observed in more than half of individuals 19 days after inoculation. With regards to the eIF4E2-S mutant (serving as a control with respect to the double mutants), disease symptoms were observed in 40% of individuals 28 days after inoculation. In contrast, with regards to the double mutants in which the functions of eIF4E2-S and at least eIF(iso)4E-T were suppressed (i.e., the eIF4E2-S/eIF(iso)4E-S & T double mutant and the eIF4E2-S/eIF(iso)4E-T double mutant), no disease symptoms were observed even 28 days after inoculation. These results showed that a double mutant having a mutation(s) in the eIF4E2-S gene and a mutation(s) in at least the eIF(iso)4E-T gene expresses resistance which is stronger than that of a conventional PVY-resistant variety.

As is shown in Table 9, in the PVY-B inoculation test, with regards to (i) TN90 serving as a control, (ii) Tsukuba 1, and (iii) the mutant having a mutation in S of eIF4E2 (i.e., the eIF4E2-S mutant serving as a control with respect to the double mutants), disease symptoms were observed in all individuals 7 days after inoculation. With regards to the mutant (eIF(iso)4E-S & T mutant) which is a PVY-B-resistant tobacco having mutations in both the S and T of eIF(iso)4E, disease symptoms were observed in 3 out of 15 individuals 19 days after inoculation, and in 5 out of 15 individuals 28 days after inoculation. With regards to the mutant (eIF(iso)4E-T mutant) having a mutation in T of eIF(iso)4E, disease symptoms were observed in only 2 out of 10 individuals 7 days after inoculation, but disease symptoms were observed in 5 out of 10 individuals 10 days after inoculation, and in all individuals 19 days after inoculation. In contrast, with regards to the double mutants in which the functions of eIF4E2-S and at least eIF(iso)4E-T were suppressed (i.e., the eIF4E2-S/eIF(iso)4E-S & T double mutant and the eIF4E2-S/eIF(iso)4E-T double mutant), no disease symptoms were observed even 28 days after inoculation. Similarly, with regards to the recombinant plants in which transcription of both the eIF4E2 gene and eIF(iso)4E gene was suppressed by RNAi, no disease symptoms were observed even 28 days after inoculation. These results show that suppression of the functions of the two differing genes, which are the eIF4E2 gene and the eIF(iso)4E gene, results in expression of resistance which is stronger than that of a conventional PVY-B-resistant variety.

In view of the above, it was proven that, by suppressing transcription of not only the eIF4E2-S gene but also the eIF(iso)4E-T gene, or by suppressing transcription of not only the eIF4E2-S gene but also the eIF(iso)4E-S gene and the eIF(iso)4E-T gene, the level of resistance against PVY and PVY-B is made higher as compared with that of a conventional resistant line.

TABLE 8

PVY Inoculation Test Results

| | | Number of individuals showing disease symptom/ number of individuals under test (Disease incidence rate) | | | |
|---|---|---|---|---|---|
| Line | Genotype | 7 days after inoculation | 10 days after inoculation | 19 days after inoculation | 28 days after inoculation |
| eIF4E2-S eIF(iso)4E-S&T double mutant | eIF4E2-ssTT eIF(iso)4E-sstt | 0/15 (0.0%) | 0/15 (0.0%) | 0/15 (0.0%) | 0/15 (0.0%) |
| eIF4E2-S eIF(iso)4E-T double mutant | eIF4E2-ssTT eIF(iso)4E-SStt | 0/12 (0.0%) | 0/12 (0.0%) | 0/12 (0.0%) | 0/12 (0.0%) |
| eIF4E2-S mutant | eIF4E2-ssTT eIF(iso)4E-SSTT | 0/15 (0.0%) | 0/15 (0.0%) | 3/15 (20.0%) | 6/15 (40.0%) |
| Cultivar TN90 | eIF4E2-ssTT eIFiso4E-SSTT | 0/15 (0.0%) | 0/15 (0.0%) | 10/15 (66.7%) | 10/15 (66.7%) |
| eIF(iso)4E-S&T mutant | eIF4E2-SSTT eIF(iso)4E-sstt | 13/15 (86.7%) | 15/15 (100.0%) | 15/15 (100.0%) | 15/15 (100.0%) |
| eIF(iso)4E-T mutant | eIF4E2-SSTT eIF(iso)4E-SStt | 10/10 (100.0%) | 10/10 (100.0%) | 10/10 (100.0%) | 10/10 (100.0%) |
| Cultivar Tsukuba 1 | eIF4E2-SSTT eIF(iso)4E-SSTT | 10/10 (100.0%) | 10/10 (100.0%) | 10/10 (100.0%) | 10/10 (100.0%) |

TABLE 9

PVY-B Inoculation Test Results

| | | Number of individuals showing disease symptom/ number of individuals under test (Disease incidence rate) | | | |
|---|---|---|---|---|---|
| Line | Genotype | 7 days after inoculation | 10 days after inoculation | 19 days after inoculation | 28 days after inoculation |
| eIF4E2-S eIF(iso)4E-S&T double mutant | eIF4E2-ssTT eIF(iso)4E-sstt | 0/15 (0.0%) | 0/15 (0.0%) | 0/15 (0.0%) | 0/15 (0.0%) |
| eIF4E2-S eIF(iso)4E-T double mutant | eIF4E2-ssTT eIF(iso)4E-SStt | 0/11 (0.0%) | 0/11 (0.0%) | 0/11 (0.0%) | 0/11 (0.0%) |
| eIF4E2-S mutant | eIF4E2-ssTT eIF(iso)4E-SSTT | 15/15 (100.0%) | 15/15 (100.0%) | 15/15 (100.0%) | 15/15 (100.0%) |
| Cultivar TN90 | eIF4E2-ssTT eIFiso4E-SSTT | 15/15 (100.0%) | 15/15 (100.0%) | 15/15 (100.0%) | 15/15 (100.0%) |
| eIF(iso)4E-S&T mutant | eIF4E2-SSTT eIF(iso)4E-sstt | 0/15 (0.0%) | 0/15 (0.0%) | 3/15 (20.0%) | 5/15 (33.3%) |
| eIF(iso)4E-T mutant | eIF4E2-SSTT eIF(iso)4E-SStt | 2/10 (20.0%) | 5/10 (50.0%) | 10/10 (100.0%) | 10/10 (100.0%) |
| Cultivar Tsukuba 1 | eIF4E2-SSTT eIF(iso)4E-SSTT | 10/10 (100.0%) | 10/10 (100.0%) | 10/10 (100.0%) | 10/10 (100.0%) |
| eIF4E2 & eIF(iso)4E-RNAi | eIF4E2-sstt (RNAi) eIF(iso)4E-sstt (RNAi) | 0/15 (0.0%) | 0/15 (0.0%) | 0/15 (0.0%) | 0/15 (0.0%) |

INDUSTRIAL APPLICABILITY

The present invention is applicable to breeding of tobacco.

The invention claimed is:

1. A virus-resistant tobacco plant including a plurality of mutations in the genome of the virus-resistant tobacco plant, the plurality of mutations including:
a nonsense mutation in an exon of a translation initiation factor eIF(iso)4E gene, the nonsense mutation causing a production of a translation initiation factor eIF(iso)4E protein with eIF(iso)4E gene function suppressed as compared with a wild type for the virus-resistant tobacco plant and
a nonsense mutation in an exon of a translation initiation factor eIF4E2 gene, the nonsense mutation causing a production of a translation initiation factor eIF4E2 protein with eIF4E2 gene function suppressed as compared with a wild type for the virus-resistant tobacco plant,
an eIF(iso)4E gene including eIF(iso)4E-S and eIF(iso)4E-T genes, and an eIF4E2 gene including eIF4E2-S and eIF4E2-T genes,
the translation initiation factor eIF(iso)4E protein being at least eIF(iso)4E-T protein, and
the translation initiation factor eIF4E2 protein being at least eIF4E2-S protein, wherein the eIF4E2-S gene encodes the eIF4E2-S protein which has a sequence identity of 95% or higher with respect to an amino acid sequence represented by SEQ ID NO: 2,
the eIF4E2-T gene encodes the eIF4E2-T protein which has a sequence identity of 95% or higher with respect to an amino acid sequence represented by SEQ ID NO: 5,
the eIF(iso)4E-S gene encodes the eIF(iso)4E-S protein which has a sequence identity of 97% or higher with respect to an amino acid sequence represented by SEQ ID NO: 8, and
the eIF(iso)4E-T gene encodes the eIF(iso)4E-T protein which has a sequence identity of 97% or higher with respect to an amino acid sequence represented by SEQ ID NO: 11,
wherein the virus is at least both of (i) a strain of Potato virus Y, wherein said strain breaks virus resistance of Virgin A mutant of a tobacco and (ii) the Potato virus Y, and
wherein the virus-resistant tobacco plant is a *Nicotiana* plant and the eIF4E2-S, eIF4E2-T, eIF(iso)4E-S, and eIF(iso)4E-T genes are each a gene existing in a genome of the *Nicotiana* plant,
wherein the wild type for the virus resistant tobacco plant is the same as said virus resistant tobacco plant, except that said wild type for the virus resistant tobacco plant does not have said nonsense mutations, and
wherein the wild type has
(i) a wild-type translation initiation factor eIF(iso)4E-S gene which encodes a translation initiation factor eIF(iso)4E-S protein consisting of an amino acid sequence represented by SEQ ID NO: 8; and
(ii) a wild-type translation initiation factor eIF(iso)4E-T gene which encodes a translation initiation factor eIF(iso)4E-T protein consisting of an amino acid sequence represented by SEQ ID NO: 11.

2. The virus-resistant tobacco plant as set forth in claim 1, wherein:
the translation initiation factor eIF(iso)4E protein includes both of eIF(iso)4E-T protein and eIF(iso)4E-S protein.

3. The virus-resistant tobacco plant as set forth in claim 1, wherein:
the translation initiation factor eIF4E2 protein includes both of eIF4E2-S protein and eIF4E2-T protein.

4. The virus-resistant tobacco plant as set forth in claim 1, wherein the nonsense mutation is any one of the following mutations (1) through (4):
(1) a mutation in which C of codon CAA is substituted by T; (2) a mutation in which C of codon CGA is substituted by T; (3) a mutation in which C of codon CAG is substituted by T; and (4) a mutation in which G (either one or both of two Gs) of codon TGG is substituted by A.

5. The virus-resistant tobacco plant as set forth in claim 1, wherein the virus-resistant tobacco plant further has resistance to a virus belonging to the genus Umbravirus.

6. The virus-resistant tobacco plant as set forth in claim 5, wherein the virus belonging to the genus Umbravirus is Tobacco bushy top virus.

7. A method for producing a virus-resistant tobacco plant, comprising the step of:
producing tobacco plant resistant to a virus by (i) introducing a nonsense mutation into an exon of a translation initiation factor eIF(iso)4E gene, the nonsense mutation causing production of a translation initiation factor eIF(iso)4E protein with eIF(iso)4E gene function suppressed as compared with a wild type for the virus-resistant tobacco plant, and (ii) introducing a nonsense mutation into an exon of a translation initiation factor eIF4E2 gene, the nonsense mutation causing production of a translation initiation factor eIF4E2 with eIF4E2 gene function suppressed as compared with a wild type for the virus-resistant tobacco plant,
the eIF(iso)4E gene including eIF(iso)4E-S and eIF(iso)4E-T genes, and the eIF4E2 gene including eIF4E2-S and eIF4E2-T genes,
the translation initiation factor eIF(iso)4E protein being at least eIF(iso)4E-T protein, and
the translation initiation factor eIF4E2 protein being at least eIF4E2-S protein, wherein
the eIF4E2-S gene encodes the eIF4E2-S protein which has a sequence identity of 95% or higher with respect to an amino acid sequence represented by SEQ ID NO: 2,
the eIF4E2-T gene encodes the eIF4E2-T protein which has a sequence identity of 95% or higher with respect to an amino acid sequence represented by SEQ ID NO: 5, the eIF(iso)4E-S gene encodes the eIF(iso)4E-S protein which has a sequence identity of 97% or higher with respect to an amino acid sequence represented by SEQ ID NO: 8, and the eIF(iso)4E-T gene encodes the eIF(iso)4E-T protein which has a sequence identity of 97% or higher with respect to an amino acid sequence represented by SEQ ID NO: 11, wherein the virus is at least both of (i) a strain of Potato virus Y, wherein said strain breaks virus resistance of Virgin A mutant of a tobacco and (ii) the Potato virus Y, wherein the virus-resistant tobacco plant is a *Nicotiana* plant and the eIF4E2-S, eIF4E2-T, eIF(iso)4E-S, and eIF(iso)4E-T genes are each a gene existing in a genome of the *Nicotiana* plant, wherein the wild type for the virus resistant tobacco plant is the same as said virus resistant tobacco plant, except that said wild type for the virus resistant tobacco plant does not have said nonsense mutations, and wherein the wild type has (i) a wild-type translation initiation factor eIF(iso)4E-S gene which encodes a translation initiation factor eIF (iso)4E-S protein consisting of an amino acid sequence represented by SEQ ID NO: 8; and (ii) a wild-type translation initiation factor eIF(iso)4E-T gene which encodes a translation initiation factor eIF (iso)4E-T protein consisting of an amino acid sequence represented by SEQ ID NO: 11.

8. The method as set forth in claim 7, wherein:

the translation initiation factor eIF(iso)4E protein includes both of eIF(iso)4E-T protein and eIF(iso)4E-S protein.

9. The method as set forth in claim 7, wherein:

the translation initiation factor eIF4E2 protein includes both of eIF4E2-S protein and eIF4E2-T protein.

10. The method as set forth in claim 7, wherein the nonsense mutation is one or more any one of the following mutations (1) through (4): (1) a mutation in which C of codon CAA is substituted by T; (2) a mutation in which C of codon CGA is substituted by T; (3) a mutation in which C of codon CAG is substituted by T; and (4) a mutation in which G (either one or both of two Gs) of codon TGG is substituted by A.

11. The method as set forth in claim 7, wherein the virus is a virus belonging to the genus Potyvirus.

12. The method as set forth in claim 11, wherein the virus belonging to the genus Potyvirus is at least one of (i) a strain of Potato virus Y which strain breaks virus resistance of Virgin A mutant of tobacco and (ii) the Potato virus Y.

13. A method for producing a breeding progeny of a virus-resistant tobacco plant, comprising self-pollinating or cross-pollinating (i) a virus-resistant tobacco plant produced by a method recited in claim 7 or (ii) a progeny of the first generation and the second generation of the virus-resistant tobacco plant thus produced.

14. Leaf tobacco of a virus-resistant tobacco plant recited in claim 1.

15. A tobacco product comprising, as a material, the leaf tobacco recited in claim 14.

* * * * *